(12) United States Patent
Contreras et al.

(10) Patent No.: US 7,491,510 B2
(45) Date of Patent: Feb. 17, 2009

(54) PROTEIN SECRETION IN EUKARYOTIC CELLS

(75) Inventors: Roland Contreras, Merelbeke (BE); Steven Geysens, Kruishoutem (BE)

(73) Assignees: Vlaams Interuniversitair Institute voor Biotechnologie vzw, Zwijnaarde (BE); Universiteit Gent, Gent (BE)

( * ) Notice: Subject to any disclaimer, the term of this patent is extended or adjusted under 35 U.S.C. 154(b) by 196 days.

(21) Appl. No.: 11/225,804

(22) Filed: Sep. 12, 2005

(65) Prior Publication Data

US 2006/0110795 A1    May 25, 2006

Related U.S. Application Data

(63) Continuation of application No. PCT/EP2004/050277, filed on Mar. 10, 2004.

(30) Foreign Application Priority Data

Mar. 12, 2003    (EP) .................................. 03075728

(51) Int. Cl.
*C12P 21/02*    (2006.01)
(52) U.S. Cl. .............. 435/69.1; 435/254.21; 435/254.3; 435/254.5; 435/254.7; 435/254.8; 435/254.9
(58) Field of Classification Search .................. None
See application file for complete search history.

(56) References Cited

FOREIGN PATENT DOCUMENTS

WO    WO 02/00856 A2    1/2002
WO    WO 2004/081201 A1    9/2004

OTHER PUBLICATIONS

Greber et al., Effect of the glucosidase inhibitor 1-deoxynojirimycin on protein secretion from *Saccharomyces cerevisiae*, Enzyme Microb. Technol., Apr. 1988, pp. 246-251, vol. 10.
Maras et al., Filamentous fungi as production organisms for glycoproteins of biomedical interest, Glycoconjugate Journal, 1999, pp. 99-107, vol. 16.
Maras et al., Structural characterization of N-linked oligosaccharides from cellobiohydrolase I secreted by the filamentous fungus *Trichoderma reesei* RUTC 30, Eur. J. Biochem., 1997, pp. 617-625, vol. 245.
Simons et al., Cell wall 1,6-B-glucan synthesis in *Saccharomyces cerevisiae* depends on ER glucosidases I and II, and the molecular chaperone BiP/Kar2p, The EMBO Journal, 1998, pp. 396-405, vol. 17, No. 2.
Uren et al., Abstract, Identification of paracaspases and metacaspases: two ancient families of caspase-like proteins, one of which plays a key role in MALT lymphoma, Mol Cell., Oct. 2000, pp. 961-967, vol. 6, No. 4, http://www.ncbi.nlm.nih.gov/entrez/query.fcgi?cmd=Retrieve&db=pubmed&dopt=Abst...(retrieved Aug. 31, 2004).
PCT International Search Report, PCT/EP2004/050277, dated Aug. 11, 2004.

*Primary Examiner*—James S Ketter
(74) *Attorney, Agent, or Firm*—TraskBritt

(57) ABSTRACT

The present invention relates to the use of a glucosidase II mutation to increase protein secretion in eukaryotic cells. The present invention relates further to the use of eukaryotic cells, comprising a mutant glucosidase II gene, possibly in combination with the expression of a recombinant α-1,2-mannosidase gene and/or a recombinant N-acetylglucosaminyl-transferase gene, as a host for protein secretion.

4 Claims, 20 Drawing Sheets
(2 of 20 Drawing Sheet(s) Filed in Color)

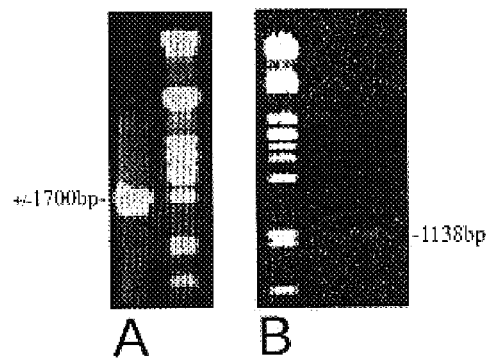

```
Inverse PCR: ATGAGGTCGACGATGGGGCTGTCCTGGAAGTGGACGGCACTCTTCAGCCTTTTAGGTGCC   60
5' RACE    : ATGAGGTCGACGATGGGGCTGTCCTGGAAGTGGACGGCACTCTTCAGCCTTTTAGGTGCC   60
             ************************************************************

Inverse PCR: ATTCTGTGCCTGATCGGGCCTGCCTGTATGCATCATGAACACATCGCGGCTTTCGAAGCA  120
5' RACE    : ATTCTGTGCCTGATCGGGCCTGCCT-----------------------------------   85
             *************************

Inverse PCR: TCTTGCTGACATTGAAACCTTCTAGTGGCCGTCAAGGAACACGAGTTCAAAAAGTGCCAC  180
5' RACE    : ---------------------TGCCCGTCAAGGAACACGAGTTCAAAAAGTGCCAC      220
                                  ***************************************

Inverse PCR: CAGGCCGGCTTCTGCAACCGAAACCGTGCATTGGCCGACCTTGCGGCTTCCCAGAGCTCG  240
5' RACE    : CAGGCCGGCTTCTGCAACCGAAACCGTGCATTGGCCGACCTTGCGGCTTCCCAGAGCTCG  180
             ************************************************************

Inverse PCR: ACCTGGGTGTCTCCCTACAAGGCTGTCTTCGAATCTCCCTCGTTGGAAGACGGAAAGATT  300
5' RACE    : ACCTGGGTGTCTCCCTACAAGGCTGTCTTCGAATCTCCCTCGTTGGAAGACGGAAAGATT  240
             ************************************************************
```

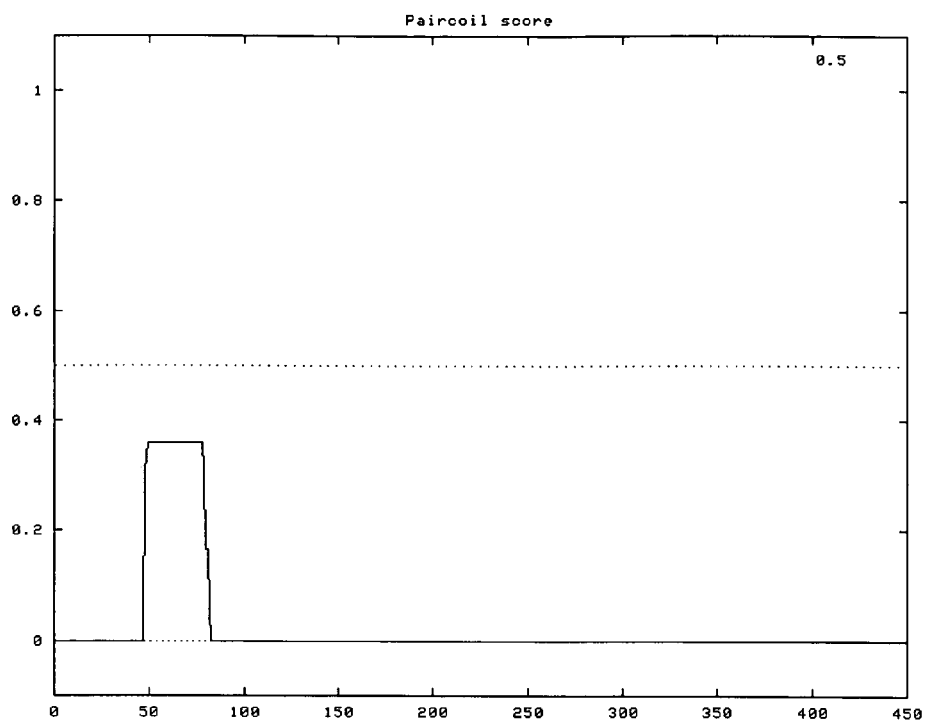
A
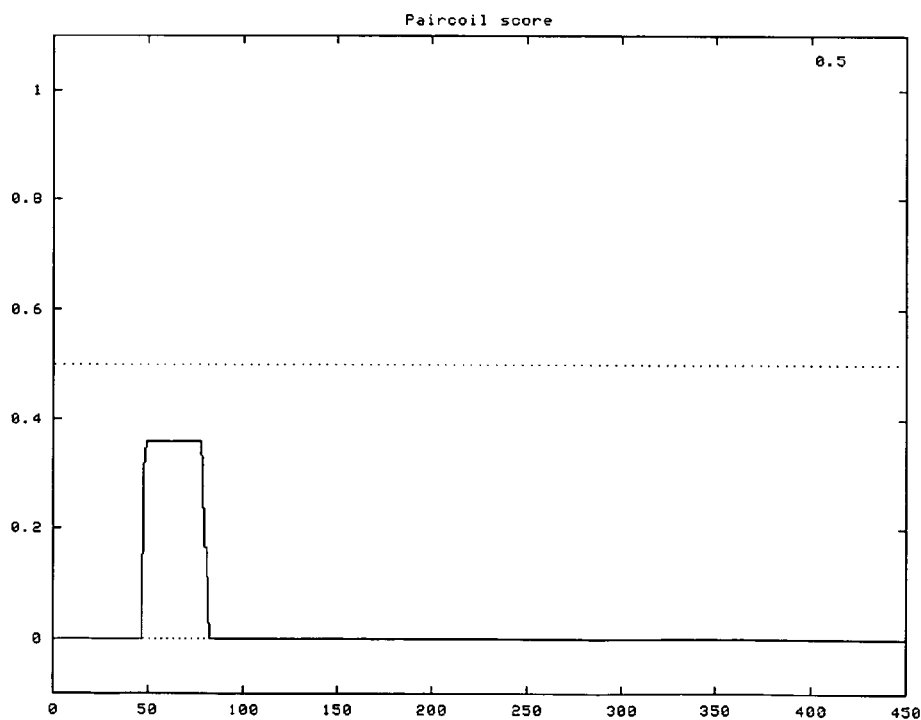
B
FIG. 14

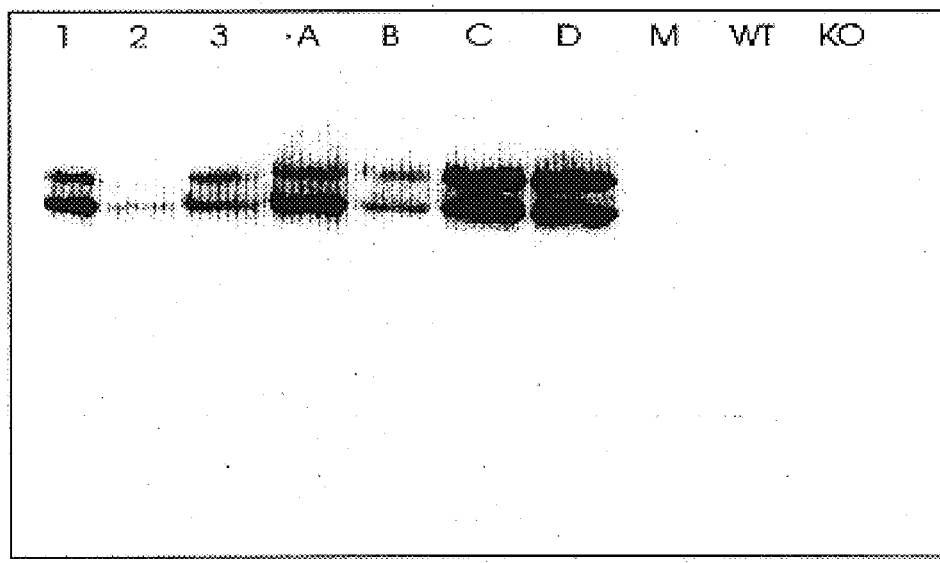
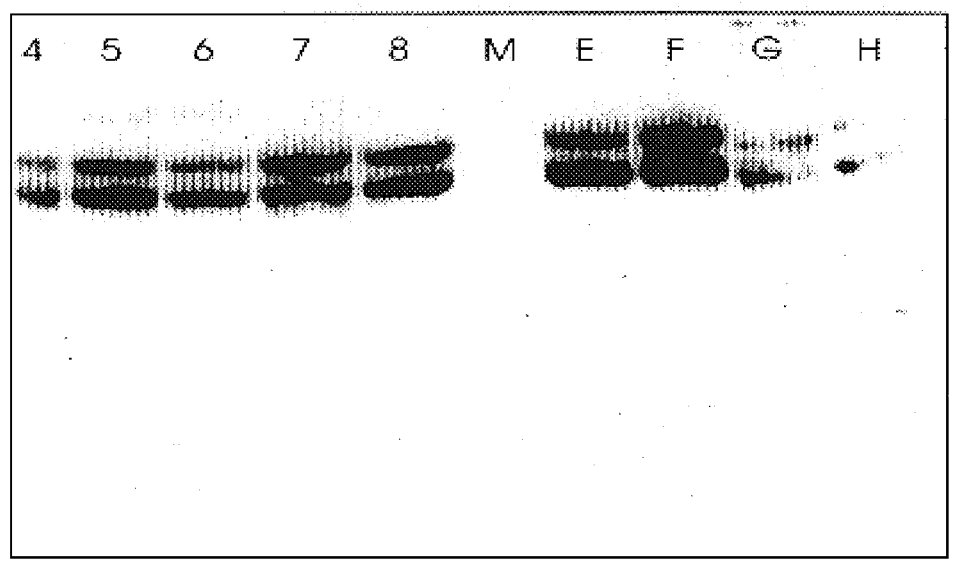
FIG. 18

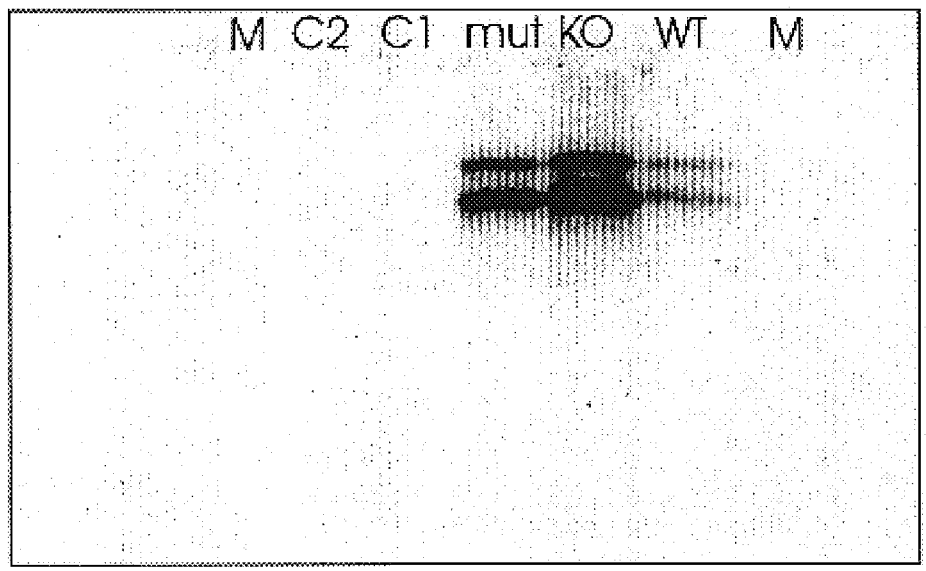
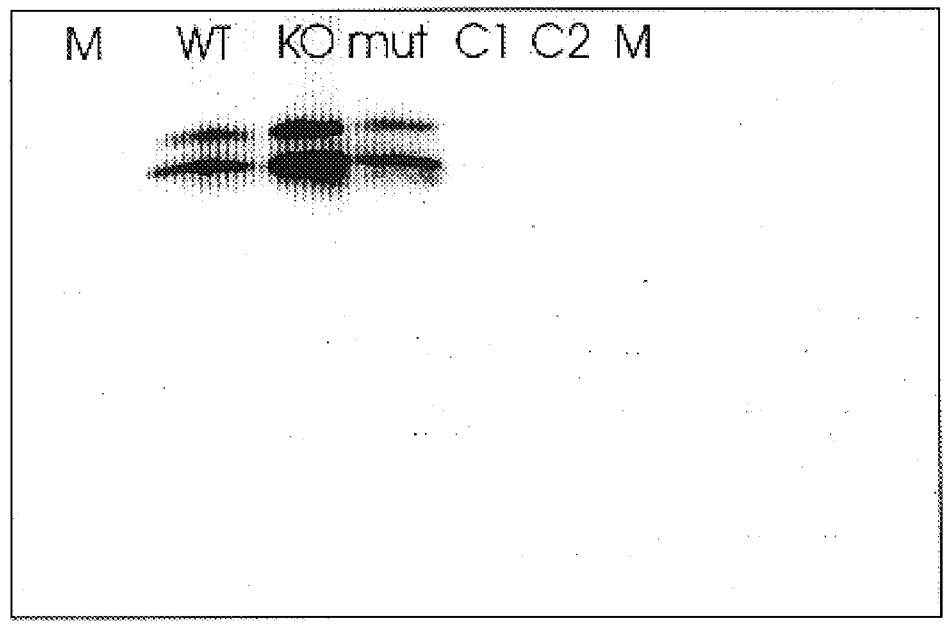
FIG. 19

SEQUENCE LISTING

```
<160> NUMBER OF SEQ ID NOS: 33

<210> SEQ ID NO 1
<211> LENGTH: 2670
<212> TYPE: DNA
<213> ORGANISM: Homo sapiens
<220> FEATURE:
<221> NAME/KEY: CDS
<222> LOCATION: (1)..(2670)
<223> OTHER INFORMATION:
<220> FEATURE:
<221> NAME/KEY: misc_feature
<223> OTHER INFORMATION: GnTI

<400> SEQUENCE: 1 atg ctg aag aag cag tct gca ggg ctt gtg ctg tgg ggc gct atc ctc      48
Met Leu Lys Lys Gln Ser Ala Gly Leu Val Leu Trp Gly Ala Ile Leu
1               5                   10                  15 ttt gtg gcc tgg aat gcc ctg ctc ctc ttc ttc tgg acg cgc cca          96
Phe Val Ala Trp Asn Ala Leu Leu Leu Phe Phe Trp Thr Arg Pro
            20                  25                  30 gca cct ggc agg cca ccc tca gtc agc gct ctc gat ggc gac ccc gcc      144
Ala Pro Gly Arg Pro Pro Ser Val Ser Ala Leu Asp Gly Asp Pro Ala
        35                  40                  45 agc ctc acc cgg gaa gtg att cgc ctg gcc caa gac gcc gag gtg gag      192
Ser Leu Thr Arg Glu Val Ile Arg Leu Ala Gln Asp Ala Glu Val Glu
50                  55                  60 ctg gag cgg cag cgt ggg ctg ctg cag cag atc ggg gat gcc ctg tcg      240
Leu Glu Arg Gln Arg Gly Leu Leu Gln Gln Ile Gly Asp Ala Leu Ser
65                  70                  75                  80 agc cag cgg ggg agg gtg ccc acc gcg gcc cct ccc gcc cag ccg cgt      288
Ser Gln Arg Gly Arg Val Pro Thr Ala Ala Pro Pro Ala Gln Pro Arg
                85                  90                  95 gtg cct gtg acc ccc gcg ccg gcg gtg att ccc atc ctg gtc atc gcc      336
Val Pro Val Thr Pro Ala Pro Ala Val Ile Pro Ile Leu Val Ile Ala
            100                 105                 110 tgt gac cgc agc act gtt cgg cgc tgc ctg gac aag ctg ctg cat tat      384
Cys Asp Arg Ser Thr Val Arg Arg Cys Leu Asp Lys Leu Leu His Tyr
        115                 120                 125 cgg ccc tcg gct gag ctc ttc ccc atc atc gtt agc cag gac tgc ggg      432
Arg Pro Ser Ala Glu Leu Phe Pro Ile Ile Val Ser Gln Asp Cys Gly
    130                 135                 140 cac gag gag acg gcc cag gcc atc gcc tcc tac ggc agc gcg gtc acg      480
His Glu Glu Thr Ala Gln Ala Ile Ala Ser Tyr Gly Ser Ala Val Thr
145                 150                 155                 160 cac atc cgg cag ccc gac ctg agc agc att gcg gtg ccg ccg gac cac      528
His Ile Arg Gln Pro Asp Leu Ser Ser Ile Ala Val Pro Pro Asp His
                165                 170                 175 cgc aag ttc cag ggc tac tac aag atc gcg cgc cac tac cgc tgg gcg      576
Arg Lys Phe Gln Gly Tyr Tyr Lys Ile Ala Arg His Tyr Arg Trp Ala
            180                 185                 190 ctg ggc cag gtc ttc cgg cag ttt cgc ttc ccc gcg gcc gtg gtg gtg      624
```

-continued

| | | |
|---|---|---|
| Leu Gly Gln Val Phe Arg Gln Phe Arg Phe Pro Ala Val Val Val<br>195 200 205 | | |
| gag gat gac ctg gag gtg gcc ccg gac ttc ttc gag tac ttt cgg gcc<br>Glu Asp Asp Leu Glu Val Ala Pro Asp Phe Phe Glu Tyr Phe Arg Ala<br>210 215 220 | 672 | |
| acc tat ccg ctg ctg aag gcc gac ccc tcc ctg tgg tgc gtc tcg gcc<br>Thr Tyr Pro Leu Leu Lys Ala Asp Pro Ser Leu Trp Cys Val Ser Ala<br>225 230 235 240 | 720 | |
| tgg aat gac aac ggc aag gag cag atg gtg gac gcc agc agg cct gag<br>Trp Asn Asp Asn Gly Lys Glu Gln Met Val Asp Ala Ser Arg Pro Glu<br>245 250 255 | 768 | |
| ctg ctc tac cgc acc gac ttt ttc cct ggc ctg ggc tgg ctg ctg ttg<br>Leu Leu Tyr Arg Thr Asp Phe Phe Pro Gly Leu Gly Trp Leu Leu Leu<br>260 265 270 | 816 | |
| gcc gag ctc tgg gct gag ctg gag ccc aag tgg cca aag gcc ttc tgg<br>Ala Glu Leu Trp Ala Glu Leu Glu Pro Lys Trp Pro Lys Ala Phe Trp<br>275 280 285 | 864 | |
| gac gac tgg atg cgg cgg ccg gag cag cgg cag ggg cgg gcc tgc ata<br>Asp Asp Trp Met Arg Arg Pro Glu Gln Arg Gln Gly Arg Ala Cys Ile<br>290 295 300 | 912 | |
| cgc cct gag atc tca aga acg atg acc ttt ggc cgc aag ggt gtg agc<br>Arg Pro Glu Ile Ser Arg Thr Met Thr Phe Gly Arg Lys Gly Val Ser<br>305 310 315 320 | 960 | |
| cac ggg cag ttc ttt gac cag cac ctc aag ttt atc aag ctg aac cag<br>His Gly Gln Phe Phe Asp Gln His Leu Lys Phe Ile Lys Leu Asn Gln<br>325 330 335 | 1008 | |
| cag ttt gtg cac ttc acc cag ctg gac ctg tct tac ctg cag cgg gag<br>Gln Phe Val His Phe Thr Gln Leu Asp Leu Ser Tyr Leu Gln Arg Glu<br>340 345 350 | 1056 | |
| gcc tat gac cga gat ttc ctc gcc cgc gtc tac ggt gct ccc cag ctg<br>Ala Tyr Asp Arg Asp Phe Leu Ala Arg Val Tyr Gly Ala Pro Gln Leu<br>355 360 365 | 1104 | |
| cag gtg gag aaa gtg agg acc aat gac cgg aag gag ctg ggg gag gtg<br>Gln Val Glu Lys Val Arg Thr Asn Asp Arg Lys Glu Leu Gly Glu Val<br>370 375 380 | 1152 | |
| cgg gtg cag tat acg ggc agg gac agc ttc aag gct ttc gcc aag gct<br>Arg Val Gln Tyr Thr Gly Arg Asp Ser Phe Lys Ala Phe Ala Lys Ala<br>385 390 395 400 | 1200 | |
| ctg ggt gtc atg gat gac ctt aag tcg ggg gtt ccg aga gct ggc tac<br>Leu Gly Val Met Asp Asp Leu Lys Ser Gly Val Pro Arg Ala Gly Tyr<br>405 410 415 | 1248 | |
| cgg ggt att gtc acc ttc cag ttc cgg ggc cgc gtc cac ctg gcg<br>Arg Gly Ile Val Thr Phe Gln Phe Arg Gly Arg Val His Leu Ala<br>420 425 430 | 1296 | |
| ccc cca ccg acg tgg gag ggc tat gat cct agc tgg aat atg ctg aag<br>Pro Pro Pro Thr Trp Glu Gly Tyr Asp Pro Ser Trp Asn Met Leu Lys<br>435 440 445 | 1344 | |
| aag cag tct gca ggg ctt gtg ctg tgg ggc gct atc ctc ttt gtg gcc<br>Lys Gln Ser Ala Gly Leu Val Leu Trp Gly Ala Ile Leu Phe Val Ala<br>450 455 460 | 1392 | |
| tgg aat gcc ctg ctg ctc ctc ttc ttc tgg acg cgc cca gca cct ggc<br>Trp Asn Ala Leu Leu Leu Leu Phe Phe Trp Thr Arg Pro Ala Pro Gly<br>465 470 475 480 | 1440 | |
| agg cca ccc tca gtc agc gct ctc gat ggc gac ccc gcc agc ctc acc<br>Arg Pro Pro Ser Val Ser Ala Leu Asp Gly Asp Pro Ala Ser Leu Thr<br>485 490 495 | 1488 | |
| cgg gaa gtg att cgc ctg gcc caa gac gcc gag gtg gag ctg gag cgg<br>Arg Glu Val Ile Arg Leu Ala Gln Asp Ala Glu Val Glu Leu Glu Arg<br>500 505 510 | 1536 | |

```
cag cgt ggg ctg ctg cag cag atc ggg gat gcc ctg tcg agc cag cgg     1584
Gln Arg Gly Leu Leu Gln Gln Ile Gly Asp Ala Leu Ser Ser Gln Arg
        515                 520                 525 ggg agg gtg ccc acc gcg gcc cct ccc gcc cag ccg gtg cct gtg         1632
Gly Arg Val Pro Thr Ala Ala Pro Pro Ala Gln Pro Val Pro Val
530                 535                 540 acc ccc gcg ccg gcg gtg att ccc atc ctg gtc atc gcc tgt gac cgc     1680
Thr Pro Ala Pro Ala Val Ile Pro Ile Leu Val Ile Ala Cys Asp Arg
545                 550                 555                 560 agc act gtt cgg cgc tgc ctg gac aag ctg ctg cat tat cgg ccc tcg     1728
Ser Thr Val Arg Arg Cys Leu Asp Lys Leu Leu His Tyr Arg Pro Ser
                565                 570                 575 gct gag ctc ttc ccc atc atc gtt agc cag gac tgc ggg cac gag gag     1776
Ala Glu Leu Phe Pro Ile Ile Val Ser Gln Asp Cys Gly His Glu Glu
            580                 585                 590 acg gcc cag gcc atc gcc tcc tac ggc agc gcg gtc acg cac atc cgg     1824
Thr Ala Gln Ala Ile Ala Ser Tyr Gly Ser Ala Val Thr His Ile Arg
        595                 600                 605 cag ccc gac ctg agc agc att gcg gtg ccg ccg gac cac cgc aag ttc     1872
Gln Pro Asp Leu Ser Ser Ile Ala Val Pro Pro Asp His Arg Lys Phe
    610                 615                 620 cag ggc tac tac aag atc gcg cgc cac tac cgc tgg gcg ctg ggc cag     1920
Gln Gly Tyr Tyr Lys Ile Ala Arg His Tyr Arg Trp Ala Leu Gly Gln
625                 630                 635                 640 gtc ttc cgg cag ttt cgc ttc ccc gcg gcc gtg gtg gtg gag gat gac     1968
Val Phe Arg Gln Phe Arg Phe Pro Ala Ala Val Val Val Glu Asp Asp
                645                 650                 655 ctg gag gtg gcc ccg gac ttc ttc gag tac ttt cgg gcc acc tat ccg     2016
Leu Glu Val Ala Pro Asp Phe Phe Glu Tyr Phe Arg Ala Thr Tyr Pro
            660                 665                 670 ctg ctg aag gcc gac ccc tcc ctg tgg tgc gtc tcg gcc tgg aat gac     2064
Leu Leu Lys Ala Asp Pro Ser Leu Trp Cys Val Ser Ala Trp Asn Asp
        675                 680                 685 aac ggc aag gag cag atg gtg gac gcc agc agg cct gag ctg ctc tac     2112
Asn Gly Lys Glu Gln Met Val Asp Ala Ser Arg Pro Glu Leu Leu Tyr
    690                 695                 700 cgc acc gac ttt ttc cct ggc ctg ggc tgg ctg ctg ttg gcc gag ctc     2160
Arg Thr Asp Phe Phe Pro Gly Leu Gly Trp Leu Leu Leu Ala Glu Leu
705                 710                 715                 720 tgg gct gag ctg gag ccc aag tgg cca aag gcc ttc tgg gac gac tgg     2208
Trp Ala Glu Leu Glu Pro Lys Trp Pro Lys Ala Phe Trp Asp Asp Trp
                725                 730                 735 atg cgg cgg ccg gag cag cgg cag ggg cgg gcc tgc ata cgc cct gag     2256
Met Arg Arg Pro Glu Gln Arg Gln Gly Arg Ala Cys Ile Arg Pro Glu
            740                 745                 750 atc tca aga acg atg acc ttt ggc cgc aag ggt gtg agc cac ggg cag     2304
Ile Ser Arg Thr Met Thr Phe Gly Arg Lys Gly Val Ser His Gly Gln
        755                 760                 765 ttc ttt gac cag cac ctc aag ttt atc aag ctg aac cag cag ttt gtg     2352
Phe Phe Asp Gln His Leu Lys Phe Ile Lys Leu Asn Gln Gln Phe Val
    770                 775                 780 cac ttc acc cag ctg gac ctg tct tac ctg cag cgg gag gcc tat gac     2400
His Phe Thr Gln Leu Asp Leu Ser Tyr Leu Gln Arg Glu Ala Tyr Asp
785                 790                 795                 800 cga gat ttc ctc gcc cgc gtc tac ggt gct ccc cag ctg cag gtg gag     2448
Arg Asp Phe Leu Ala Arg Val Tyr Gly Ala Pro Gln Leu Gln Val Glu
                805                 810                 815 aaa gtg agg acc aat gac cgg aag gag ctg ggg gag gtg cgg gtg cag     2496
Lys Val Arg Thr Asn Asp Arg Lys Glu Leu Gly Glu Val Arg Val Gln
            820                 825                 830
```

```
tat acg ggc agg gac agc ttc aag gct ttc gcc aag gct ctg ggt gtc    2544
Tyr Thr Gly Arg Asp Ser Phe Lys Ala Phe Ala Lys Ala Leu Gly Val
        835                 840                 845 atg gat gac ctt aag tcg ggg gtt ccg aga gct ggc tac cgg ggt att    2592
Met Asp Asp Leu Lys Ser Gly Val Pro Arg Ala Gly Tyr Arg Gly Ile
850                 855                 860 gtc acc ttc cag ttc cgg ggc cgc cgt gtc cac ctg gcg ccc cca ccg    2640
Val Thr Phe Gln Phe Arg Gly Arg Arg Val His Leu Ala Pro Pro Pro
865                 870                 875                 880 acg tgg gag ggc tat gat cct agc tgg aat                            2670
Thr Trp Glu Gly Tyr Asp Pro Ser Trp Asn
                885                 890

<210> SEQ ID NO 2
<211> LENGTH: 890
<212> TYPE: PRT
<213> ORGANISM: Homo sapiens
<220> FEATURE:
<221> NAME/KEY: misc_feature
<223> OTHER INFORMATION: GnTI

<400> SEQUENCE: 2

Met Leu Lys Lys Gln Ser Ala Gly Leu Val Leu Trp Gly Ala Ile Leu
1               5                   10                  15

Phe Val Ala Trp Asn Ala Leu Leu Leu Leu Phe Phe Trp Thr Arg Pro
                20                  25                  30

Ala Pro Gly Arg Pro Pro Ser Val Ser Ala Leu Asp Gly Asp Pro Ala
            35                  40                  45

Ser Leu Thr Arg Glu Val Ile Arg Leu Ala Gln Asp Ala Glu Val Glu
        50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Pro Ala Gln Pro Arg
                85                  90                  95

Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
        115                 120                 125

Arg Pro Ser Ala Glu Leu Phe Pro Ile Ile Val Ser Gln Asp Cys Gly
    130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
        195                 200                 205

Glu Asp Asp Leu Glu Val Ala Pro Asp Phe Phe Glu Tyr Phe Arg Ala
    210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
                245                 250                 255

Leu Leu Tyr Arg Thr Asp Phe Phe Pro Gly Leu Gly Trp Leu Leu Leu
            260                 265                 270
```

```
Ala Glu Leu Trp Ala Glu Leu Glu Pro Lys Trp Pro Lys Ala Phe Trp
        275                 280                 285

Asp Asp Trp Met Arg Arg Pro Glu Gln Arg Gln Gly Arg Ala Cys Ile
    290                 295                 300

Arg Pro Glu Ile Ser Arg Thr Met Thr Phe Gly Arg Lys Gly Val Ser
305                 310                 315                 320

His Gly Gln Phe Phe Asp Gln His Leu Lys Phe Ile Lys Leu Asn Gln
                325                 330                 335

Gln Phe Val His Phe Thr Gln Leu Asp Leu Ser Tyr Leu Gln Arg Glu
            340                 345                 350

Ala Tyr Asp Arg Asp Phe Leu Ala Arg Val Tyr Gly Ala Pro Gln Leu
        355                 360                 365

Gln Val Glu Lys Val Arg Thr Asn Asp Arg Lys Glu Leu Gly Glu Val
    370                 375                 380

Arg Val Gln Tyr Thr Gly Arg Asp Ser Phe Lys Ala Phe Ala Lys Ala
385                 390                 395                 400

Leu Gly Val Met Asp Asp Leu Lys Ser Gly Val Pro Arg Ala Gly Tyr
                405                 410                 415

Arg Gly Ile Val Thr Phe Gln Phe Arg Gly Arg Val His Leu Ala
            420                 425                 430

Pro Pro Pro Thr Trp Glu Gly Tyr Asp Pro Ser Trp Asn Met Leu Lys
        435                 440                 445

Lys Gln Ser Ala Gly Leu Val Leu Trp Gly Ala Ile Leu Phe Val Ala
    450                 455                 460

Trp Asn Ala Leu Leu Leu Leu Phe Phe Trp Thr Arg Pro Ala Pro Gly
465                 470                 475                 480

Arg Pro Pro Ser Val Ser Ala Leu Asp Gly Asp Pro Ala Ser Leu Thr
                485                 490                 495

Arg Glu Val Ile Arg Leu Ala Gln Asp Ala Glu Val Glu Leu Glu Arg
            500                 505                 510

Gln Arg Gly Leu Leu Gln Gln Ile Gly Asp Ala Leu Ser Ser Gln Arg
        515                 520                 525

Gly Arg Val Pro Thr Ala Ala Pro Pro Ala Gln Pro Arg Val Pro Val
    530                 535                 540

Thr Pro Ala Pro Ala Val Ile Pro Ile Leu Val Ile Ala Cys Asp Arg
545                 550                 555                 560

Ser Thr Val Arg Arg Cys Leu Asp Lys Leu Leu His Tyr Arg Pro Ser
                565                 570                 575

Ala Glu Leu Phe Pro Ile Ile Val Ser Gln Asp Cys Gly His Glu Glu
            580                 585                 590

Thr Ala Gln Ala Ile Ala Ser Tyr Gly Ser Ala Val Thr His Ile Arg
        595                 600                 605

Gln Pro Asp Leu Ser Ser Ile Ala Val Pro Pro Asp His Arg Lys Phe
    610                 615                 620

Gln Gly Tyr Tyr Lys Ile Ala Arg His Tyr Arg Trp Ala Leu Gly Gln
625                 630                 635                 640

Val Phe Arg Gln Phe Arg Phe Pro Ala Ala Val Val Val Glu Asp Asp
                645                 650                 655

Leu Glu Val Ala Pro Asp Phe Phe Glu Tyr Phe Arg Ala Thr Tyr Pro
            660                 665                 670

Leu Leu Lys Ala Asp Pro Ser Leu Trp Cys Val Ser Ala Trp Asn Asp
        675                 680                 685

Asn Gly Lys Glu Gln Met Val Asp Ala Ser Arg Pro Glu Leu Leu Tyr
```

-continued

```
              690               695               700
Arg Thr Asp Phe Phe Pro Gly Leu Gly Trp Leu Leu Ala Glu Leu
705               710               715               720

Trp Ala Glu Leu Glu Pro Lys Trp Pro Lys Ala Phe Trp Asp Asp Trp
                  725               730               735

Met Arg Arg Pro Glu Gln Arg Gln Gly Arg Ala Cys Ile Arg Pro Glu
                  740               745               750

Ile Ser Arg Thr Met Thr Phe Gly Arg Lys Gly Val Ser His Gly Gln
              755               760               765

Phe Phe Asp Gln His Leu Lys Phe Ile Lys Leu Asn Gln Gln Phe Val
770               775               780

His Phe Thr Gln Leu Asp Leu Ser Tyr Leu Gln Arg Glu Ala Tyr Asp
785               790               795               800

Arg Asp Phe Leu Ala Arg Val Tyr Gly Ala Pro Gln Leu Gln Val Glu
                  805               810               815

Lys Val Arg Thr Asn Asp Arg Lys Glu Leu Gly Glu Val Arg Val Gln
                  820               825               830

Tyr Thr Gly Arg Asp Ser Phe Lys Ala Phe Ala Lys Ala Leu Gly Val
              835               840               845

Met Asp Asp Leu Lys Ser Gly Val Pro Arg Ala Gly Tyr Arg Gly Ile
850               855               860

Val Thr Phe Gln Phe Arg Gly Arg Arg Val His Leu Ala Pro Pro Pro
865               870               875               880

Thr Trp Glu Gly Tyr Asp Pro Ser Trp Asn
                  885               890

<210> SEQ ID NO 3
<211> LENGTH: 2208
<212> TYPE: DNA
<213> ORGANISM: Saccharomyces cerevisiae
<220> FEATURE:
<221> NAME/KEY: misc_feature
<223> OTHER INFORMATION: ScKre2 cDNA
<220> FEATURE:
<221> NAME/KEY: CDS
<222> LOCATION: (1)..(1329)
<223> OTHER INFORMATION:

<400> SEQUENCE: 3 atg gcc ctc ttt ctc agt aag aga ctg ttg aga ttt acc gtc att gca        48
Met Ala Leu Phe Leu Ser Lys Arg Leu Leu Arg Phe Thr Val Ile Ala
1               5                   10                  15 ggt gcg gtt att gtt ctc ctc cta aca ttg aat tcc aac agt aga act        96
Gly Ala Val Ile Val Leu Leu Leu Thr Leu Asn Ser Asn Ser Arg Thr
            20                  25                  30 cag caa tat att ccg agt tcc atc tcc gct gca ttt gat ttt acc tca       144
Gln Gln Tyr Ile Pro Ser Ser Ile Ser Ala Ala Phe Asp Phe Thr Ser
        35                  40                  45 gga tct ata tcc cct gaa caa caa gtc atc tct gag gaa aat gat gct       192
Gly Ser Ile Ser Pro Glu Gln Gln Val Ile Ser Glu Glu Asn Asp Ala
    50                  55                  60 aaa aaa tta gag caa agt gct ctg aat tca gag gca agc gaa gac tcc       240
Lys Lys Leu Glu Gln Ser Ala Leu Asn Ser Glu Ala Ser Glu Asp Ser
65                  70                  75                  80 gaa gcc atg gat gaa gaa tcc aag gct ctg aaa gct gcc gct gaa aag       288
Glu Ala Met Asp Glu Glu Ser Lys Ala Leu Lys Ala Ala Ala Glu Lys
                85                  90                  95 gca gat gcc ccg atc gac act aaa aca acc atg gat tat atc act cca       336
Ala Asp Ala Pro Ile Asp Thr Lys Thr Thr Met Asp Tyr Ile Thr Pro
```

-continued

```
                    100                 105                 110
tct ttt gct aac aaa gct ggt aag cca aaa gct tgt tac gtc act ttg      384
Ser Phe Ala Asn Lys Ala Gly Lys Pro Lys Ala Cys Tyr Val Thr Leu
        115                 120                 125 gtg aga aac aag gag ttg aaa ggt ttg cta agc tcc att aaa tat gtg      432
Val Arg Asn Lys Glu Leu Lys Gly Leu Leu Ser Ser Ile Lys Tyr Val
130                 135                 140 gaa aac aaa att aac aag aaa ttc cca tat cct tgg gtt ttc cta aac      480
Glu Asn Lys Ile Asn Lys Lys Phe Pro Tyr Pro Trp Val Phe Leu Asn
145                 150                 155                 160 gat gaa cct ttt act gaa gaa ttc aag gaa gca gtc acc aaa gct gtt      528
Asp Glu Pro Phe Thr Glu Glu Phe Lys Glu Ala Val Thr Lys Ala Val
            165                 170                 175 tct tcc gaa gtt aag ttt ggt att ttg ccc aag gaa cat tgg tca tat      576
Ser Ser Glu Val Lys Phe Gly Ile Leu Pro Lys Glu His Trp Ser Tyr
                180                 185                 190 cct gaa tgg att aat caa acc aag gct gct gaa att cgt gca gat gct      624
Pro Glu Trp Ile Asn Gln Thr Lys Ala Ala Glu Ile Arg Ala Asp Ala
            195                 200                 205 gcc acc aaa tac ata tac ggt ggc tcc gaa tct tat aga cac atg tgt      672
Ala Thr Lys Tyr Ile Tyr Gly Gly Ser Glu Ser Tyr Arg His Met Cys
        210                 215                 220 cgt tac caa tct ggg ttt ttc tgg aga cat gaa tta tta gaa gag tac      720
Arg Tyr Gln Ser Gly Phe Phe Trp Arg His Glu Leu Leu Glu Glu Tyr
225                 230                 235                 240 gat tgg tac tgg cgt gtg gaa cca gac atc aag tta tac tgt gat att      768
Asp Trp Tyr Trp Arg Val Glu Pro Asp Ile Lys Leu Tyr Cys Asp Ile
            245                 250                 255 aat tac gac gtt ttt aag tgg atg caa gaa aac gaa aaa gtt tac ggc      816
Asn Tyr Asp Val Phe Lys Trp Met Gln Glu Asn Glu Lys Val Tyr Gly
                260                 265                 270 ttt acc gtt tct att cat gaa tat gaa gtg acg atc cca aca cta tgg      864
Phe Thr Val Ser Ile His Glu Tyr Glu Val Thr Ile Pro Thr Leu Trp
            275                 280                 285 caa acg tcc atg gat ttc atc aaa aag aac ccc gaa tac tta gat gaa      912
Gln Thr Ser Met Asp Phe Ile Lys Lys Asn Pro Glu Tyr Leu Asp Glu
        290                 295                 300 aac aac ctg atg agt ttt ctt tcg aac gat aat ggt aaa aca tac aat      960
Asn Asn Leu Met Ser Phe Leu Ser Asn Asp Asn Gly Lys Thr Tyr Asn
305                 310                 315                 320 ctg tgc cat ttc tgg tca aac ttt gaa att gca aac ttg aat ttg tgg     1008
Leu Cys His Phe Trp Ser Asn Phe Glu Ile Ala Asn Leu Asn Leu Trp
            325                 330                 335 agg tca cca gcc tac aga gag tat ttt gac act ttg gat cat caa ggt     1056
Arg Ser Pro Ala Tyr Arg Glu Tyr Phe Asp Thr Leu Asp His Gln Gly
                340                 345                 350 gga ttt ttc tac gaa aga tgg ggc gat gct ccc gtt cat tct att gct     1104
Gly Phe Phe Tyr Glu Arg Trp Gly Asp Ala Pro Val His Ser Ile Ala
            355                 360                 365 gct gct ttg ttt ttg cca aag gat aaa atc cat tat ttt tca gac att     1152
Ala Ala Leu Phe Leu Pro Lys Asp Lys Ile His Tyr Phe Ser Asp Ile
        370                 375                 380 ggt tac cat cat cca cct tat gat aac tgc cca ttg gac aag gag gtc     1200
Gly Tyr His His Pro Pro Tyr Asp Asn Cys Pro Leu Asp Lys Glu Val
385                 390                 395                 400 tat aac agt aac aac tgt gaa tgt gac caa ggt aat gat ttc act ttc     1248
Tyr Asn Ser Asn Asn Cys Glu Cys Asp Gln Gly Asn Asp Phe Thr Phe
            405                 410                 415 caa ggt tac tct tgt ggt aag gaa tat tat gat gct caa ggg ttg gta     1296
```

```
                                      -continued

Gln Gly Tyr Ser Cys Gly Lys Glu Tyr Tyr Asp Ala Gln Gly Leu Val
            420                 425                 430 aag cca aaa aac tgg aaa aaa ttc cgt gag tag aaatcttgga acatactgtt    1349
Lys Pro Lys Asn Trp Lys Lys Phe Arg Glu
        435                 440 tctttgtttt gactttatac tttctattta tattttattt ttataactgg ttaagtacac    1409
ataggactgc gtatcaaaca tataagtgag gcaatccaca tttttttttaa agattcgaat   1469 atttttattc tcattagcgt attccgagaa tagttcgaaa aaatataagg tatatcaaga    1529
gtttttacaa gtgagaggaa agaggaataa gctataagca acaaaagcgt aaaaaaatta    1589
gctgaagaca tagaactatg gatgttctca aagaggtgtt gtcactagac caagataaat    1649
ttgaccagct gaaggaaacg agccgagata aaacaaatga acggatgat ccttttgaaa     1709 actatttgaa ggattgtaaa tttaaagcgc cttcaaacaa agatcagtca ccatttgcta    1769
aacttaaatc attacaggaa actcattcta acaatgaagc ggctattaat ataattattc    1829
ctcaattgat tgattactta accgaattca ctaataggtt atcaaattac acacaagatt    1889
tagacttcat taaaaaaaag tccaatgaat tacagtcatt gctcgaatac aactccacta    1949
aactggcaca tatctctcct atggttaatg atttgatgat tcctcctgaa ctcattgatg    2009
acatcattaa agggaagatc aatgaaagct ggcaggataa tataacattc atagcagata    2069
aagaagaaat ttataacaag tataggtcca ataatctcga tcaagacaac aaggacgcag    2129
aaaattcagc aatgctagca ccaaaggatt ttgataagtt atgtcaactc ctggacatcc    2189
taaaaaatgt tattctaga                                                 2208
```

<210> SEQ ID NO 4
<211> LENGTH: 442
<212> TYPE: PRT
<213> ORGANISM: Saccharomyces cerevisiae
<220> FEATURE:
<221> NAME/KEY: misc_feature
<223> OTHER INFORMATION: ScKre2 cDNA

<400> SEQUENCE: 4

```
Met Ala Leu Phe Leu Ser Lys Arg Leu Leu Arg Phe Thr Val Ile Ala
1               5                   10                  15

Gly Ala Val Ile Val Leu Leu Thr Leu Asn Ser Asn Ser Arg Thr
            20                  25                  30

Gln Gln Tyr Ile Pro Ser Ser Ile Ser Ala Ala Phe Asp Phe Thr Ser
        35                  40                  45

Gly Ser Ile Ser Pro Glu Gln Gln Val Ile Ser Glu Glu Asn Asp Ala
    50                  55                  60

Lys Lys Leu Glu Gln Ser Ala Leu Asn Ser Glu Ala Ser Glu Asp Ser
65                  70                  75                  80

Glu Ala Met Asp Glu Glu Ser Lys Ala Leu Lys Ala Ala Glu Lys
            85                  90                  95

Ala Asp Ala Pro Ile Asp Thr Lys Thr Thr Met Asp Tyr Ile Thr Pro
            100                 105                 110

Ser Phe Ala Asn Lys Ala Gly Lys Pro Lys Ala Cys Tyr Val Thr Leu
        115                 120                 125

Val Arg Asn Lys Glu Leu Lys Gly Leu Leu Ser Ser Ile Lys Tyr Val
    130                 135                 140

Glu Asn Lys Ile Asn Lys Lys Phe Pro Tyr Pro Trp Val Phe Leu Asn
145                 150                 155                 160

Asp Glu Pro Phe Thr Glu Glu Phe Lys Glu Ala Val Thr Lys Ala Val
```

```
                165                 170                 175
Ser Ser Glu Val Lys Phe Gly Ile Leu Pro Lys Glu His Trp Ser Tyr
            180                 185                 190

Pro Glu Trp Ile Asn Gln Thr Lys Ala Ala Glu Ile Arg Ala Asp Ala
        195                 200                 205

Ala Thr Lys Tyr Ile Tyr Gly Gly Ser Glu Ser Tyr Arg His Met Cys
    210                 215                 220

Arg Tyr Gln Ser Gly Phe Phe Trp Arg His Glu Leu Leu Glu Glu Tyr
225                 230                 235                 240

Asp Trp Tyr Trp Arg Val Glu Pro Asp Ile Lys Leu Tyr Cys Asp Ile
                245                 250                 255

Asn Tyr Asp Val Phe Lys Trp Met Gln Glu Asn Glu Lys Val Tyr Gly
            260                 265                 270

Phe Thr Val Ser Ile His Glu Tyr Glu Val Thr Ile Pro Thr Leu Trp
        275                 280                 285

Gln Thr Ser Met Asp Phe Ile Lys Lys Asn Pro Glu Tyr Leu Asp Glu
    290                 295                 300

Asn Asn Leu Met Ser Phe Leu Ser Asn Asp Asn Gly Lys Thr Tyr Asn
305                 310                 315                 320

Leu Cys His Phe Trp Ser Asn Phe Glu Ile Ala Asn Leu Asn Leu Trp
                325                 330                 335

Arg Ser Pro Ala Tyr Arg Glu Tyr Phe Asp Thr Leu Asp His Gln Gly
            340                 345                 350

Gly Phe Phe Tyr Glu Arg Trp Gly Asp Ala Pro Val His Ser Ile Ala
        355                 360                 365

Ala Ala Leu Phe Leu Pro Lys Asp Lys Ile His Tyr Phe Ser Asp Ile
    370                 375                 380

Gly Tyr His His Pro Pro Tyr Asp Asn Cys Pro Leu Asp Lys Glu Val
385                 390                 395                 400

Tyr Asn Ser Asn Asn Cys Glu Cys Asp Gln Gly Asn Asp Phe Thr Phe
                405                 410                 415

Gln Gly Tyr Ser Cys Gly Lys Glu Tyr Tyr Asp Ala Gln Gly Leu Val
            420                 425                 430

Lys Pro Lys Asn Trp Lys Lys Phe Arg Glu
        435                 440

<210> SEQ ID NO 5
<211> LENGTH: 100
<212> TYPE: PRT
<213> ORGANISM: Saccharomyces cerevisiae
<220> FEATURE:
<221> NAME/KEY: MISC_FEATURE
<223> OTHER INFORMATION: ScKre2 Golgi localization signal

<400> SEQUENCE: 5

Met Ala Leu Phe Leu Ser Lys Arg Leu Leu Arg Phe Thr Val Ile Ala
1               5                   10                  15

Gly Ala Val Ile Val Leu Leu Thr Leu Asn Ser Asn Ser Arg Thr
            20                  25                  30

Gln Gln Tyr Ile Pro Ser Ser Ile Ser Ala Ala Phe Asp Phe Thr Ser
        35                  40                  45

Gly Ser Ile Ser Pro Glu Gln Gln Val Ile Ser Glu Glu Asn Asp Ala
    50                  55                  60

Lys Lys Leu Glu Gln Ser Ala Leu Asn Ser Glu Ala Ser Glu Asp Ser
65                  70                  75                  80
```

Glu Ala Met Asp Glu Glu Ser Lys Ala Leu Lys Ala Ala Glu Lys
            85                  90                  95
Ala Asp Ala Pro
            100

<210> SEQ ID NO 6
<211> LENGTH: 23
<212> TYPE: DNA
<213> ORGANISM: Artificial Sequence
<220> FEATURE:
<223> OTHER INFORMATION: primer 1
<220> FEATURE:
<221> NAME/KEY: misc_feature
<222> LOCATION: (3)..(15)
<223> OTHER INFORMATION: N here stands for inosine
<220> FEATURE:
<221> NAME/KEY: misc_feature
<222> LOCATION: (12)..(12)
<223> OTHER INFORMATION: H can be A, C or T

<400> SEQUENCE: 6
gtntatggna thccngagca tgc                                            23

<210> SEQ ID NO 7
<211> LENGTH: 21
<212> TYPE: DNA
<213> ORGANISM: Artificial Sequence
<220> FEATURE:
<223> OTHER INFORMATION: primer 2
<220> FEATURE:
<221> NAME/KEY: misc_feature
<222> LOCATION: (2)..(20)
<223> OTHER INFORMATION: N here stands for inosine
<220> FEATURE:
<221> NAME/KEY: misc_feature
<222> LOCATION: (13)..(13)
<223> OTHER INFORMATION: K can be G or T

<400> SEQUENCE: 7
gngcgtgngc nckgaagaan g                                              21

<210> SEQ ID NO 8
<211> LENGTH: 22
<212> TYPE: DNA
<213> ORGANISM: Artificial Sequence
<220> FEATURE:
<223> OTHER INFORMATION: primer 3
<220> FEATURE:
<221> NAME/KEY: misc_feature
<222> LOCATION: (3)..(21)
<223> OTHER INFORMATION: N here stands for inosine
<220> FEATURE:
<221> NAME/KEY: misc_feature
<222> LOCATION: (4)..(4)
<223> OTHER INFORMATION: S can be G or C
<220> FEATURE:
<221> NAME/KEY: misc_feature
<222> LOCATION: (5)..(5)
<223> OTHER INFORMATION: W can be A or T

<400> SEQUENCE: 8
tgnswnccng cgaagaangc nc                                             22

<210> SEQ ID NO 9
<211> LENGTH: 20
<212> TYPE: DNA
<213> ORGANISM: Artificial Sequence
<220> FEATURE:
<223> OTHER INFORMATION: PCR primer ROT2TR4_AS

<400> SEQUENCE: 9
gttaaacgtt tcgtcccacc                                              20

<210> SEQ ID NO 10
<211> LENGTH: 19
<212> TYPE: DNA
<213> ORGANISM: Artificial Sequence
<220> FEATURE:
<223> OTHER INFORMATION: PCR primer ROT2TR1_S

<400> SEQUENCE: 10
ggctccatcc ctttcatgc                                               19

<210> SEQ ID NO 11
<211> LENGTH: 20
<212> TYPE: DNA
<213> ORGANISM: Artificial Sequence
<220> FEATURE:
<223> OTHER INFORMATION: PCR primer ROT2TR-RLMRACE

<400> SEQUENCE: 11
gatatactcg aagacgtcgg                                              20

<210> SEQ ID NO 12
<211> LENGTH: 18
<212> TYPE: DNA
<213> ORGANISM: Artificial Sequence
<220> FEATURE:
<223> OTHER INFORMATION: sense primer

<400> SEQUENCE: 12
atgaggtcga cgatgggg                                                18

<210> SEQ ID NO 13
<211> LENGTH: 17
<212> TYPE: DNA
<213> ORGANISM: Artificial Sequence
<220> FEATURE:
<223> OTHER INFORMATION: antisense primer

<400> SEQUENCE: 13
agccagcttg atgctcc                                                 17

<210> SEQ ID NO 14
<211> LENGTH: 22
<212> TYPE: DNA
<213> ORGANISM: Artificial Sequence
<220> FEATURE:
<223> OTHER INFORMATION: primer ROT2TR3_S

<400> SEQUENCE: 14
tatctctggt ttcccgttct cg                                           22

<210> SEQ ID NO 15
<211> LENGTH: 21
<212> TYPE: DNA
<213> ORGANISM: Artificial Sequence
<220> FEATURE:
<223> OTHER INFORMATION: primer ROT2TR0_AS

<400> SEQUENCE: 15
ctggtcatca atcgccaagc c                                            21

<210> SEQ ID NO 16
<211> LENGTH: 20
<212> TYPE: DNA

```
<213> ORGANISM: Artificial Sequence
<220> FEATURE:
<223> OTHER INFORMATION: primer ROT2TR2_S

<400> SEQUENCE: 16
atcaatgagc aactcctggc                                              20

<210> SEQ ID NO 17
<211> LENGTH: 31
<212> TYPE: DNA
<213> ORGANISM: Artificial Sequence
<220> FEATURE:
<223> OTHER INFORMATION: sense primer used to induce the silent mutation

<400> SEQUENCE: 17
ccatgtgaag gcccggttg gggatgactg g                                  31

<210> SEQ ID NO 18
<211> LENGTH: 31
<212> TYPE: DNA
<213> ORGANISM: Artificial Sequence
<220> FEATURE:
<223> OTHER INFORMATION: antisense primer used to induce the silent
      mutation

<400> SEQUENCE: 18
ccagtcatcc caacccggg ccttcacatg g                                  31

<210> SEQ ID NO 19
<211> LENGTH: 27
<212> TYPE: DNA
<213> ORGANISM: Artificial Sequence
<220> FEATURE:
<223> OTHER INFORMATION: sense primer

<400> SEQUENCE: 19
gaattcccgc ggtacgtaat tatgagg                                      27

<210> SEQ ID NO 20
<211> LENGTH: 27
<212> TYPE: DNA
<213> ORGANISM: Artificial Sequence
<220> FEATURE:
<223> OTHER INFORMATION: antisense primer

<400> SEQUENCE: 20
gtcgacctca taattacgta ccgcggg                                      27

<210> SEQ ID NO 21
<211> LENGTH: 27
<212> TYPE: DNA
<213> ORGANISM: Artificial Sequence
<220> FEATURE:
<223> OTHER INFORMATION: primer ROT2ScNco_S

<400> SEQUENCE: 21
cttgccatgg tcctttgaa atggctc                                       27

<210> SEQ ID NO 22
<211> LENGTH: 33
<212> TYPE: DNA
<213> ORGANISM: Artificial Sequence
<220> FEATURE:
<223> OTHER INFORMATION: primer ROT2ScMycHind_AS

<400> SEQUENCE: 22
```

```
cccaagcttc tacagatcct cttctgagat gag                              33
```

<210> SEQ ID NO 23
<211> LENGTH: 30
<212> TYPE: DNA
<213> ORGANISM: Artificial Sequence
<220> FEATURE:
<223> OTHER INFORMATION: primer ROT2Sc_S

<400> SEQUENCE: 23

```
ccgctcgaga tggtcctttt gaaatggctc                                  30
```

<210> SEQ ID NO 24
<211> LENGTH: 30
<212> TYPE: DNA
<213> ORGANISM: Artificial Sequence
<220> FEATURE:
<223> OTHER INFORMATION: primer ROT2Sc_AS

<400> SEQUENCE: 24

```
ccgggcccaa aataacttc ccaatcttca                                   30
```

<210> SEQ ID NO 25
<211> LENGTH: 19
<212> TYPE: DNA
<213> ORGANISM: Artificial Sequence
<220> FEATURE:
<223> OTHER INFORMATION: gene specific antisense primer

<400> SEQUENCE: 25

```
caactcgtcg tgagcaagg                                              19
```

<210> SEQ ID NO 26
<211> LENGTH: 20
<212> TYPE: DNA
<213> ORGANISM: Artificial Sequence
<220> FEATURE:
<223> OTHER INFORMATION: sense primer

<400> SEQUENCE: 26

```
ccatattttc ctgctctccc                                             20
```

<210> SEQ ID NO 27
<211> LENGTH: 31
<212> TYPE: DNA
<213> ORGANISM: Artificial Sequence
<220> FEATURE:
<223> OTHER INFORMATION: Sense primer ROT2 gene

<400> SEQUENCE: 27

```
tacgggcccg ggaaaaaaac gaagtgatat c                                31
```

<210> SEQ ID NO 28
<211> LENGTH: 23
<212> TYPE: DNA
<213> ORGANISM: Artificial Sequence
<220> FEATURE:
<223> OTHER INFORMATION: Antisense primer for ROT2 gene

<400> SEQUENCE: 28

```
ccttgtcgag gtgggaaatg tcc                                         23
```

<210> SEQ ID NO 29
<211> LENGTH: 31
<212> TYPE: DNA
<213> ORGANISM: Artificial Sequence

```
<220> FEATURE:
<223> OTHER INFORMATION: Antisense primer ROT2(AS)

<400> SEQUENCE: 29
ccgggcccaa aaataacttc ccaatcttca g                                        31

<210> SEQ ID NO 30
<211> LENGTH: 19
<212> TYPE: DNA
<213> ORGANISM: Artificial Sequence
<220> FEATURE:
<223> OTHER INFORMATION: Mutation sense primer

<400> SEQUENCE: 30
gtaggatcct cgcaaagcc                                                      19

<210> SEQ ID NO 31
<211> LENGTH: 25
<212> TYPE: DNA
<213> ORGANISM: Artificial Sequence
<220> FEATURE:
<223> OTHER INFORMATION: Mutation antisense primer

<400> SEQUENCE: 31
gacaattaca ttgaggaaag atccg                                               25

<210> SEQ ID NO 32
<211> LENGTH: 300
<212> TYPE: DNA
<213> ORGANISM: Artificial Sequence
<220> FEATURE:
<223> OTHER INFORMATION: Inverse PCR fragment

<400> SEQUENCE: 32
atgaggtcga cgatggggct gtcctggaag tggacggcac tcttcagcct tttaggtgcc         60
attctgtgcc tgatcgggcc tgcctgtatg catcatgaac acatcgcggc tttgaagca         120 tcttgctgac attgaaacct tctagtggcc gtcaaggaac acgagttcaa aaagtgccac        180
caggccggct tctgcaaccg aaaccgtgca ttggccgacc ttgcggcttc ccagagctcg        240
acctgggtgt ctccctacaa ggctgtcttc gaatctccct cgttggaaga cggaaagatt        300

<210> SEQ ID NO 33
<211> LENGTH: 240
<212> TYPE: DNA
<213> ORGANISM: Artificial Sequence
<220> FEATURE:
<223> OTHER INFORMATION: 5' Race fragment

<400> SEQUENCE: 33
atgaggtcga cgatggggct gtcctggaag tggacggcac tcttcagcct tttaggtgcc         60
attctgtgcc tgatcgggcc tgccttggcg gtcaaggaac acgagttcaa aaagtgccac        120
caggccggct tctgcaaccg aaaccgtgca ttggccgacc ttgcggcttc ccagagctcg        180
acctgggtgt ctccctacaa ggctgtcttc gaatctccct cgttggaaga cggaaagatt        240
```

US 7,491,510 B2

PROTEIN SECRETION IN EUKARYOTIC CELLS

CROSS-REFERENCE TO RELATED APPLICATION

This application is a continuation of PCT International Patent Application No. PCT/ep2004/050277, filed on Mar. 10, 2004, designating the United States of America, and published, in English, as PCT International Publication No. WO 2004/081201 A1 on Sep. 23, 2004, which itself claims priority from EP 03075728.0 filed on Mar. 12, 2003, the contents of the entirety of both of which are incorporated herein by this reference.

TECHNICAL FIELD

The present invention relates generally to biotechnology, and, more particularly, to the use of a glucosidase II mutation to increase protein secretion in eukaryotic cells. The present invention relates further to the use of eukaryotic cells, comprising a mutant and/or recombinant glucosidase II gene, possibly in combination with the expression of a recombinant α-1,2-mannosidase gene and/or a recombinant N-acetylglucosaminyl-transferase gene, as a host for protein secretion.

BACKGROUND

Filamentous fungi can produce high yields of proteins and metabolites. Impressive increases in the secretion of homologous proteins were obtained with traditional strain-improvement strategies based on various mutagenesis approaches. As such, industrial strains have been created that secrete >20 g/l of a specific endogenous protein. In this way, filamentous fungi seem promising organisms for the production of heterologous proteins of biomedical interest (Maras et al., 1999; Punt et al., 2002).

However, unlike mammalian cells, these lower eukaryotic organisms do not synthesize complex type protein-linked oligosaccharides. This inability hampers the use of therapeutic glycoproteins produced by filamentous fungi, since they mostly synthesize high-mannose type N-glycans. Due to the presence of several lectins on human cells, glycoproteins carrying this type of glycosylation are rapidly cleared from the blood stream. This significantly reduces their therapeutic value.

Not only are lower eukaryotes like filamentous fungi, unable to synthesize complex type oligosaccharides, they sometimes also elongate the high-mannose type glycans with fungal-specific glycan residues like mannosephosphate, α-1,3-mannose and galactofuranose. Some of these residues induce an immunogenic response in humans, again reducing the therapeutic value of such glycoproteins.

Protein N-glycosylation originates in the endoplasmic reticulum (ER), where an N-linked oligosaccharide ($Glc_3Man_9GlcNAc_2$) assembled on dolichol (a lipid carrier intermediate) is transferred to the appropriate Asn of a nascent protein. This is a co-translational event common to all eukaryotic organisms. The three glucose residues and one specific α-1,2-linked mannose residue are removed by specific glucosidases and an α-1,2-mannosidase in the ER, resulting in the core oligosaccharide structure, $Man_8GlcNAc_2$. Proteins with this core sugar structure are transported to the Golgi apparatus where the sugar moiety undergoes various modifications. Significant differences exist in the modifications of the sugar chain in the Golgi apparatus between lower and higher eukaryotes.

In mammalian cells, the modification of the sugar chain can follow three different pathways depending on the protein moiety to which it is added. That is: (1) the core sugar chain does not change; (2) the core sugar chain is changed by adding the N-acetylglucosamine-1-phosphate moiety (GlcNAc-1-P) in UDP-N-acetyl glucosamine (UDP-GlcNAc) to the 6-position of mannose in the core sugar chain, followed by removal of the GlcNAc moiety to form an acidic sugar chain in the glycoprotein; and (3) the core sugar chain is first converted into $Man_5GlcNAc_2$ by removing three mannose residues with Golgi a Mannosidase I; $Man_5GlcNAc_2$ is then further modified by adding GlcNAc and removing two more mannose residues, followed by sequentially adding GlcNAc, galactose (Gal), and N-acetylneuraminic acid (also called sialic acid (NeuNAc)) to form various hybrid or complex sugar chains (R. Kornfeld and S. Kornfeld, 1985; Chiba et al., 1998).

In filamentous fungi like Trichoderma reesei, only a part of the $Man_{8(9)}GlcNAc_2$ structures are (partially) trimmed down to $Man_5GlcNAc_2$. These oligosaccharides can then be further modified to fungal-specific glycans through the addition of mannosephosphate residues in a diester linkage. As such, a variety of sugar residues can be found on Trichoderma secreted glycoproteins, consisting of $Man_{5-8(9)}GlcNAc_2$ with or without one or two mannosephosphate residues. An exception to this general Trichoderma glycosylation pattern is the Rut-C30 strain, producing mainly $GlcMan_{7(9)}GlcNAc_2$ or $GlcMan_{7(9)}GlcNAc_2$-P-Man (Maras et al., 1997).

A clear need exists for a fungal strain, such as a Trichoderma strain, that is able to secrete large amounts of a heterologous protein with a more human-compatible glycosylation profile. As such, the Rut-C30 strain of T. Reesei which is a hypersecretor of endogenous cellulases (up to 30 g/l), would be an interesting strain for heterologous protein production, but it is hampered by its aberrant glycosylation pattern, compared to the wild-type Qm6a strain and to most of the industrial mutant strains. In these Trichoderma strains, a first α-1,2-linked glucose residue is removed by glucosidase I, after transfer of the $Glc_3Man_9GlcNAc_2$ structure to the protein. This is followed by the removal of the two α-1,3-linked glucose residues by glucosidase II. However in the Rut-C30 strain, NMR analysis revealed that more than 80% of the glycan structures synthesized on cellobiohydrolase I (CBH I) still contained one α-1,3-linked glucose residue at the end of the α-1,3-arm of the high-mannose core structure (Maras et al., 1997). This indicates a malfunction at the level of the glucosidase II. This malfunction could be due to a reduced expression level of the enzyme.

SUMMARY OF THE INVENTION

Surprisingly, we found that this malfunction is due to the presence of a frameshift mutation within the Rut-C30 glucosidase II ORF, presumably deleting or severely damaging the Glc-α-1,3-Man substrate binding site, but not the Glc-α-1,3-Glc substrate binding site. This presumption would be in accordance with the kinetic model proposed by Alonso et al. (1993), in which the two substrate binding sites are proposed, and could also explain why the removal of the first α-1,3-linked glucose residue does not seem to present any problem.

Even more surprisingly we found that a Rut-C30 strain expressing a fully functional (ER-localized) T. Reesei glucosidase II was showing a changed glycosylation profile, resembling that of most other T. Reesei strains. However, the secretion level was affected by the expression of the glucosidase II. Coexpression of glucosidase II, α-1,2-mannosidase and GlcNac-transferase resulted in a modified secretion, combined with a human-like glycosylation profile. The resulting strain may be useful for the production of heterologous proteins of which the glycosylation pattern is critical.

Knocking out the glucosidase II gene in *Saccharomyces cerevisiae*, as well as the introduction of the mutant glucosidase II form similar to the *T. Reesei* RUT C30 mutation confirms the unexpected effect of the glucosidase II mutation on the protein secretion.

Therefore, one embodiment of the invention involves the use of a glucosidase II mutation to increase protein secretion in eukaryotic cells. Every mutation that affects the activity of the glucosidase II may be used, and it may be, as a non-limiting example, an inactivating or down-regulating mutation in the promoter region, an inactivating knock out of a part of the coding sequence or of the whole coding sequence, a point mutation in one or more of the subunits of the glucosidase II, or an exchange of one or more of the subunits by a mutant subunit or by a subunit of another species. Preferably, the effect of the mutation is a decrease in activity of glucosidase II. Preferably, the subunit that carries the mutation is subunit alpha.

The eukaryotic cells may be any eukaryotic cells, including, but not limited to mammalian cells, insect cells, plant cells and fungal cells. Preferably, said eukaryotic cell is a fungal cell, even more preferably a filamentous fungus or a yeast cell. Filamentous fungi are known to the person, skilled in the art, and include, but are not limited to, species from the genera *Aspergillus, Fusarium, Geotrichum, Monascus, Monilia, Mucor, Penecillium, Rhizopus, Trichoderma* and *Ustilago*. Preferably, the filamentous fungus is a *Trichoderma* sp., even more preferably the filamentous fungus is *T. Reesei* Rut-C30. Yeast cells are also known to the person skilled in the art and include, but are not limited to *Saccharomyces* sp., *Pichia* sp., *Hansenula* sp., *Kluyveromyces* sp. and *Schizosaccharomyces pombe*. Preferably, the yeast cell is a *Saccharomyces cerevisiae* strain.

The secreted proteins may be homologous proteins or heterologous proteins, and they may be glycosylated or not glycosylated. Preferably, the secreted proteins are heterologous proteins, and even more preferably, the proteins are glycosylated heterologous proteins.

Another aspect of the invention is the use of a recombinant filamentous fungus comprising a defective recombinant glucosidase II as a host for protein secretion.

A defective recombinant glucosidase II as used here means that the endogenous sequence of the promoter and/or of the coding sequence of one or more of the subunits of glucosidase II has been replaced by a non-endogenous sequence. Preferably, the subunit that is replaced is subunit alpha. The non-endogenous sequence may be the sequence of a non-glucosidase II gene of the same organism, or the sequence of another organism, or an artificial sequence. The resulting defective recombinant glucosidase II should have an activity that is different from the wild-type, preferentially a lower activity. Filamentous fungi are known to the person, skilled in the art, and include, but are not limited to, species from the genera *Aspergillus, Fusarium, Geotrichum, Monascus, Monilia, Mucor, Penecillium, Rhizopus, Trichoderma* and *Ustilago*. Preferably, the filamentous fungus is a *Trichoderma* sp., even more preferably the filamentous fungus is *T. Reesei* Rut-C30.

Protein secretion as used here may be the secretion of an endogenous protein, or the secretion of a heterologous protein.

Still another aspect of the invention is the use of a yeast comprising a defective glucosidase II as a host for protein secretion. The defective glucosidase II has an activity that is different from the wild-type, preferably a lower activity. The defective glucosidase II might be obtained by random mutagenesis. However, preferably the defective glucosidase II is a defective recombinant glucosidase II, as discussed above. Yeast cells are preferably selected from the group consisting of *Saccharomyces* sp., *Pichia* sp., *Hansenula* sp., *Kluyveromyces* sp. and *Schizosaccharomyces pombe*. Even more preferably, the yeast cell is a *Saccharomyces cerevisiae* strain.

Still another aspect of the invention is a method to increase protein secretion of a eukaryotic cell, comprising mutagenesis of glucosidase II. Techniques for mutagenesis are known to the person skilled in the art, and include, but are not limited to chemical mutagenesis, physical mutagenesis such as UV radiation, or site directed mutagenesis by recombinant DNA techniques. Preferably, the mutagenesis is site directed mutagenesis. Preferably, the eukaryotic cell is a fungal cell, such as a filamentous fungus or a yeast cell. Glucosidase II genes have been cloned from a number of mammalian species including rat (Trombetta et al., 1996), mouse (Arendt et al., 1997), pig (Flura et al., 1997) and human (Trombetta et al., 1996, genbank accession number D42041). The glucosidase II protein from these mammalian species consists of an alpha and a beta subunit. The alpha subunit is about 110 kDa and contains the catalytic activity of the enzyme, while the beta subunit has a C-terminal HDEL ER-retention sequence (SEQ ID NO:34) and is believed to be required for the ER localization of the enzyme. Similar results were obtained for the fission yeast *S. pombe* (d'Alessio et al., 1999). The sequence of the glucosidase II gene from *S. cerevisiae* has also been identified (ORF YBR229c, located on chromosome II, genbank accession number Z36098). This gene encodes a protein of about 110 kDa, which shows a high degree of homology to the mammalian alpha subunits. During the course of our work, the genes coding for the α-subunits of the *T. Reesei* Rut-C30 and the *Aspergillus niger* glucosidase II protein, were cloned, facilitating the site directed mutagenesis of the genes.

Transformation vectors and transformation techniques for yeast and filamentous fungi are known to the person skilled in the art. For *Trichoderma*, preferred vectors carrying a glucosidase II expression sequence are called pFGPDglsII-Treesei and pFGPDglsIITreesei(Myc).

Vectors can be introduced into the cells of a *Trichoderma* strain using known methods such as the protoplast technique, described by Penttila et al., 1987. Other published methods useful for transformation of the plasmids or linear vectors include electroporation (Goldman et al., 1990), particle bombardment (Lorito et al., 1993) and an *Agrobacterium tumefaciens*-mediated strategy (de Groot et al., 1998).

During the transformation procedure, the glucosidase II expression sequence is cotransformed with a selection plasmid. By "selection plasmid" is meant a plasmid carrying a selection marker. By "selection marker" is meant an expression cassette coding for a specific gene product, which enables us to discriminate between a transformed strain and a non-transformed strain. Transformed *Trichoderma* clones can be selected by using appropriate techniques including, but not limited to, culturing auxotrophic cells after transformation in the absence of the biochemical product required (due to the cell's auxotrophy), selection for and detection of a new phenotype, or culturing in the presence of an antibiotic which is toxic to the fungus in the absence of a resistance gene within the transformants. Examples of available selection markers for *T. Reesei* are the acetamidase expression cassette of the vector p3SR2 (Hynes et al., 1983) (enabling transformed strains to grow on acetamide as a sole nitrogen source), the *E. coli* hygromycin B phosphotransferase cassette of vector pAN7.1 (Punt et al., 1987) and the *Streptoalloteichus hindustanus* phleomycin-binding protein expression cassette of vector pAN8.1 (Mattern et al., 1988) (enabling the transformed strains to grow on a certain concentration of hygromycin resp. phleomycin).

Another aspect of the invention is a genetically engineered filamentous fungus expressing a glucosidase II gene according to the invention, further expressing a recombinant α-1,2-mannosidase gene. Preferably, the α-1,2-mannosidase gene is fused to an ER retention signal. More preferably, the ER retention signal is derived from the MNS1 protein of *S. cerevisiae*. Even more preferably, the retention signal comprises the sequence HDEL (SEQ ID NO:34). Preferably, the filamentous fungus is a *Trichoderma* sp., even more preferably the filamentous fungus is *T. Reesei* Rut-C30.

An α-1,2-mannosidase cleaves the α-1,2-linked mannose residues at the end of $Man_{8(9)}GlcNAc_2$, and converts this core oligosaccharide on glycoproteins to $Man_5GlcNAc_2$ which is thought to be a very poor substrate for a Golgi phosphomannosyltransferase. Thus, by introducing an α-1,2-mannosidase into filamentous fungi such as *Trichoderma*, glycoproteins with reduced mannose and phosphate content can be produced. Furthermore, $Man_5GlcNAc_2$ is the acceptor substrate for the mammalian N-acetylglucosaminyl transferase I and as such a key structure in the synthesis of hybrid- and complex-type sugar chains, characteristic for mammalian glycoproteins.

According to the present invention, a genetically engineered *Trichoderma* strain capable of expressing an α-1,2-mannosidase can be generated by introducing into the filamentous fungus a nucleotide sequence capable of expressing the α-1,2-mannosidase.

According to the present invention, the nucleotide sequence encoding an α-1,2-mannosidase for introduction into a *Trichoderma* strain can derive from any species. A number of α-1,2-mannosidase genes have been cloned from different species and are available to those skilled in the art, including mammalian genes encoding, e.g., a murine α-1,2-mannosidase (Herscovics et al., 1994), a rabbit α-1,2-mannosidase (Lal et al., 1994) or a human α-1,2-mannosidase (Tremblay et al., 1998), as well as fungal genes encoding, e.g., an *Aspergillus* α-1,2-mannosidase (Eades et al., 1998), a *T. Reesei* α-1,2-mannosidase (Maras et al., 2000), or a *Saccharomyces cerevisiae* α-1,2-mannosidase (Camirand et al., 1991). Protein sequence analysis has revealed a high degree of conservation among the eukaryotic α-1,2-mannosidases identified so far.

Preferably, the nucleotide sequence for introduction into a *Trichoderma* strain encodes a fungal α-1,2-mannosidase, more preferably, a *T. Reesei* α-1,2-mannosidase, and more particularly, the *T. Reesei* α-1,2-mannosidase described by Maras et al., since it is known to also have a broad substrate specificity (Maras et al., 2000; Van Petegem et al., 2001).

According to the present invention, the nucleotide sequence can encode a full length α-1,2-mannosidase or a functional part thereof. By "functional part" is meant a polypeptide fragment of an α-1,2-mannosidase which substantially retains the enzymatic activity of the full-length protein. By "substantially" is meant that at least about 40%, or preferably, at least 50% or more of the full-length α-1,2-mannosidase activity is retained. Those skilled in the art can readily identify and make functional parts of an α-1,2-mannosidase using a combination of techniques known in the art. Predictions of the portions of an α-1,2-mannosidase essential to or sufficient to confer the enzymatic activity can be made based on analysis of the protein sequence. The activity of a portion of an α-1,2-mannosidase of interest, expressed and purified from an appropriate expression system, can be verified using in vitro or in vivo assays.

In accordance with the present invention, an α-1,2-mannosidase or a functional part thereof expressed in a *Trichoderma* strain preferably localizes at a place in the secretory pathway where $Man_{8/9}GlcNAc_2$ (the substrate of α-1,2-mannosidase) is already formed on a glycoprotein, but has not reached the location of the secretion pathway in which resides the phosphomannosyltransferase.

Accordingly, the α-1,2-mannosidase or a functional part thereof is engineered to include an ER-retention signal, such that the protein expressed in a *Trichoderma* strain is targeted to the ER and retains therein for function. "An ER retention signal" refers to a peptide sequence, which directs a protein having such peptide sequence to be transported to and retained in the ER. Such ER retention sequences are often found in proteins that reside and function in the ER. Multiple choices of ER retention signals are available to those skilled in the art, e.g., the first 21 amino acid residues of the *S. cerevisiae* ER protein MNS1 (Martinet et al., 1998). A preferred ER retention signal for use in the present invention is peptide HDEL (SEQ ID NO:34). The HDEL sequence (SEQ ID NO:34) found at the C-terminus of a number of yeast proteins acts as a retention/retrieval signal for the ER (Pelham, 1988). Proteins with an HDEL sequence (SEQ ID NO:34) are bound by a membrane-bound receptor (Erd2p) and then enter a retrograde transport pathway to return from the Golgi apparatus into the ER. According to the present invention, an ER retention signal can be placed anywhere in the protein sequence of an α-1,2-mannosidase, but preferably at the C-terminal end of the α-1,2-mannosidase.

The α-1,2-mannosidase for use in the present invention can be further modified, e.g., by insertion of an epitope tag to which antibodies are available, such as Myc, HA, FLAG and His6 tags which are well-known in the art. An epitope-tagged α-1,2-mannosidase can be conveniently monitored for both expression and intracellular localization. An ER retention signal and an epitope tag can be readily introduced into a protein of interest by inserting nucleotide sequences coding for such signal or tag into the nucleotide sequence encoding the protein of interest, using any of the molecular biology techniques known in the art.

According to the present invention, the nucleotide sequence coding for an α-1,2-mannosidase or a functional part thereof can be placed in an operable linkage to a promoter and a 3' termination sequence.

Promoters appropriate for expression of an α-1,2-mannosidase in a *Trichoderma* strain can include both constitutive promoters and inducible promoters. Constitutive promoters include, e.g., the *Aspergillus nidulans* glyceraldehyde-3-phosphate dehydrogenase promoter ("the gpdA promoter"). Examples of inducible promoters include, e.g., the *T. Reesei* cellobiohydrolase I promoter ("the CBHI promoter").

Transcription termination sequences are sequences 3' to the stop codon of a structural gene which function to stabilize the mRNA transcription product of the gene to which the sequence is operably linked, such as sequences which elicit polyadenylation. Examples of such 3' termination sequences are the *T. Reesei* cellobiohydrolase I terminator ("the CBHI terminator") and the *A. nidulans* indoleglycerolphosphate synthase terminator ("TrypC terminator").

The preferred vector carrying an α-1,2-mannosidase expression sequence is called pFGPDGLAT3-MFMan-HDEL.

Vectors can be introduced into the cells of a *Trichoderma* strain using known methods such as the protoplast technique, described by Penttila et al., 1987. Other published methods useful for transformation of the plasmids or linear vectors include electroporation (Goldman et al., 1990), particle bombardment (Lorito et al., 1993) and an *Agrobacterium tumefaciens*-mediated strategy (de Groot et al., 1998).

During the transformation procedure, the α-1,2-mannosidase expression sequence is cotransformed with a selection plasmid. By "selection plasmid" is meant a plasmid carrying a selection marker. By "selection marker" is meant an expression cassette coding for a specific gene product, which enables us to discriminate between a transformed strain and a non-transformed strain. Transformed *Trichoderma* clones can be selected by using appropriate techniques including but not limited to culturing auxotrophic cells after transformation in the absence of the biochemical product required (due to the cell's auxotrophy), selection for and detection of a new phenotype, or culturing in the presence of an antibiotic which is toxic to the fungus in the absence of a resistance gene within the transformants. Examples of available selection markers for *T. Reesei* are the acetamidase expression cassette of the vector p3SR2 (Hynes et al., 1983) (enabling transformed strains to grow on acetamide as a sole nitrogen source), the *E. coli* hygromycin B phosphotransferase cassette of vector pAN7.1 (Punt et al., 1987) and the *Streptoalloteichus hindustanus* phleomycin-binding protein expression cassette of vector pAN8.1 (Mattern et al., 1988) (enabling the transformed strains to grow on a certain concentration of hygromycin resp. phleomycin).

A further aspect of the invention is a genetically engineered filamentous fungus, expressing a glucosidase II gene according to the invention, further expressing a recombinant N-acetylglucosaminyl-transferase I gene (GlcNAc-transferase I or GnTI). Preferably, the GnTI gene is a human gene. Even more preferably, the GnTI gene is fused to a Golgi localization signal, preferably a Golgi localization signal derived from a protein with SEQ ID NO:4, even more preferably a Golgi localization signal comprising SEQ ID NO:5, even more preferably a Golgi localization signal essentially consisting of SEQ ID NO:5, most preferably a Golgi localization signal consisting of SEQ ID NO:5. Preferably, the filamentous fungus is a *Trichoderma* sp., even more preferably the filamentous fungus is *T. Reesei* Rut-C30.

A GlcNAc-Transferase I is responsible for the addition of β-1,2-GlcNAc to Man$_5$GlcNAc$_2$, and converts this core oligosaccharide on glycoproteins to GlcNAcMan$_5$GlcNAc$_2$. The mannose residues of GlcNAcMan$_5$GlcNAc$_2$ can be further trimmed by a mammalian Golgi mannosidase II. The resulting GlcNAcMan$_3$GlcNAc$_2$ structure can be further elongated with other glycan residues to form hybrid or complex type sugar branches characteristic of mammalian glycoproteins. Thus, by way of introducing a GlcNAc-transferase I into filamentous fungi such as *T. Reesei*, glycoproteins with a mammalian-like or cognate glycoprotein pattern can be produced.

According to the present invention, the nucleotide sequence encoding a GlcNAc-transferase I (GnTI) for use in the expression vector of the present invention can derive from any higher eukaryotic species, e.g., rabbit (Sarkar et al., 1991; SWISS-PROT Accession No P27115), human (Schachter, 1991; SWISS-PROT Accession No P26572), rat (Fukuda et al., 1994; SWISS-PROT Accession No Q09325), plants and insects. Preferably, the nucleotide sequence for use in the present vectors encodes a human GnTI. More preferably, the GnTI gene comprises SEQ ID NO:1, even more preferably, the GnTI gene is essentially consisting of SEQ ID NO:1, most preferably, the GnTI gene is consisting of SEQ ID NO:1.

According to the present invention, the nucleotide sequence can also encode only a functional part of a GlcNAc-Transferase I. By "functional part" is meant a polypeptide fragment of a GlcNAc-Transferase I, which substantially retains the enzymatic activity of the full-length protein. By "substantially" is meant at least about 40%, or preferably, at least 50% or more of the enzymatic activity of the full-length GlcNAc-Transferase I is retained. For example, as illustrated by the present invention, the catalytic domain of the human GnTI constitutes a "functional part" of the human GnTI. Those skilled in the art can readily identify and make functional parts of a GlcNAc-Transferase I using a combination of techniques known in the art. Predictions of the portions of a GlcNAc-Transferase I essential to, or sufficient to confer the enzymatic activity can be made based on analysis of the protein sequence. The activity of a portion of a GlcNAc-Transferase I of interest, expressed and purified from an appropriate expression system, can be verified using in vitro or in vivo assays.

In accordance with the present invention, a GnTI or a functional part thereof expressed in a *T. Reesei* strain preferably is targeted to a site in the secretory pathway where Man$_5$GlcNAc$_2$ (the substrate of GnTI) is already formed on a glycoprotein. Preferably, the GnTI or a functional part is targeted to the Golgi apparatus.

Accordingly, in a preferred embodiment of the present invention, the GnTI is engineered as such that the GnTI or a functional part thereof expressed from the vector is fused with a fungal Golgi localization signal. "A fungal Golgi localization signal" refers to a peptide sequence, which directs a protein having such a peptide sequence to be retained in the Golgi apparatus. Such Golgi localization sequences are often found in proteins that reside and function in the Golgi apparatus. Choices of Golgi localization signals are available to those skilled in the art. A preferred Golgi localization signal for use in the present invention is a peptide derived from the N-terminal part of a *Saccharomyces cerevisiae* Kre2 protein (ScKre2). According to the present invention, a Golgi localization signal can be placed anywhere within the GnTI, but preferably at the terminus of the GnTI, and more preferably at the N-terminus of the GnTI.

The GnTI for use in the present invention can be further modified, e.g., by insertion of an epitope tag to which antibodies are available, such as Myc, HA, FLAG and His6 tags well known in the art. An epitope-tagged GnTI can be conveniently purified, or monitored for both expression and intracellular localization. A Golgi localization signal and an epitope tag can be readily introduced into a protein of interest by inserting nucleotide sequences coding for such signal or tag into the nucleotide sequence encoding the protein of interest, using any of the molecular biology techniques known in the art.

According to the present invention, the nucleotide sequence coding for a GlcNAc transferase I or a functional part thereof can be placed in an operable linkage to a promoter and a 3' termination sequence.

Promoters appropriate for expression of a GlcNAc transferase I in a *Trichoderma* strain can include both constitutive promoters and inducible promoters. Constitutive promoters include, e.g., the *Aspergillus niger* glyceraldehyde-3-phosphate dehydrogenase promoter ("the gpdA promoter"). Examples of inducible promoters include, e.g., the *T. Reesei* cellobiohydrolase I promoter ("the CBHI promoter").

3' termination sequences are sequences 3' to the stop codon of a structural gene which function to stabilize the mRNA transcription product of the gene to which the sequence is operably linked, such as sequences which elicit polyadenylation. Examples of such 3' termination sequences are the *T. Reesei* cellobiohydrolase I terminator ("the CBHI terminator") and the *A. nidulans* indoleglycerolphosphate synthase terminator ("TrypC terminator").

The preferred vector carrying a GlcNAc transferase I expression sequence is called pFGPDKrecohGnTI.

Vectors can be introduced into the cells of a *Trichoderma* strain using known methods such as the protoplast technique, described by Penttila et al., 1987. Other published methods useful for transformation of the plasmids or linear vectors include electroporation (Goldman et al., 1990), particle bombardment (Lorito et al., 1993) and an *Agrobacterium tumefaciens*-mediated strategy (de Groot et al., 1998).

During the transformation procedure, the GlcNAc transferase I expression sequence is cotransformed with a selection plasmid. By "selection plasmid" is meant a plasmid carrying a selection marker. By "selection marker" is meant an expression cassette coding for a specific gene product, which enables us to discriminate between a transformed strain and a non-transformed strain. Transformed *Trichoderma* clones can be selected by using appropriate techniques including but not limited to culturing auxotrophic cells after transformation in the absence of the biochemical product required (due to the cell's auxotrophy), selection for and detection of a new phenotype, or culturing in the presence of an antibiotic which is toxic to the fungus in the absence of a resistance gene within the transformants. Examples of available selection markers for *T. Reesei* are the acetamidase expression cassette of the vector p3SR2 (Hynes et al., 1983) (enabling transformed strains to grow on acetamide as a sole nitrogen source), the *E. coli* hygromycin B phosphotransferase cassette of vector pAN7.1 (Punt et al., 1987) and the *Streptoalloteichus hindustanus* phleomycin-binding protein expression cassette of vector pAN8.1 (Mattern et al., 1988) (enabling the transformed strains to grow on a certain concentration of hygromycin resp. phleomycin).

Another aspect of the invention is a filamentous fungus expressing a recombinant glucosidase II gene, according to the invention, further expressing both a recombinant α-1,2-mannosidase gene and a recombinant GlcNAc-transferase I gene.

Still another aspect of the invention is the use of a genetically modified filamentous fungus, according to the invention, to modulate protein secretion, compared with the parental strain.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 7: (Panel A) cloning of the 5' part of the glsII ORF by inverse PCR; (Panel B) cloning of the 5' part of the glsII ORF by RACE; (Panel C) sequence comparison between the inverse PCR and the 5' RACE fragment reveals the existence of an intron region.

FIG. 14: Probability of coiled coil structure as predicted by the paircoil algorithm. Panel A: predicted coiled coil of GnTI, the maximal probability is 0.36. Panel B: predicted coiled coil of yeast Kre2, maximal probability 0.69.

Figure 1:
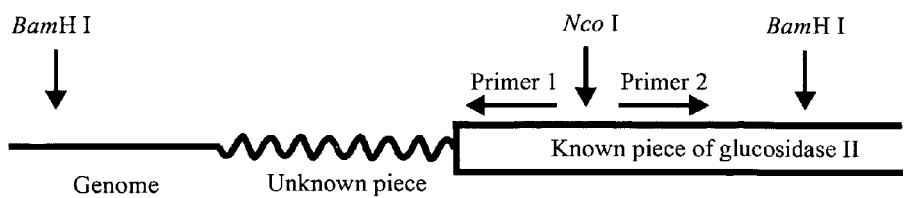
FIG. 1: Schematic overview of the inverse PCR strategy.

FIG. 18: IFNβ-specific Western blot of proteins secreted in the medium by eight BY4742 IFNβ-producing clones (1-8) and eight Y13369 IFNβ-producing clones (A-H). M, marker; WT, non-transformed BY4742 parental strain; KO, non-transformed Y13369 rot2 knock out mutant. The average $OD_{600}$ value of the cultures was 12.56 for the BY4742 transformants and 12.65 for the Y13369 transformants. The upper band is the glycosylated form, the lower band is the not glycosylated form.

FIG. 19: IFNβ-specific Western blot of pooled medium proteins from cultures of eight BY4742 IFNβ-producing clones (WT), eight Y13369 IFNβ-producing clones (KO) and eight Y13369 IFNβ-producing clones supertransformed with pYX132LEUGLSIImut3' (mut). M, marker; C1 and C2, untransformed parental strains. The upper band is the glycosylated form, the lower band is the not glycosylated form.

DETAILED DESCRIPTION OF THE INVENTION

The invention is further explained with the aid of the following illustrative Examples.

EXAMPLES

Materials and Methods

Strains and Transformation Procedure:

Two *T. Reesei* strains were used for the glucosidase II work, being the Rut-C30 (ATCC 56765) and the QM9414 (ATCC 26921) strain. *Trichoderma* transformations were by co-transformation according to Penttila et al. (1987) using the hygromycin resistance gene (plasmid pAN7.1 (Punt et al., 1987)) as a selection marker. Before transformation, the glucosidase II expression vectors pFGPDglsIITreesei and pFG-PDglsIITreeseiMyc were linearized with FspI (Biolabs). Transformants were selected on minimal medium (composition per liter: 20 g dextrose monohydrate, 5 g $(NH_4)_2SO_4$, 15 g $KH_2PO_4$, 0.3 g $CaCl_2$, 0.3 g $MgSO_4$ and mineral components) containing 150 µg/ml of hygromycin.

*T. Reesei* QM9414 was used for the expression of an ER-localized α-1,2-mannosidase. Transformation was by co-transformation according to Penttila et al. (1987) using AmdS (plasmid p3SR2, Hynes et al., 1983) as a selection marker. Before transformation, the α-1,2-mannosidase expression plasmid was linearized with NdeI (Biolabs). Transformants were selected on minimal medium with acetamidase as the sole nitrogen source (composition per liter: 20 g dextrose monohydrate, 15 g $KH_2PO_4$, 0.3 g $CaCl_2$, 0.3 g $MgSO_4$, mineral components, 10 ml 1M acetamidase and 12.5 ml 1M CsCl).

*T. Reesei* QM9414-F4 was used for the expression of a Golgi-localized GlcNAc-transferase I. This strain is a functional α-1,2-mannosidase transformant of strain QM9414. Transformation was by co-transformation according to Penttila et al. (1987) using the phleomycin resistance gene as a selection marker. Before transformation, the GlcNAc-transferase I expression plasmid was linearized with NdeI (Biolabs). Transformants were selected on minimal medium (composition per liter: 20 g dextrose monohydrate, 15 g $KH_2PO_4$, 5 g $(NH_4)_2SO_4$, 0.3 g $CaCl_2$, 0.3 g $MgSO_4$, mineral components) containing 150 µg/ml zeocin (Invitrogen).

For the cloning of the glucosidase II gene and for the construction work, we used electrocompetent resp. chemo-competent *E. coli* MC1061 cells (hsdR2 hsdM+ hsdS+ araD139$_A$(ara leu)$_{7697A}$lac$_{X74}$ galE15 galK16 rpsL (Str$^r$) mcrA mcrB1) (Casadaban et al., 1980). Growth and transformations were as described in Sambrook et al. (1989).

*Saccharomyces cerevisiae* YA-72 (MATa, his3, ura3, leu2) is an IFNβ-producing yeast strain, obtained by transforming the strain CL3-ABYS86 with a GAL1-MF(IS)-IFNβ-CYCT integrative expression cassette (Demolder et al., 1994).

*S. cerevisiae* Y13369 is a rot2 knock out (MATα, his3, leu2, ura3, YBR229c::kanMX4) from BY4742 and was obtained from EUROFAN. The parental strain BY4742 was used as reference.

Yeast strains were transformed using the LiAc method.

Nucleic Acid Preparations from Filamentous Fungi

*Trichoderma* genomic DNA was prepared from five- to six-day-old mycelium, grown in shaker flasks in minimal medium (composition per liter: 20 g dextrose monohydrate, 5 g $(NH_4)_2SO_4$, 15 g $KH_2PO_4$, 0.3 g $CaCl_2$, 0.3 g $MgSO_4$ and mineral components) at 30° C. The mycelium was separated from the growth medium and grinded using liquid nitrogen. 5 to 10 ml of extraction buffer (200 mM Tris.HCl pH 8.5; 250 mM NaCl; 0.5% SDS) was added to resuspend the disrupted *Trichoderma* cells. An equal amount of a phenol/chloroform/isoamyl alcohol mixture (25/24/1) was added to the suspension. After mixing, samples were centrifuged for one hour at 2500 g. The upper phase, containing the DNA, was transferred to a new tube and incubated with 1 mg of RNaseA for 30 minutes at 37° C. Following a new extraction with an equal volume of a mixture of chloroform/isoamyl alcohol (24/1), the upper phase was transferred to a new tube. The DNA was precipitated with half a volume of isopropanol (centrifugation at full speed for 20 minutes at 4° C.). After removing the supernatant, the DNA pellet was washed with 70% EtOH, dried at 37° C. and resuspended in a suitable volume of $H_2O$.

Total *Trichoderma* RNA was prepared from five- to six-day-old mycelium, grown in shaker flasks in minimal medium at 30° C. The mycelium was separated from the growth medium and grinded using liquid nitrogen. Per 0.2 g of mycelium, 1 ml of extraction buffer (25 mM sodiumcitrate; 4 M GuHCl; 100 mM sodium-lauryl sarcosine and 100 mM beta-mercapto-ethanol) was added. The suspension was thoroughly mixed and incubated at 50° C. for 15 minutes. An equal amount of a phenol/chloroform/isoamyl alcohol mixture (25/24/1) was added to the suspension. After mixing, samples were centrifuged for 15 minutes at 9000 g and 4° C. This extraction was repeated twice and followed by a chloroform/isoamyl alcohol (24/1) extraction. After centrifugation (4° C., 9000 g, 15 minutes), the upper phase was collected. One volume of 6 M LiCl was added and the RNA was precipitated overnight at 4° C. After centrifugation (4° C., 9000 g, 15 minutes), the obtained RNA pellet was resuspended in one volume of 3 M LiCl and again precipitated through centrifugation (4° C., 9000 g, 15 minutes). The pellet was resuspended in 400 µl of 0.3 M NaOAc pH 5.7 and incubated at 50° C. for ten minutes. After centrifugation (4° C., 9000 g, 15 minutes), the supernatant was collected. 1 ml of ice-cold EtOH was added and the RNA was precipitated overnight at −20° C. The suspension was centrifuged at 4° C. for 20 minutes and the obtained pellet was washed with 70% EtOH. The dried pellet was resuspended in a suitable volume of DEPC treated $H_2O$.

Cloning of the *Trichoderma* Glucosidase II Gene

Cloning of the glucosidase II alpha subunit was initiated from a *T. Reesei* Rut-C30 cDNA library (Merja Penttila, VTT Biotechnology). In this library, which contains about 100,000 clones, the Rut-C30 cDNA was cloned into an EcoRI/XhoI opened pAJ401 yeast expression vector (Salohelmo et al., 1994).

Based on the alignment of several known mammalian and yeast alpha subunit amino acid sequences, three homologous regions were selected on which degenerate primers were synthesized: the sense primer 5'-GTITATGGIATHCCIGAG-CATGC-3' (SEQ ID NO:6) and the antisense primers 5'-GIGCGTGIGCICKGAAGAAIG-3' (SEQ ID NO:7), and 5'-TGISWICCIGCGAAGAAIGCIC-3' (SEQ ID NO:8), with H=A, C and T; K=G and T; S=G and C; W=A and T. Amplification with primers 1/3 and with primers 1/2 should result in a DNA fragment of approximately 1170 resp. 970 bp. Reaction conditions for the amplification with primers 1/3 were the following: 94° C. for 45 seconds, 55° C. for one minute, 72° C. for 1.5 minutes. Similar reaction conditions were used for the nested PCR, except for the annealing temperature which was decreased to 50° C. Obtained PCR fragments were cloned into pCR2.1-TOPO (Invitrogen) for sequence analysis. TOPO-cloning was done as described by the manufacturer.

As a screening strategy for a bacterial clone containing the *T. reesei* glucosidase II alpha subunit, we used the technique of "Rapid cDNA cloning by PCR screening" (Takumi and Lodish, 1994). In brief, the cDNA library was transformed to *E. coli* MC1061 competent cells. The transformation mixture was diluted and divided into a 96-well plate in a way that every well contained about 5000 cDNA clones. As such, the whole microtiter plate represented about five times the number of cDNA clones within the library. After incubation for several hours at 37° C., a PCR was performed with primers 1 and 3 as described above on cellular mixtures of the 12 columns and the eight rows of the 96-well plate. Based on these results positive wells, lying on the crossing of positive columns and positive rows, could be identified. The cell suspension of one of the positive wells was inoculated into the wells of a new microtiter plate at 500 clones per well. The PCR strategy was repeated and the cell suspension of one of the resulting positive wells was again inoculated into the wells of a new microtiter plate, this time at a concentration of 50 clones per well. By using the PCR strategy, again new positive wells were identified. From one of these wells, the cell suspension was plated on solid Luria Bertani medium. About 200 colonies were transferred to Hybond N filters (Amersham), incubated overnight and analyzed through colony hybridization using the *Trichoderma* glucosidase II-specific 1170 bp PCR fragment as probe. $^{32}$P-labeling of the probe was done using the High-Prime kit (Roche), following the instructions of the manufacturer.

DNA was prepared from several positive clones and digested with EcoRI (Gibco BRL) and XhoI (Gibco BRL) to release the cDNA insert. The glucosidase II specificity of the obtained fragments was checked by southern blotting, using the $^{32}$P-labeled 1170 bp PCR fragment as probe. Also, the obtained fragments were cloned for sequence analysis either as an EcoRI/XhoI fragment into an EcoRI/SalI (Roche) opened pUC19 vector or as a blunted XhoI fragment into an EcoRV (Gibco BRL) opened pBluescriptII KS +/– (Stratagene) vector.

5'-RACE and Inverse PCR

To clone the 5' missing part of the glucosidase II alpha subunit gene, both 5'-RACE and inverse PCR were used. For the inverse PCR (iPCR) strategy, an antisense (5'-GT-TAAACGTTTCGTCCCACC-3') (SEQ ID NO:9) and sense (5'-GGCTCCATCCCTTTCATGC-3') (SEQ ID NO:10) PCR primer were designed, based on the 5' sequence of the cloned but incomplete glucosidase II alpha subunit Rut-C30 cDNA. The 5' end of the primers is facing each other and hybridizes to positions on the cDNA that are separated by 229 bp containing an NcoI restriction site. 10 µg of genomic *Trichoderma* DNA was digested at 37° C. for several hours with 100 units BamHI (Gibco BRL), a restriction enzyme that cuts the cloned cDNA sequence, 3' to both iPCR primers. After heat inactivation of BamHI (ten minutes at 65° C.), the obtained genomic DNA fragments were induced to self-circulate through overnight incubation at room temperature in the presence of 5 units T4 DNA ligase (Roche). Following a phenol extraction and isopropanol precipitation, the DNA was digested with 50 units NcoI (Biolabs) for several hours at 37° C. As such, the desired glucosidase II-containing genomic DNA fragment will be linearized again, enabling the designed iPCR primers (now facing each other with their 3' ends) to hybridize each to one end of the fragment. Following a new phenol extraction and isopropanol precipitation, the DNA was resuspended into 50 µl of H$_2$O. 1 µl of this DNA suspension was used as a template in a PCR reaction with 50 pmol of each iPCR primer. The PCR reaction was performed with cloned Pfu polymerase (Stratagene) in a total volume of 100 µl, and consisted of 20 cycles of 94° C. for 45 seconds; 55° C. for 30 seconds; and 72° C. for 1.5 minutes. A schematic overview of the inversed PCR strategy is shown in FIG. 1.

For the 5'-RACE procedure, we made use of the First Choice™ RLM-RACE strategy kit from Ambion. Primer design and experimental procedure was done on total RNA, following the instructions of the manufacturer. For the outer PCR primer ROT2TR-RLMRACE (5'-GATATACTCGAA-GACGTCGG-3') (SEQ ID NO:11) was used. For the inner PCR, we used primer ROT2TR4_AS (5'-GT-TAAACGTTTCGTCCCACC-3') (SEQ ID NO:9). Annealing during the outer PCR reaction was performed at 57° C.; for the inner PCR, a temperature of 55° C. was used.

The 5'-RACE and inverse PCR fragments were cloned into the pCR-blunt II-TOPO vector (Invitrogen) for sequence analysis, following the instructions of the manufacturer.

Intron and Frame-Shift Analysis Through PCR

The intron-exon composition of the glucosidase II gene was analyzed by amplifying the whole gene from the Rut-C30 genome. 1 µg of gDNA was used as template; the sequence of the sense resp. antisense primer was 5'-ATGAGGTCGAC-GATGGGG-3' (SEQ ID NO: 12) resp. 5'-AGCCAGCT-TGATGCTCC-3' (SEQ ID NO:13). Using Pfu polymerase (Stratagene), following reaction conditions were applied: 25 cycles of 94° C. for one minute, 55° C. for one minute, and 72° C. for seven minutes.

Frame-shift analysis was done by PCR on the Rut-C30 and QM9414 genome. 1 µg of gDNA was used as PCR template. The sequence of the internal glucosidase II-specific primers was 5'-TATCTCTGGTTTCCCGTTCTCG-3' (SEQ ID NO:14) for the sense primer ROT2TR3_S and 5'-CTGGT-CATCAATCGCCAAGCC-3' (SEQ ID NO:15) for the antisense primer ROT2TR0_AS. PCR was performed using Pfu polymerase and following reaction conditions: 25 cycles of 94° C. for one minute, 60° C. for one minute, and 72° C. for one minute.

The PCR fragments were cloned into the pCR-blunt II-TOPO vector (Invitrogen) for sequence analysis, following the instructions of the manufacturer.

Construction of the *Trichoderma* Expression Vector for a Functional *Trichoderma* Glucosidase II Alpha Subunit Gene In a first step, the cloned glucosidase II cDNA fragment was cut out of the pAJ401 library vector as an approximately 3000 bp EcoRI/HindIII (Gibco BRL) fragment. This fragment was ligated into an EcoRI/HindIII opened pUC19 vector, resulting in plasmid pUC19_AglsIITreesei(shift).

In a second step, the frame-shift within the cloned Rut-C30 cDNA fragment was repaired. Using genomic DNA from the QM9414 strain as a template and Pfu polymerase (Stratagene), a PCR reaction was started with primers ROT2TR2-S (5'-ATCAATGAGCAACTCCTGGC-3') (SEQ ID NO:16) and ROT2TR0_AS (5'-CTGGTCATCAATCGCCAAGCC-3') (SEQ ID NO:15). The PCR reaction went on for 25 cycles of one minute at 95° C., one minute at 60° C. and one minute at 72° C. The obtained fragment was digested with XcmI (Biolabs)/PflMI (Biolabs) and ligated into the XcmI/PflMI opened vector pUC19_AglsIITreesei(shift), resulting into the vector pUC19_AglsIITreesei (repaired).

In a third step, the ORF of the glucosidase II alpha subunit was completed: for this the 5' RACE fragment (materials and methods) was digested with DraIII (Biolabs) and MspAI (Biolabs) and ligated into the DraIII/EcoRI-Klenow (Roche) treated vector pUC19_AglsIITreesei (repaired), resulting into the plasmid pUC19glsIITreesei. In a next step, a unique SmaI site was incorporated at the 3' terminus of the glucosidase II ORF through mutagenesis, using the Quick Change Mutagenesis kit from Stratagene. The primer couple used to induce the silent mutation (from CGT to CGG) consisted of a sense primer 5'-CCATGTGAAGGCCCGGGTTGGGGAT-GACTGG-3' (SEQ ID NO:17) and an antisense primer 5'-CCAGTCATCCCCAACCCGGGCCTTCACATGG-3' (SEQ ID NO:18). The resulting plasmid was called pUC19glsIITreesei(SmaI). In a following step, the plasmid was cut EcoRI/SalI for the integration of a linker at the 5' end of the glucosidase II ORF. The linker consisted of two partially complementary primers (sense primer: 5'-GAATTC-CCGCGGTACGTAATTATGAGG-3' (SEQ ID NO:19) and antisense primer: 5'-GTCGACCTCATAATTACGTAC-CGCGGG-3') (SEQ ID NO:20) and was prepared by mixing both primers, boiling the mixture and gradually cooling it to room temperature. By inserting the linker, two new and unique restriction sites (SacII and SnaBI) were integrated at the 5' end of the glucosidase II ORF, creating plasmid pUC19 (5')glsIITreesei(SmaI).

In a next step, this plasmid was opened HindIII/SacII-T4 (Roche) treated and ligated into the HindIII/NcoI (Biolabs)-S1 (Gibco BRL) treated plasmid pFGPDGLAT3 (Contreras et al., 1991). As such the glucosidase II alpha subunit ORF was placed under the transcriptional control of the constitutive *A. nidulans* gpdA promoter. To decrease the distance between the 3' end of the ORF and the TrpC terminator, the vector was digested with MluI (Gibco BRL) to remove a fragment of about 500 bp. The obtained vector fragment was closed by overnight ligation, resulting in the plasmid pFGP-DglsIITreesei. A variant of this plasmid was constructed, containing the *Trichoderma* glucosidase II ORF with a C-terminal Myc-tag. For this, vector pUC19(5')glsIITreesei(SmaI) was digested with SmaI (Gibco BRL) and SnaBI (Biolabs). The resulting fragment containing most of the glucosidase II ORF, was ligated into an NcoI (S1 treated)/Bsp120I (MBI Fermentas) (Klenow treated) opened pFGPDglsIIScMyc vector.

Using this construction strategy, the ten C-terminal amino acids of the *Trichoderma* glucosidase II were replaced by the coding sequence for the Myc-tag. In the resulting vector, called pFGPDglsIITreeseiMyc, the ORF coding for the Myc-tagged *Trichoderma* glucosidase II alpha subunit is under the transcriptional control of the constitutive *A. nidulans* gpdA promoter and the TrpC terminator. Plasmid pFGPDglsIISc-Myc was constructed for the expression of the *S. cerevisiae* glucosidase II alpha subunit in *T. Reesei*. This vector was constructed as follows: by a PCR strategy using plasmid pGAPZglsIIScMyc as DNA template, Pfu polymerase, sense primer ROT2ScNco_S 5'-CTTGCCATGGTC-CTTTTGAAATGGCTC-3' (SEQ ID NO:21) and antisense primer ROT2ScMycHind_AS 5'-CCCAAGCTTCTACA-GATCCTCTTCTGAGATGAG-3' (SEQ ID NO:22), we amplified a Myc-tagged version of the *S. cerevisiae* glucosidase II gene. The PCR reaction consisted of 30 cycles of 45 seconds at 94° C., 45 seconds at 50° C. and eight minutes at 72° C. Since the nucleotide sequences of the NcoI and HindIII restriction sites were incorporated in the sense resp. antisense primer, the obtained PCR fragment was easily cloned into an NcoI/HindIII opened pFGPDGLAT2 vector, resulting into plasmid pFGPDglsIIScMyc. Vector pGAPZglsIIScMyc was constructed for the expression of the *S. cerevisiae* glucosidase II ORF in *Pichia pastoris* (PCT International Patent Application WO0200856). Genomic DNA was prepared from the *S. cerevisiae* strain InvSC1 (α, leu2-3, 112 his3Δ1, trpl-289, ura3-52) (Invitrogen) using the Nucleon kit (Amersham). This was used as template for the amplification of the glucosidase II alpha subunit with sense primer ROT2Sc_S 5'-CCGCTCGAGATGGTCCTTTTGAAATGGCTC-3' (SEQ ID NO:23) (containing the sequence for a unique XhoI restriction site) and antisense primer ROT2Sc_AS 5'-CCGGGCCCAAAAATAACTTCCCAATCTTCA-3' (SEQ ID NO:24) (containing the sequence for a unique ApaI restriction site).

Figure 2A:
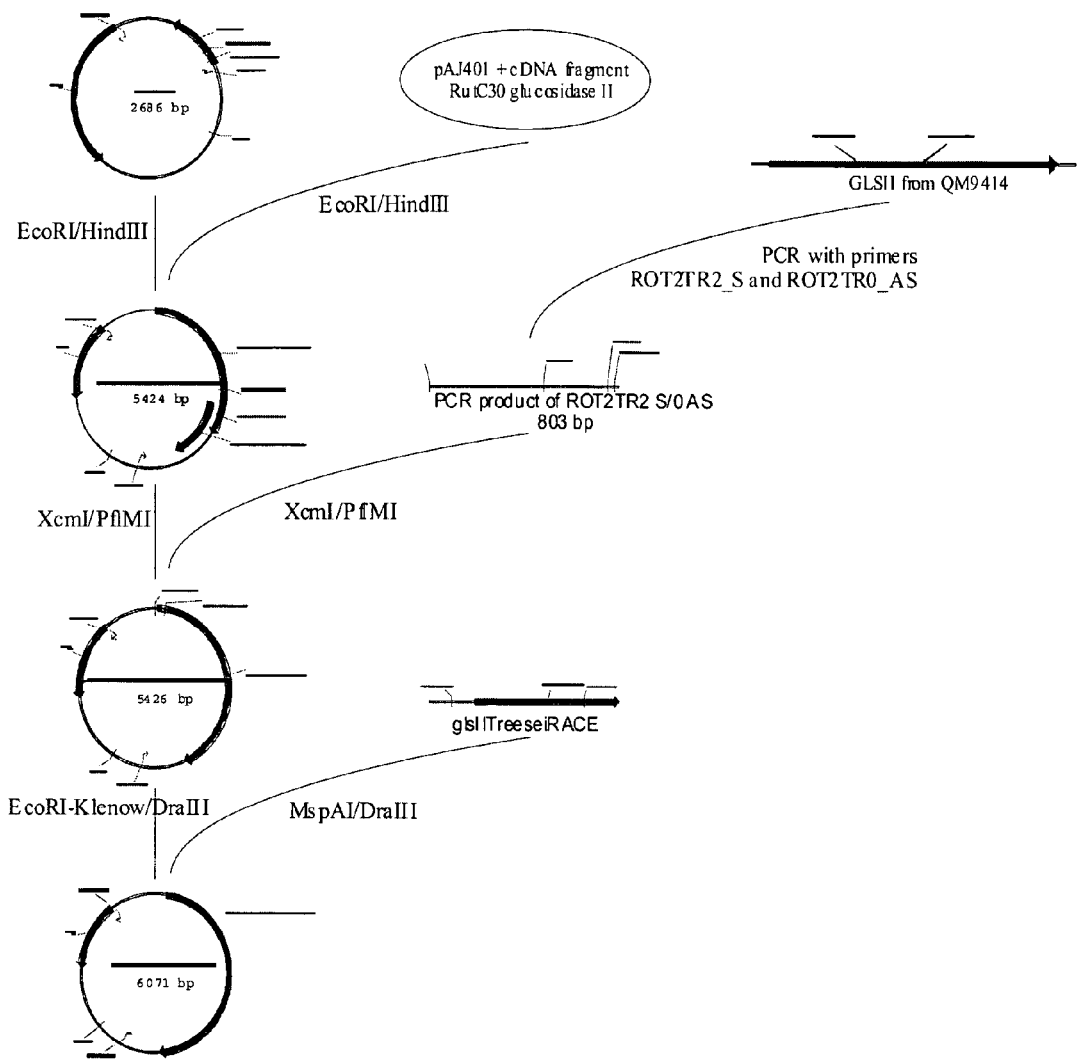
FIG. 2: Construction strategy for the glucosidase II expression plasmids pFGPDglsIITreesei and pFGPDglsIITreesei-Myc.
Figure 2B:
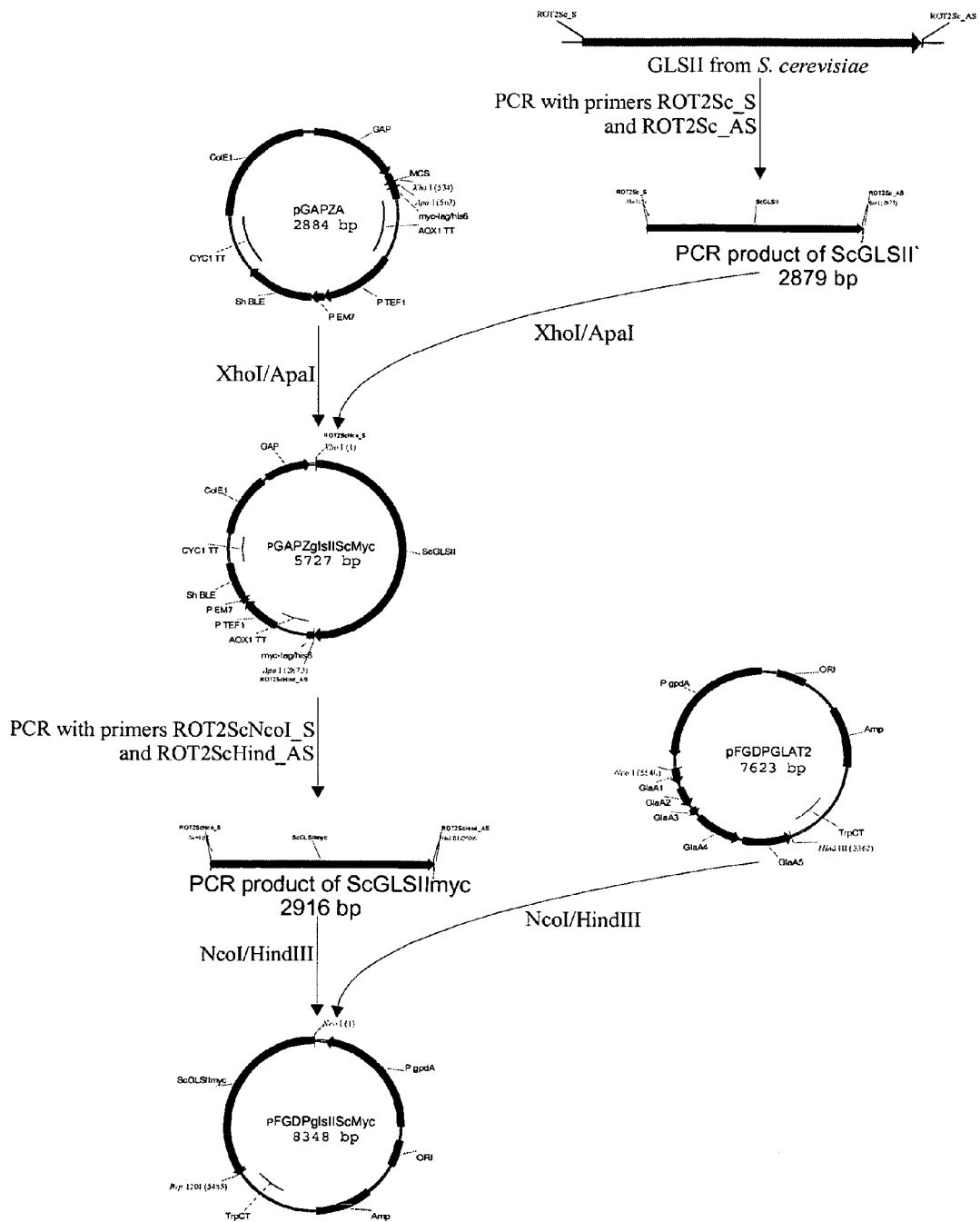
Figure 2C:
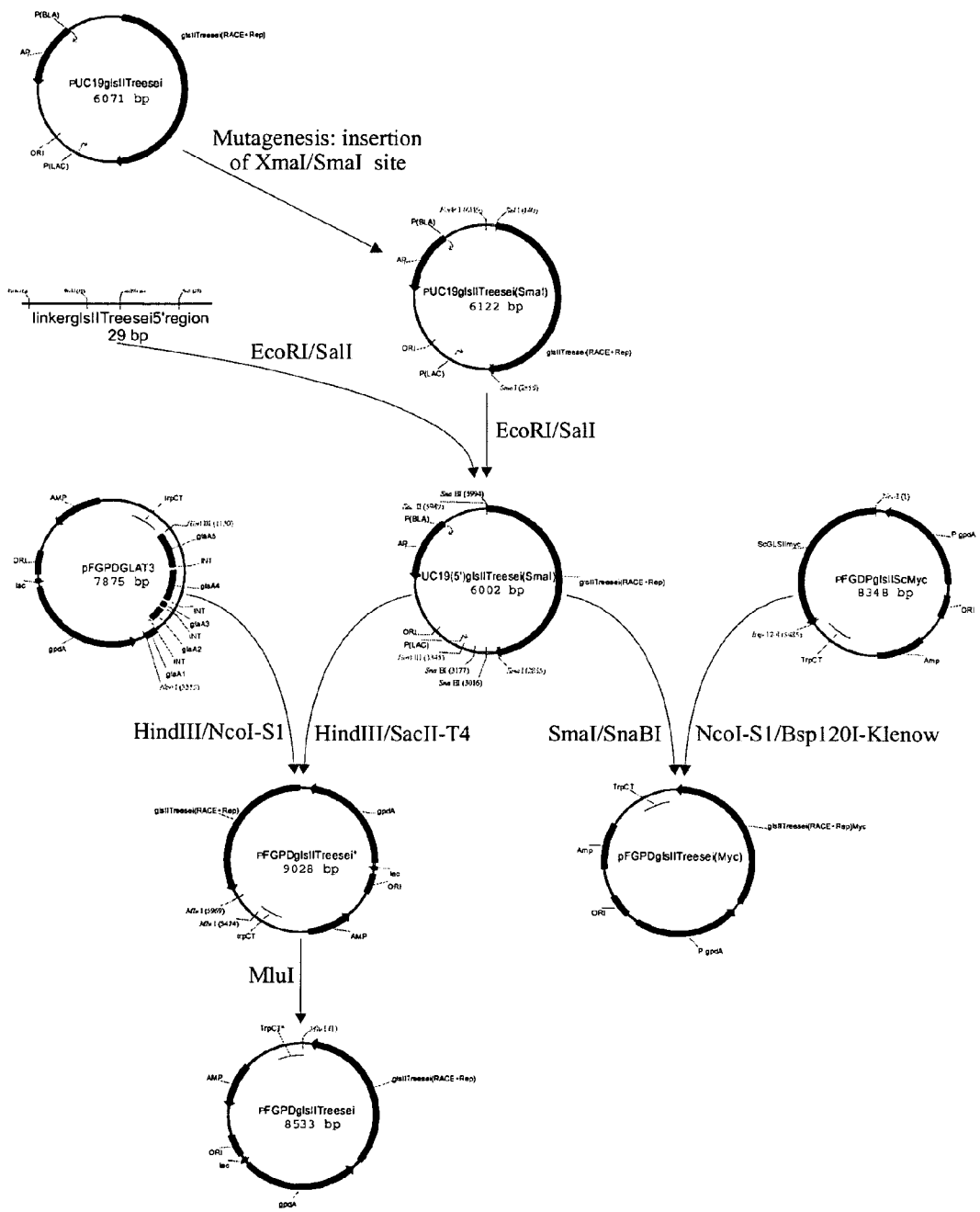

Amplification was performed by a touch-down PCR strategy using LA TaKaRa polymerase (TaKaRa Shuzo co., LTD.) with following conditions: three cycles of 30 seconds at 94° C., two seconds at 98° C., 30 seconds at 65° C. and ten minutes at 70° C.; three cycles of 30 seconds at 94° C., two seconds at 98° C., 30 seconds at 60° C. and ten minutes at 70° C. and 30 cycles of 30 seconds at 94° C., two seconds at 98° C., 30 seconds at 55° C. and ten minutes at 70° C. After digestion with ApaI (Biolabs)/XhoI (Gibco BRL), the fragment was ligated into an ApaI/XhoI opened pGAPZ,A vector (Invitrogen), to allow in frame cloning of the amplified glucosidase II ORF with a nucleotide sequence coding for the Myc-tag. The resulting plasmid was called pGAPZglsIISc-Myc. An overview of the construction strategy can be seen in FIG. 2.

Figure 11:
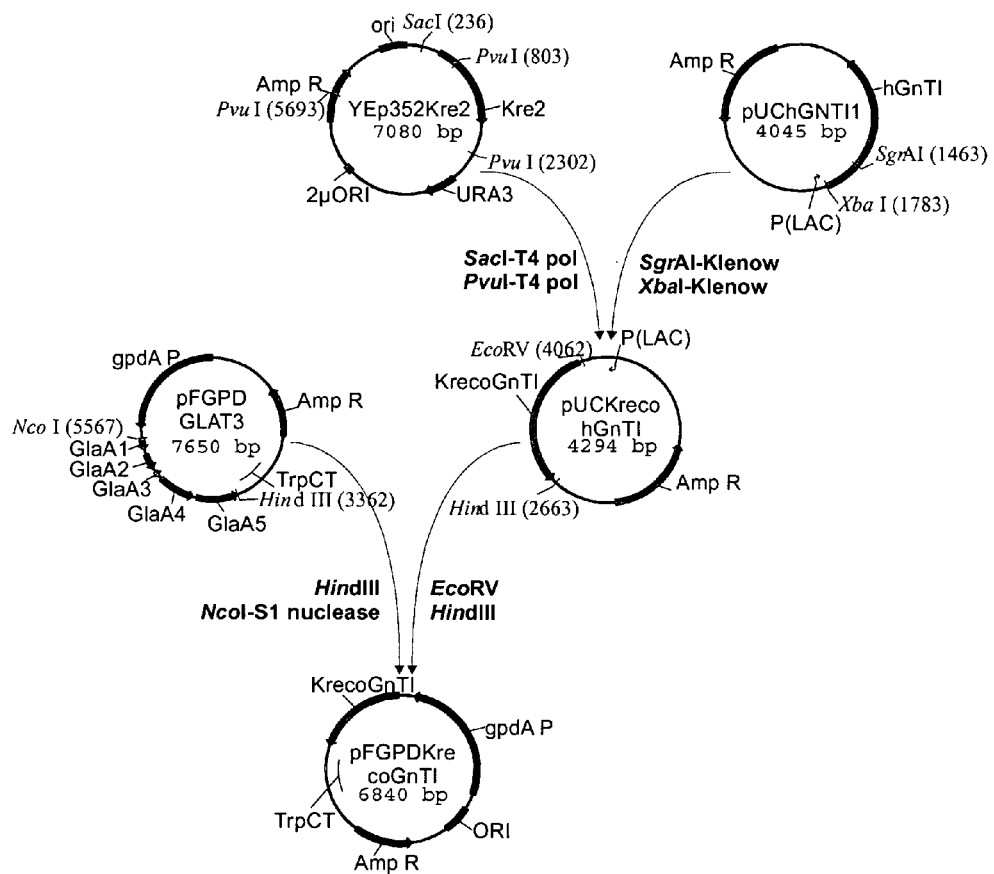
FIG. 11: Construction strategy for the GlcNAc transferase I expression plasmid pFGPDKrecoGnTI.

Construction of the α-1,2-mannosidase and GlcNAc-Transferase Expression Plasmids For the expression of an ER-localized variant of the *T. Reesei* α-1,2-mannosidase in *T. Reesei* Rut-C30-g31, the α-1, 2-mannosidase coding part was isolated from plasmid pGAPZMFManHDEL. This plasmid contains the mannosidase with the N-terminal prepro-signal sequence of the *S. cerevisiae* α-mating factor and a C-terminal HDEL-tag (SEQ ID NO:34) as described in Callewaert et al. (2001b). The mannosidase part was isolated by a BstBI (Biolabs)/NotI (Biolabs) digest. The BstBI sticky end was blunted with T4-polymerase (Roche). The obtained fragment was ligated in an NcoI (Biolabs) (Mung Bean nuclease (Roche) blunted)/ NotI opened pFGPDGLAT3 (Contreras et al., 1991) vector. The resulting plasmid pFGPDGLAT3-MFManHDEL contains the α-1,2-mannosidase ORF under the transcriptional control of a constitutive gpdA promoter. An overview of the construction scheme is presented in FIG. 11.

In order to target more efficiently the human GlcNAc-transferase I to the fungal Golgi apparatus, the GnTI N-terminal part was replaced by the *S. cerevisiae* Kre2 N-terminal sequence, known to be responsible for protein retention in the yeast Golgi (Lussier et al., 1995). Plasmid pFGPDKrec-oGnTI was constructed as follows. Plasmid YEp352Kre2

(kindly provided by Dr. Howard Bussey, McGill University, Montreal, Canada), which contains the Kre2 gene as a SacI/ PvuII fragment cloned in a SalI(Klenow blunted)/SacI opened YEp352 vector, was digested with SacI (Biolabs)/ PvuI (Gibco BRL) and T4-polymerase (Roche) blunted. The 5' end region of the gene was isolated and cloned in a Klenow blunted SgrAI (Roche)/XbaI (Gibco BRL) opened pUCh-GnTI vector (Maras et al., 1997). By doing so, the coding sequence of the Golgi localization signal of the yeast Kre2 protein was cloned in frame with the nucleotide sequence of the catalytic domain of the GlcNAc transferase I protein. The resulting ORF was isolated by performing an EcoRV (Gibco BRL)/HindIII (Gibco BRL) double digest and was cloned into an NcoI (S1-nuclease (Gibco BRL) blunted)/HindIII opened pFGPDGLAT3 vector, as such creating the plasmid pFGPDKrecoGnTI. The construction of the expression plasmid is presented in FIG. 11.

Genomic Analysis

For the analysis of the glucosidase II transformants, genomic DNA was digested overnight with 50 units of NheI (Biolabs) and KpnI. After electrophoresis, the DNA was transferred to a Hybond N+ membrane (Amersham). Integration of the expression plasmid into the genome was checked, by hybridizing the Hybond filter with a $^{32}$P-labeled glucosidase II-specific probe. Labeling of the probe was done using the High Prime kit (Roche). The DNA template for the labeling reaction consisted of a part of the glucosidase II ORF and was obtained through an NcoI digest on plasmid pFGPDglsIITreesei.

A similar strategy was followed after digestion of the genomic DNA with 50 units of DraIII and BglII (Biolabs). This time however, the Southern blot was screened with a probe which is derived from an EcoRI/NheI fragment of vector pFGPDglsIITreesei and which hybridizes against the gpdA promoter sequence of the glucosidase II expression plasmid.

For the analysis of the α-1,2-mannosidase transformants, genomic DNA was digested overnight with 50 units BglII (Promega) and NotI (Promega). After electrophoresis, the DNA was transferred to a Hybond N+ membrane (Amersham). Integration of the expression plasmid into the genome was checked by hybridizing the Hybond filter with a $^{32}$P-labeled α-1,2-mannosidase-specific probe. Labeling of the probe was done using the High Prime kit (Roche). The DNA template for the labeling reaction consisted of a part of the gpdA promoter and was obtained through an EcoRI (Promega)/NheI (Biolabs) digest on plasmid pFGPDGLAT3-ManHDEL. Integration was also checked by PCR on 1 µg gDNA using Taq polymerase (MBI Fermentas). A gene-specific antisense primer hybridizing against the 3' region of the mannosidase gene (5'-CAACTCGTCGTGAGCAAGG-3') (SEQ ID NO:25), and a sense primer that hybridizes against the gpdA promoter region of the expression vector (5'-CCATATTTTCCTGCTCTCCC-3') (SEQ ID NO:26), were used for the amplification reaction. The PCR conditions were as follows: 30 cycles of one minute at 94° C., one minute at 60° C. and two minutes at 72° C.

For the analysis of the GlcNAc-transferase I transformants, genomic DNA was digested overnight with 50 units BglII (Promega). After electrophoresis, the DNA was transferred to a Hybond N+ membrane (Amersham). Integration of the expression plasmid into the genome was checked, by hybridizing the Hybond filter with a $^{32}$P-labeled GlcNAc transferase I-specific probe. Labeling of the probe was done using the High Prime kit (Roche). The DNA template for the labeling reaction consisted of a part of the GlcNAc transferase I ORF and was obtained through a BglII/NcoI digest on plasmid pFGPDKrecoGnTI.

Construction of the *S. cerevisiae* Plasmids pSCGALMFHIFNB2 is an IFNβ expression construct where the IFNβ coding sequence is placed under control of the GAL promoter (Demolder et al., 1994).

The 3' end of the ROT2 gene was isolated by PCR reaction using 5'-TACGGGCCCGGGAAAAAAACGAAGT-GATATC-3' (SEQ ID NO:27) as sense primer and 5'-CCT-TGTCGAGGTGGGAAATGTCC-3' (SEQ ID NO:28) as antisense primer. The PCR conditions used were 95° C. for three minutes; 94° C. for one minute; 55° C. for one minute; 72° C. for one minute; 25 cycles of 72° C. for ten minutes; cool down to 4° C. The resulting fragment was cloned into pCR2.1-TOPO (Invitrogen Co, Carlsbad, Calif., USA) to yield pCR2.1-TOPO3'ROT2.

pGAPADE1glsII was constructed as follows: the glucosidase II ORF of *S. cerevisiae* was amplified from the gDNA of strain INVSc (α leu2-3, 112 his3Δ1, trpl-289, ura3-52) (Invitrogen). gDNA was prepared from an overnight grown yeast culture in YPD at 30° C. DNA was prepared using the Nucleon Kit for extraction of yeast gDNA (Amersham). The sense primer for the PCR amplification hybridizes to the 5' part of the yeast ORF (including the ATG start coding) and contains a XhoI restriction site for easier downstream cloning work. The antisense primer hybridizes against the 3' part of the ORF (but not including the stop codon) and contains an ApaI site for easier downstream cloning. The sequence of both primers is as follows: sense primer ROT2(S): 5'-CCGCTCGAGATGGTCCTTTTGAAATGGCTC-3' (SEQ ID NO:23) and antisense primer ROT2(AS): 5'-CCGGGCCCAAAAATAACTTCCCAATCTTCAG-3' (SEQ ID NO:29). PCR was done via a touch-down strategy using LA TaKaRa (ImTec Diagnostics) on 200 ng gDNA, using 50 pmol of each primer. The amplification was obtained during three rounds of 94° C. for 30 seconds, 98° C. for two seconds, 65° C. for 30 seconds, 70° C. for ten minutes; followed by three similar PCR rounds, however, this time with an annealing temperature of 60° C., followed by 30 similar PCR rounds, however this time using an annealing temperature of 55° C.

A fragment of the expected length of 2900 bp was obtained via this PCR strategy and was XhoI/ApaI ligated into a XhoI/ApaI opened pGAPZA (Invitrogen). The resulting vector was called pGAPZAglsII and carries the *S. cerevisiae* glucosidase II alpha subunit under the transcriptional control of the *Pichia* GAP promoter. pGAPZAglsII was cut with NsiI,T4/PinAI to isolate a fragment containing the GAP promoter and glsII ORF. The obtained fragment was ligated into a SalI/PinAI opened pBLADE 1X' plasmid creating vector pGAPADE1glsII. Vector pBLADE 1X' was a kind gift from Dr. Benjamin Glick (Department of Molecular Genetics and Cell Biology, University of Chicago, USA) (Sears et al., 1998).

pCR2.1-TOPO3'ROT2 was cut with SalI EcoRI and treated with 1 µl T4 (Boehringer Mannheim) with 1 µl dXTP (10 mM) and 1 µl of appropriate buffer for one hour at 37° C. The resulting fragment plasmid was cloned into a T4 treated SalI cut pGAPADE1glsII to yield pGAPADE1glsII3'binv.

A 1222 bp SphI SnaBI URA3 gene fragment of *S. cerevisiae* was cloned into SphI Eco RV opened pGAPADE1glsII3'binv to give pKOROT2.

pGAPADE1glsII3' binv was used as template to introduce the *T. reesei* mutation in the *S. cerevisiae* glucosidase II gene. The mutagenesis was carried out using 5'-GTAGGATC- CTCGCAAAGCC-3' (SEQ ID NO:30) as mutation sense primer and 5'-GACAATTACATTGAGGAAAGATCCG-3' (SEQ ID NO:31) as mutation antisense primer. The reaction mixture consisted of 80 μl H$_2$O, 10 μl buffer with (NH$_4$)$_2$SO$_4$—MgCl$_2$, 6 μl MgCl$_2$, 2 μl dXTP (10 mM), 1 μl mutation sense primer (100 pmol/μl), 1 μl mutation antisense primer (100 pmol/μl), 0.5 μl template DNA and 0.5 μl Taq DNA polymerase. The reaction conditions used were 95° C. for two minutes, 94° C. for one minute, 54° C. for one minute, 72° C. for one minute, 24 cycles (from step 2), 72° C. for ten minutes, cool down until 4° C.

The mutant fragment was reintroduced in pGAPADE1glsII3'binv as a BamHI XcmI fragment and the resulting plasmid was called pGAPADE1GLSIImut3'.

The T4 polymerase treated EcoO109I fragment, which contains a LEU2 ORF, of the plasmid YipUTYL was cloned into a T4 treated DraIII/XbaI cut pYX132 to yield pYX132LEU.

The vector pYX132 was purchased from Ingenius (R&D Systems Europe, Abingdon, UK). The vector YipUTYL was taken form the LMBP plasmid collection (LMBP 3871).

pGAPADE1GLSIImut3' was cut with EcoRI and treated with T4 polymerase, and the GLSII mutant-containing fragment was cloned into a cip treated SmaI opened pYX132LEUste. The resulting plasmid was called pYX132LEUglsIImut3'.

N-Glycan Analysis

Transformants were grown for six days at 30° C., in 100 ml shaker flasks containing 50 ml minimal medium with glucose, lactose or cellulose as single carbon source (composition per liter: 20 g dextrose monohydrate or lactose or Solca Floc cellulose, 5 g (NH$_4$)$_2$SO$_4$, 15 g KH$_2$PO$_4$, 0.3 g CaCl$_2$, 0.3 g MgSO$_4$ and mineral components). N-glycans of the total pool of secreted proteins were prepared according to Papac et al. (1998) from 1 ml of growth medium. The final glycan pellet was resuspended into 5 μl of bidest H$_2$O. 1 μl of this glycan preparation was used for oligosaccharide analysis by DSA-FACE, as described recently (Callewaert et al., 2001).

Mild acid hydrolysis of the N-glycans was performed on 1 μl of the prepared N-glycan mixture by incubation with 9 μl 10 mM HCl at 100° C. for 30 minutes. Before DSA-FACE analysis, the sample was dried and the pellet resuspended into 1 μl bidest H$_2$O. In vitro α-1,2-mannosidase and β-N-Acetylglucosminidase digestions were done overnight at 37° C. on 1 μl of the prepared N-glycan mixture in 20 mM NaOAc pH 5.0. As enzyme source, in house produced T Reesei α-1,2-mannosidase (Maras et al., 2000) and Jack Bean derived hexosaminidase (Glyko) were used. Before DSA-FACE analysis, the sample was dried and the pellet resuspended into 1 μl bidest H$_2$O.

Analysis of Secreted Protein

Using Shaker Flask Cultures:

T. Reesei RutC30 WT and transformant g14, expressing a full-size copy of the T. Reesei glucosidase II alpha subunit, were grown for six days at 30° C., in 100 ml shaker flasks containing 50 ml of minimal medium with glucose as single carbon source (composition per liter: 20 g dextrose monohydrate, 5 g (NH$_4$)$_2$SO$_4$, 15 g KH$_2$PO$_4$, 0.3 g CaCl$_2$, 0.3 g MgSO$_4$ and mineral components). After growth, the mycelium was separated from the medium and dried overnight at 50° C. Total extracellular protein of a fraction of the growth medium was TCA precipitated. The volume for the different samples taken for the precipitation of the total protein, was normalized against the dry weight of the mycelium. The precipitated proteins were resuspended in loading buffer and analyzed by SDS-PAGE. Gels were stained using coomassie brilliant blue (Sigma).

Using Steady-State Growth Conditions:

T. Reesei strains QM9414, Rut-C30 and its glucosidase II alpha subunit transformant Rut-C30-g31 were grown in steady-state/chemostat conditions. Briefly, the strains were grown at 28° C. with a dilution rate of 0.05 h$^{-1}$. The culture medium consists of 8 g/l lactose, 3.75 g/l KH$_2$PO$_4$, 5.7 g/l (NH$_4$)$_2$SO$_4$, 0.17 g/l CaCl$_2$.2H$_2$O, 0.375 g/l MgSO$_4$.7H2O and 1 ml/L of a trace element solution consisting of 3.7 g/l CoCl$_2$, 5 g/l FeSO$_4$.7H$_2$O, 1.4 g/l ZnSO$_4$.7H$_2$O and 1.6 g/l MnSO$_4$.7H$_2$O. The pH was kept constant at 5.5: adjustments were done automatically with 0.1 N KOH. Foaming was controlled by a mixture of polypropylene glycols. Samples of the chemostat culture were taken at regular time-intervals. Total cellulase activity was measured with para-Nitrophenyl-β-D-lactopyranoside as a substrate and compared to a standard curve of T. Reesei cellulases (Sigma). 1 unit releases 1 mmol op para-Nitrophenol per hour at 37° C. Total protein concentration was measured using the Bradford assay, with T. Reesei cellulases from Sigma as standard protein.

Analysis of the Transformants by Lectin Screening

Transformants were grown for six days at 30° C., in 100 ml shaker flasks containing 50 ml minimal medium with glucose as single carbon source. 1 ml of growth medium was used to precipitate the secreted proteins with trichloroacetic acid. Proteins were separated by SDS-PAGE and blotted onto nitrocellulose membranes, using standard techniques (Sambrook et al., 1989).

The nitrocellulose membrane was blocked with TNT-buffer (50 mM Tris.HCl pH 7.5; 150 mM NaCl; 0.1% TWEEN®-20) for one hour and washed briefly in lectin buffer (50 mM Tris.HCl pH 7.5; 150 mM NaCl; 0.05% TWEEN®-20; 1 mM MgCl$_2$; 1 mM CaCl$_2$; 1 mM MnCl$_2$). Afterwards, the membrane was incubated for two hours with a biotinylated Griffonia simplicifolia II lectin, which is specific for terminal GlcNAc (EY laboratories, Inc.). The lectin was diluted in lectin buffer according to the specifications of the provider. The membrane was washed twice (15 minutes in lectin buffer) and incubated for one hour in lectin buffer with streptavidin conjugated to peroxidase (Roche). After two wash steps (15 minutes in lectin buffer), the peroxidase was detected using the Renaissance® chemiluminescence kit (NEN™ Life Science). Luminescent signals were captured either using the Lumi-imager™ F1 apparatus from Boehringer Mannheim or on an X-ray film.

IFNβ Western Blots

Western blots were carried out as described by Redlich and Grossberg (1989) and Grossberg et al., 1986.

IFNβ secretion was tested on a 15% polyacrylamide gel. The primary antibody as an anti-human IFNβ monoclonal antibody (Chemicon International, Temecula, Calif., USA). The secondary antibody was a goat anti-mouse HRP-conjugated monoclonal anti-IgG1 antibody (Apovia). Visualization was carried out using a Western Lighting Chemiluminescence Reagent Plus kit (Perkin Elmer Life Sciences, Boston, Mass., USA).

Bio-Informatics

Conversion of nucleotide sequences into amino acid sequences was done using the Translate Tool at worldwideweb.us.expasy.org/tools/#translate. Homology searches were done using the BLAST algorithm at worldwideweb.ch.embnet.org/software/BottomBLAST.html (Altschul et al., 1990). Dual and multiple alignments were performed using the Clustal W algorithm (Thompson et al., 1994) at worldwideweb.ebi.ac.uk/clustalw, resp. the Align program (GENESTREAM network server IGH, Montpellier FRANCE) at worldwideweb2.igh.cnrs.fr/bin/align-guess.cgi (Pearson et al., 1997). General features of the protein (MW, pI, Amino acid composition, . . . ) were assessed using the ProtParam Tool at worldwideweb.us.expasy.org/tools/protparam.html. The presence of a putative signal sequence was predicted using Signal P (version 1.1) at worldwideweb.cbs.dtu.dk/services/SignalP. Prediction of the presence of transmembrane helices was done using the TMHMM (version 2.0) program at worldwideweb.cbs.dtu.dk/services/TMHMM-2.0 or the HMMTOP (version 2.0) program (by G. E. Tusnady) at worldwideweb.enzim.hu/hmmtop. All above-mentioned tools are either local or accessible via a link on the ExPASy (Expert Protein Analysis System) proteomics server from the Swiss Institute of Bioinformatics (SIB) (Appel et al., 1994).

Example 1

Figure 3:
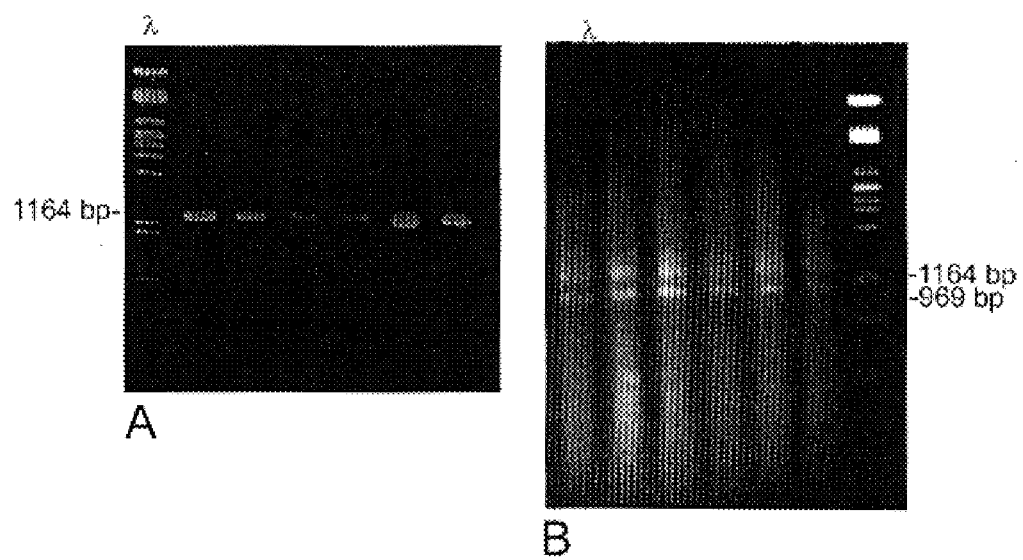
FIG. 3: (Panel A) PCR on Rut-C30 cDNA library using degenerate primers 1 and 3. (Panel B) nested PCR on Rut-C30 cDNA library using degenerate primers 1, 2 and 3.

Cloning of the *T. reesei* Glucosidase II Alpha Subunit Gene cDNA Cloning of the Glucosidase II Alpha Subunit Using the ClustalW algorithm website, an alignment was made between the amino acid sequences of the *S. cerevisiae* glucosidase II and the several known mammalian glucosidase II alpha subunits. Based on several homologous regions, three degenerate primers were designed to screen a cDNA library of the *T Reesei* Rut-C30 strain (VTT Biotechnology). Amplification using sense primer 1, antisense primer 3 and the cDNA library as template DNA, resulted into a fragment of the expected size of 1170 bp (FIG. 3, Panel A). Nested PCR amplification including antisense primer 2, resulted in an extra DNA fragment with an expected length of about 970 bp (FIG. 3, Panel B). Both fragments were cloned in the TOPO-TA vector pCR2.1-TOPO (Invitrogen) for sequence analysis. By homology search, the obtained nucleotide sequences proved to be glucosidase II specific.

Figure 4:
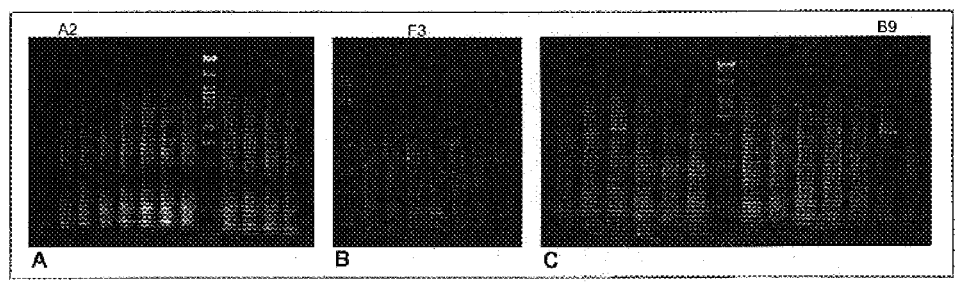
FIG. 4: PCR screening with degenerate primers 1 and 3: (Panel A) first round with about 5000 clones per well; (Panel B) second round with about 500 clones per well; (Panel C) third round with about 50 clones per well. The cell suspension from well A2 was used for the second PCR round; the cell suspension from well F3 was used for the third PCR round and the cell suspension from well B9 was used for colony hybridization analysis.
Figure 5:
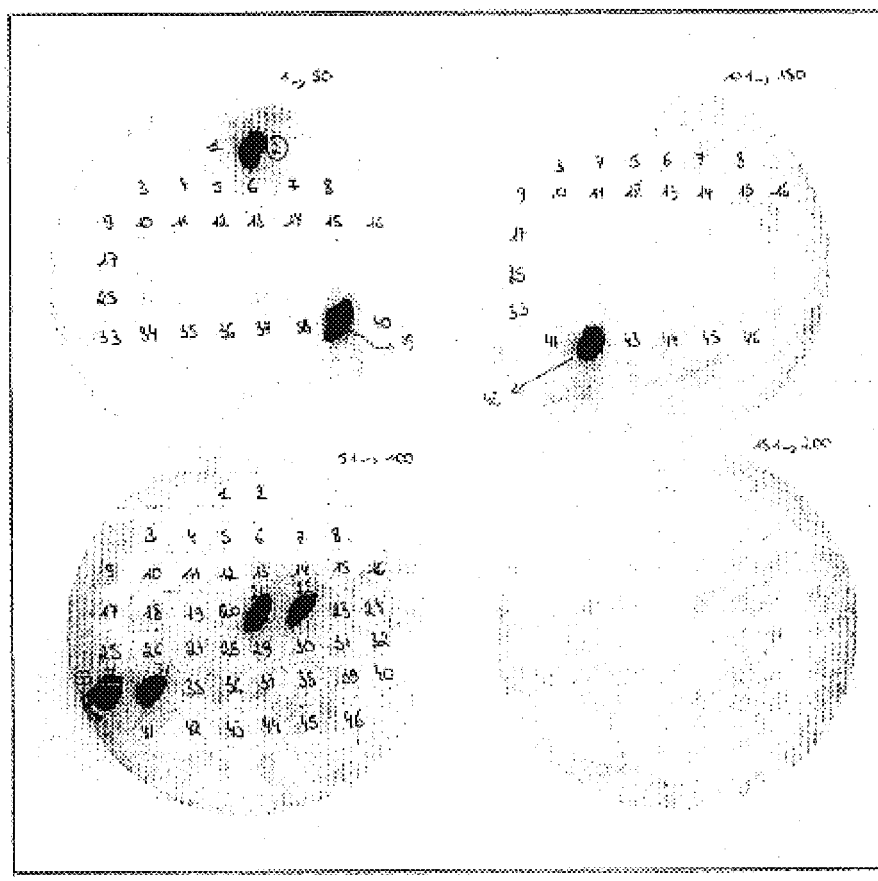
FIG. 5: results of the colony hybridization.
Figure 6:
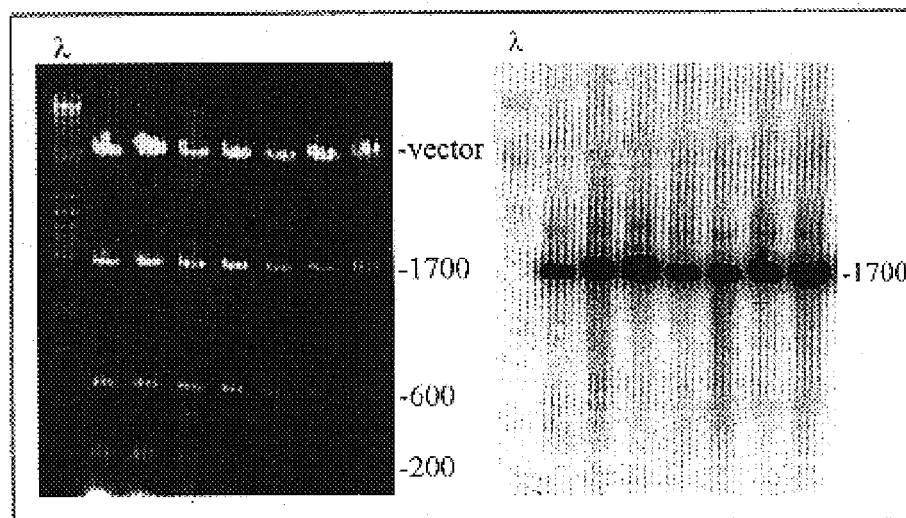
FIG. 6: plasmid DNA of the seven positive clones was prepared and digested with XhoI/EcoRI to isolate the cDNA insert. Hybridization analysis indicates that at least the 1700 bp fragment is glucosidase II specific.

Based on this knowledge, cloning of the glucosidase II alpha subunit cDNA was started from the Rut-C30 cDNA library, using the technique of "cDNA cloning by PCR screening" (Takuma and Lodish, 1994). The PCR analysis was performed using sense primer 1 and antisense primer 3. Each PCR round (three in total) indicated that several wells within the microtiter plate contained at least one glucosidase II-specific clone (FIG. 4). In the final PCR round each well contained a cell suspension of about 50 different cDNA clones. Two of these wells proved to be positive during the PCR screening. A dilution of the cell suspension of one of those wells was plated on solid Luria Bertani medium. About 200 colonies were streaked on filters for colony hybridization. Using a $^{32}$P labeled probe, we identified seven positive clones (FIG. 5). DNA of the seven clones was prepared and analyzed through a XhoI/EcoRI digestion. Fragments of about 1700 bp, 600 bp and 200 bp were obtained and proved to be glucosidase II specific either by southern hybridization (FIG. 6) or by sequence analysis after cloning into pUC19 or pBluescript II KS +/−. The completely cloned cDNA fragment consisted of 2290 bp. Homology analysis indicated that a substantial part of the 5' end of the ORF was missing.

Cloning of the 5' Coding Sequence of the Glucosidase II Alpha Subunit

Both an inverse PCR strategy and a 5' RACE strategy were initiated to clone the missing part. Through inverse PCR on Rut-C30 genomic DNA, a 1700 bp fragment was obtained (FIG. 7, Panel A) and cloned into the pCR2.1-TOPO vector. Partial sequence analysis indicated the presence of two fragments showing homology to the 5' part of the ORF of other known glucosidase II genes. The two glucosidase II homologous regions were separated from each other by a 60 bp sequence, containing features that are specific for intron sequences in filamentous fungi. The existence of an intron at the 5' end of the *Trichoderma* glucosidase II sequence was further confirmed by a 5' RACE strategy. Using the "First Choices™" RLM-RACE kit (Ambion) we obtained an 1138 bp fragment (FIG. 7, Panel B) missing the 60 bp intron sequence, but otherwise showing a 100% homology to the already cloned iPCR fragment (FIG. 7, Panel C).

Intron Analysis

To evaluate the intron-exon composition of the *Trichoderma* glucosidase II alpha subunit gene, a PCR was performed on genomic Rut-C30 DNA using 5' and 3' genespecific primers. Amplification resulted into a fragment of about 3000 bp, which is close to the length of the coding cDNA. This indicated that only a few rather small introns could be present. Alignment of the PCR fragment with the cloned cDNA showed that the 60 bp intron at the 5' terminus was the only intron present within the glucosidase II alpha subunit gene. The small size of this intron is consistent with sizes of most other characterized introns in filamentous fungi (May et al., 1987; Martinez-Blanco et al., 1993; Takaya et al., 1994). The intron follows the GT/AG rule for the 5' and 3' splice site (Mount, 1982). Thirteen nucleotides upstream of the 3' splice site, the intron contains a lariat sequence of the consensus CTRAC (with R=purine), which is characteristic for other fungal introns (Hiraoka et al., 1984; Orbach et al., 1986; May et al., 1987).

Frame-Shift Analysis

The DNA sequencing data of the 5' RACE fragment and the cloned cDNA sequence were put together, resulting in a 3621 bp fragment. Translation and BLAST analysis indicated the presence of an ORF showing homology to known glucosidase II alpha subunits. The glucosidase II ORF encodes a polypeptide of 807 amino acids. Contrary to the first 655 amino acids, the C-terminal 152 amino acids do not show any considerable sequence homology to other known glucosidase II alpha subunits. On top of that, the *Trichoderma* glucosidase II polypeptide sequence is significantly smaller compared to the yeast or mammalian homologue. This indicated the presence of a frame-shift within the cloned cDNA, resulting into a premature abrogation of translation. Indeed, computer analysis of the 3' 1500 bp of the 3621 bp fragment showed the presence of an out-of-frame sequence of 927 bp encoding a polypeptide of 309 amino acids, which shows high homology to the C-terminus of known glucosidase II alpha subunits.

Using two glucosidase II internal primers ROT2TR3-S and ROT2TR0_AS, a fragment of about 320 bp was amplified from the genomic DNA of *T. Reesei* Rut-C30 and QM9414. Based on the BLAST homology searches, the annealing sites of the two primers were chosen so that the amplified fragment should contain the site of the frame-shift. Sequence alignment of the two PCR fragments clearly indicates the presence of a frame-shift in the Rut-C30 genome, which was not found within the QM9414 genome: at position 1965 of the glucosidase II alpha subunit ORF a "T" is missing. As such, a premature stop codon, 459 nucleotides 3' of the position of the frame-shift, results in a truncated protein with 153 C-terminal amino acids that are not specific to the *Trichoderma* glucosidase II alpha subunit. This mutation within the Rut-C30 genome could very well explain the difference in glycosylation pattern when comparing the Rut-C30 strain with other *T. Reesei* strains.

General Features of the Cloned Gene

The knowledge of the nature of the mutation within the glucosidase II alpha subunit gene enabled us to put together some general data on the *Trichoderma* glucosidase II. A full-size non-mutant ORF of 2892 bp encodes a polypeptide of 964 amino acids, which is about the expected length based on data from other known glucosidase II alpha subunits. The protein has a calculated molecular weight of 109.858 Dalton and a theoretical pI of 5.6. Analysis using Signal P (version 1.1) indicated the presence of a putative eukaryotic signal sequence of 30 amino acids. A signal cleavage site was predicted after $Leu_{29}Ala_{30}$. Analysis of the mature polypeptide sequence with the TMHMM (version 2.0) and the HMMTOP (version 2.0) program did not reveal the presence of transmembrane helices. The polypeptide sequence also seems to lack any known ER-retention signal such as an HDEL tag (SEQ ID NO:34). These data are in agreement with the general model for the glucosidase II protein: the alpha subunit is the catalytic partner of a heterodimer that is retained within the ER by interacting with the beta subunit, which carries an ER retention signal. The *T. Reesei* glucosidase II alpha subunit has the highest sequence homology (64.2% identity) to the *Neurospora crassa* counterpart, while the sequence identity with the *Saccharomyces cerevisiae* homologue is only 37.9%. On the other hand, sequence identity with *Schizosaccharomyces pombe* and higher eukaryotic organisms like pig, human and *Arabidopsis thaliana* is resp. 43.1, 40.9, 40.4 and 40.1%.

Example 2

Expression of a Fully Active *Trichoderma* Glucosidase II Alpha Subunit in the Rut-C30 Strain Construction of a *Trichoderma* Glucosidase II Alpha Subunit Expression Plasmid and Transformation to Rut-C30

A *T. Reesei* expression vector encoding a functional variant of the Rut-C30 glucosidase II alpha subunit was prepared. In a first step, the frame-shift within the cloned cDNA fragment was repaired. In a next step, the 5' RACE fragment and the repaired cDNA were ligated to one another to obtain a full length ORF, encoding a full size and functional alpha subunit. In a last step, the ORF was placed under the transcriptional control of the constitutive gpdA promoter and the TrpC terminator resulting in the vector pFGPDglsIITreesei. Using a second strategy, a similar vector was created in which the ten C-terminal codons of the ORF were replaced by the coding sequence of the Myc-tag, resulting in vector pFGPDglsII-TreeseiMyc.

Both plasmids were transformed to *T. Reesei* Rut-C30 as described by Penttila et al. (1987) using pAN7.1 as selection plasmid (Punt et al., 1987). Transformants were selected on their resistance to hygromycin. After two rounds of clone purification, single clones were obtained.

Analysis of the Transformants

The initial analysis of the transformants was based on the functionality of the expressed glucosidase II alpha subunit. For that, transformants were initially grown for six days in 50 ml glucose minimal medium, after which the N-glycan profile of the pool of total secreted protein was analyzed. N-glycans were prepared from 0.25 to 1 ml of growth medium as described by Papac and coworkers (1998) and analyzed by DSA-FACE (Callewaert et al., 2001a). The N-glycan profiles of the QM9414 strain, which does not carry monoglucosylated N-glycans (Garcia et al., 2001), and the RutC30 WT strain were analyzed in the same way and compared with that of the selected transformants.

Figure 8:
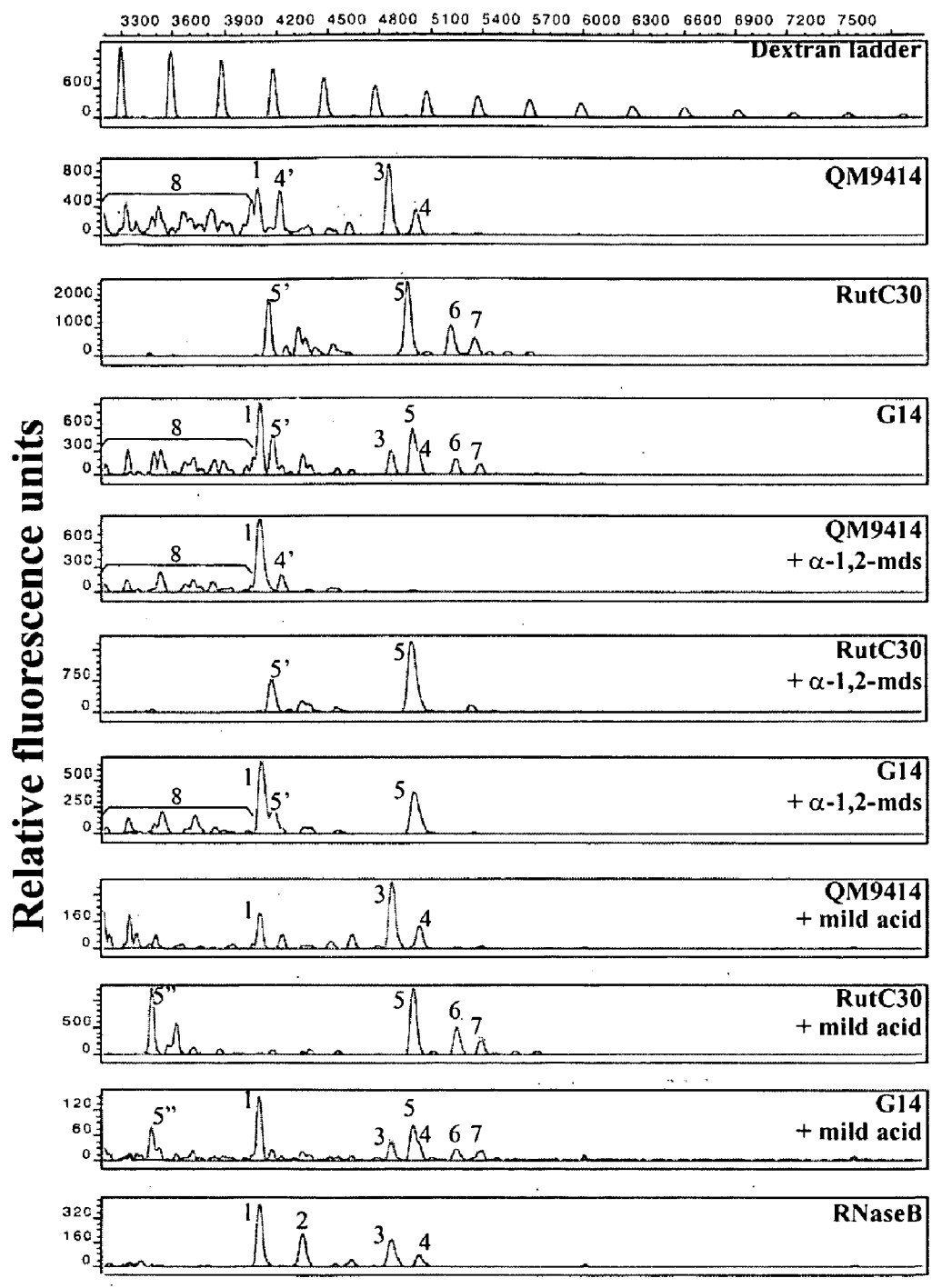
FIG. 8: Glycosylation profile of the RutC30, QM9414 and g14 transformants, either native, after α-1,2-mannosidase digestion or after mild acid hydrolysis. For all three cases it is clear that the g14 transformant has a glycosylation profile that contains characteristics of both the RutC30 and the QM9414 strains. The deduced N-glycans are numbered: 1, $Man_5GlcNAc_2$; 2, $Man_6GlcNAc_2$; 3, $Man_8GlcNAc_2$; 4, $Man_9GlcNAc_2$; 5, $GlcMan_7GlcNAc_2$; 6, $GlcMan_8GlcNAc_2$; 7, $GlcMan_9GlcNAc_2$; 3', $ManPMan_8GlcNAc_2$; 4', $ManPMan_9GlcNAc_2$; 5', $ManPGlcMan_7GlcNAc_2$; 5", $PGlcMan_7GlcNAc_2$.

Based on the published structural data of the most predominant oligosaccharides synthesized on secreted cellobiohydrolase I (De Bruyn et al., 1997, Maras et al., 2000), the profile of the RutC30 strain appeared relatively easy to interpret. An in vitro α-1,2-mannosidase digestion was used to characterize the peaks representing monoglucosylated high-mannose glycans. Since the α-1,3-linked glucose blocks the hydrolysis of the two underlying α-1,2-linked mannose residues, a maximum of two mannoses can be released from the glycan substrate, resulting in $GlcMan_7GlcNAc_2$. Mild acid hydrolysis, which hydrolyzes phosphodiester linkages, was used to characterize the peaks representing phosphorylated high-mannose carbohydrates. Release of the phosphate-coupled mannose results in a phosphomonoester glycan, which carries an extra negative charge and as such has a higher electrophoretic mobility. Peaks representing these glycans are shifted to the left side of the DSA-FACE profile. As such, using a combination of an α-1,2-mannosidase digestion and a mild acid hydrolysis, the most predominant peaks within the DSA-FACE glycan pattern of the RutC30 strain could be assigned to $GlcMan_{7-8}GlcNAc_2$ and their charged counterparts $ManPGlcMan_{7-8}GlcNAc_2$ (FIG. 8).

A similar analysis was performed on the glycan pattern of QM9414. Initially, the QM9414 DSA-FACE profile looks far more complex. However, comparison with the standard profile of RNase B indicates that a significant fraction of the glycan pool consists of $Man_{5-9}GlcNAc_2$. This was confirmed via an in vitro digestion with α-1,2-mannosidase. Moreover, mild acid hydrolysis of the carbohydrates indicates that most of the peaks at the left hand side of the $Man_5GlcNAc_2$ signal represent glycans containing one or more phosphodiester linkages. As such, the QM9414 glycan peaks could be assigned to neutral and phosphorylated high-mannose N-glycans. The distribution of the phosphorylated N-glycans is not severely changed after α-1,2-mannosidase digestion, since the phosphodiester linkages form a steric hindrance for the enzyme or block the access to underlying α-1,2-linked mannose residues (FIG. 8).

In a next step, the N-glycan profile of several hygromycin-resistant transformants was analyzed. Only one of the analyzed transformants (g14) shows a clear difference in its N-glycan pattern, compared to the RutC30 WT strain. The g14 glycan pool looks more heterogeneous and closer examination indicates that it consists of a combination of the RutC30 and the QM9414 carbohydrate profile (FIG. 8). Especially at the left hand side of the $Man_5GlcNAc_2$ peak, a lot of new peaks emerge representing fast migrating oligosaccharides. Since most of them are susceptible to mild acid hydrolysis, we believe that they represent a structural diversity of phosphorylated high-mannose glycans, analogous to the situation in QM9414. In combination with these charged high-mannose N-glycans, some peaks representing neutral unglucosylated carbohydrates also emerge in the DSA-FACE profile. The presence of these structures was further confirmed by performing an in vitro α-1,2-mannosidase digestion. Comparison of the g14 with the RutC30 profile however, clearly indicates that still a significant amount of monoglucosylated glycans (neutral and charged $GlcMan_{7-9}GlcNAc_2$) is synthesized on the proteins of the transformed strain. Presumably, the amount of full-size glucosidase II is not sufficient to hydrolyze all α-1,3-linked glucose residues.

A number of hygromycin-resistant transformants, including g14, and the WT RutC30 strain were analyzed on the genomic level. To clearly discriminate between endogenous mutant alpha subunit locus and the repaired cDNA from the integrated expression vector, genomic DNA was digested with KpnI/NheI (NheI cuts within the gpdA promoter of the expression vector) and analyzed via Southern blot using a glucosidase II-specific probe. Using this strategy, two bands of approximately 5000 and 3400 bp were visualized for the g14 transformant, the latter one resulting from a random integration of the alpha subunit expression cassette into the *T. Reesei* genome. For all other transformants showing no change in their N-glycan profile, only the fragment of about 5000 bp was identified. This is identical to the band obtained for the untransformed RutC30 strain and as such can only result from a hybridization event to the endogenous locus encoding the truncated GIIα.

Effect of the Overexpression of the Glucosidase II Alpha Subunit on the Secretion Capacity of the Transformants The *T. Reesei* RutC30 strain, which is a hypersecretor of cellulases, synthesizes unusual N-glycan structures on its secreted proteins. Thorough analysis indicated that most of the oligosaccharides carries α-1,3-glucose residues (Maras et al., 1997). These capping structures, which prevent further trimming of the glycans by α-1,2-mannosidase, are probably the result of an inefficient glucosidase II activity. Several events may cause this phenomenon: (1) the glucosidase II simply cannot cope with the rich load of protein passing through the secretion pathway during cellulase-inducing conditions; (2) during the consecutive rounds of mutagenesis leading to this hypersecretor strain, one or more mutations have occurred within the glucosidase II gene or its transcriptional elements.

Surprisingly, we found that restoration of the glucosidase II activity affects the secretion capacity that is similar to that of the wild-type strain. Transformant g14, where both glucosidase II forms are expressed, shows a secretion capacity that is significantly lower than that of the hypersecreting stain RutC30, clearly indicating that the glucosidase II plays an important role in the level of secretion.

Example 3

Expression of α-1,2-mannosidase in *Trichoderma*

In order to localize most of the recombinant α-1,2-mannosidase to the ER compartment, where it can act on the substrate $Man_8GlcNAc_2$ to deliver a $Man_5GlcNAc_2$ structure, an HDEL-tag was added at the C-terminal end of the protein. By doing so, the recombinant protein is recycled in a COP I depended manner from the Golgi apparatus to the ER due to binding to the HDEL-receptor.

An expression cassette containing the constitutive gpdA promoter, the prepro-signal sequence of the yeast α-mating factor for directing the protein into the secretory pathway, the HDEL-tagged α-1,2-mannosidase ORF and the trpC terminator was constructed. The construct was transformed using AmdS (acetamidase) as a selection marker. Transformants were selected for their ability to grow on minimal medium with acetamide as a sole nitrogen source. The transformants were submitted to several selection rounds in order to get single or "pure" clones.

Figure 12:
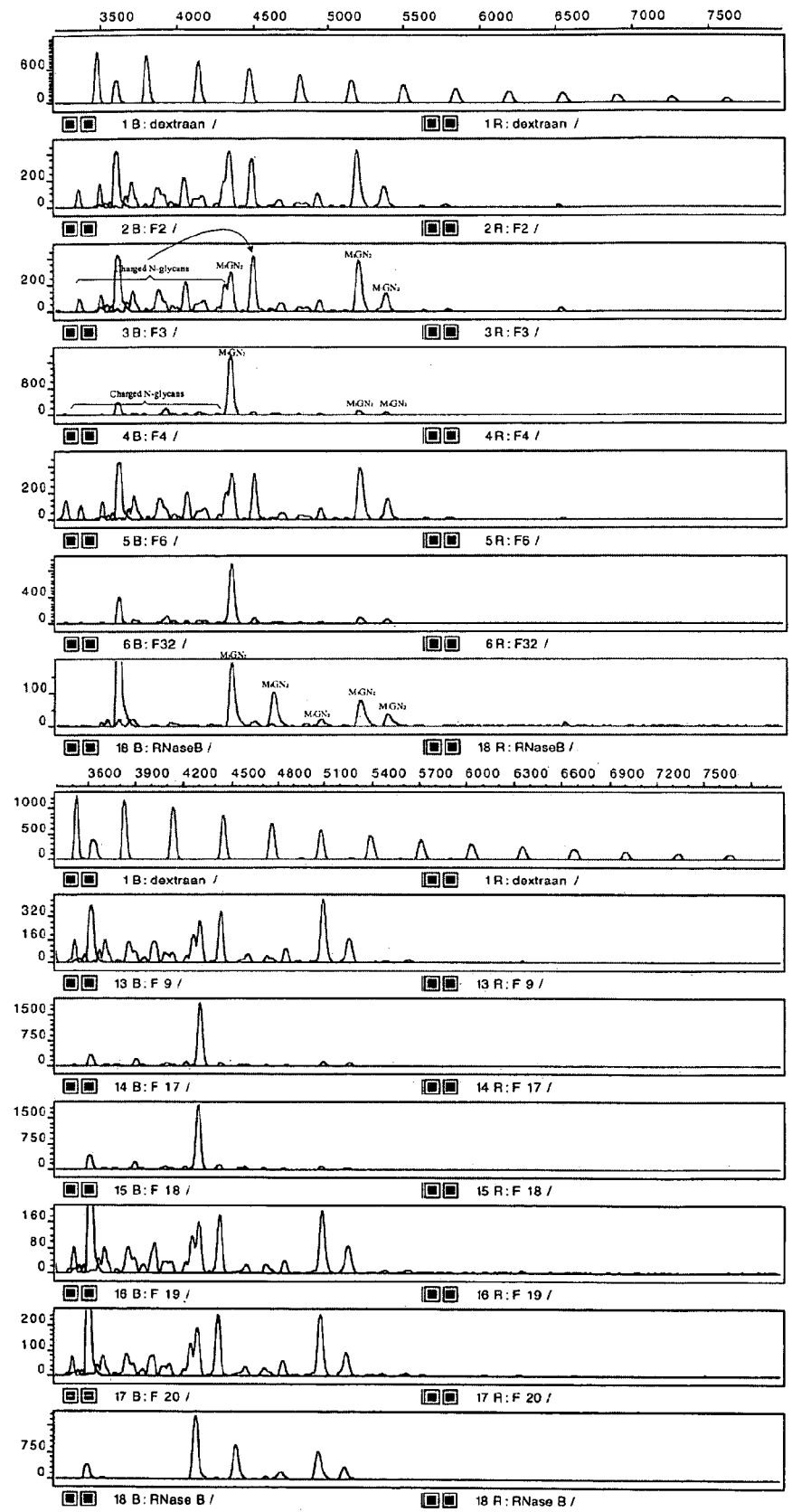
FIG. 12: N-glycan analysis of several transformants capable of growing on acetamide as single N-source: transformants F4, F17, F18 and F32 almost exclusively synthesize $Man_5GlcNAc_2$ as a result of the expression of an ER-localized α-1,2-mannosidase.
Figure 13:
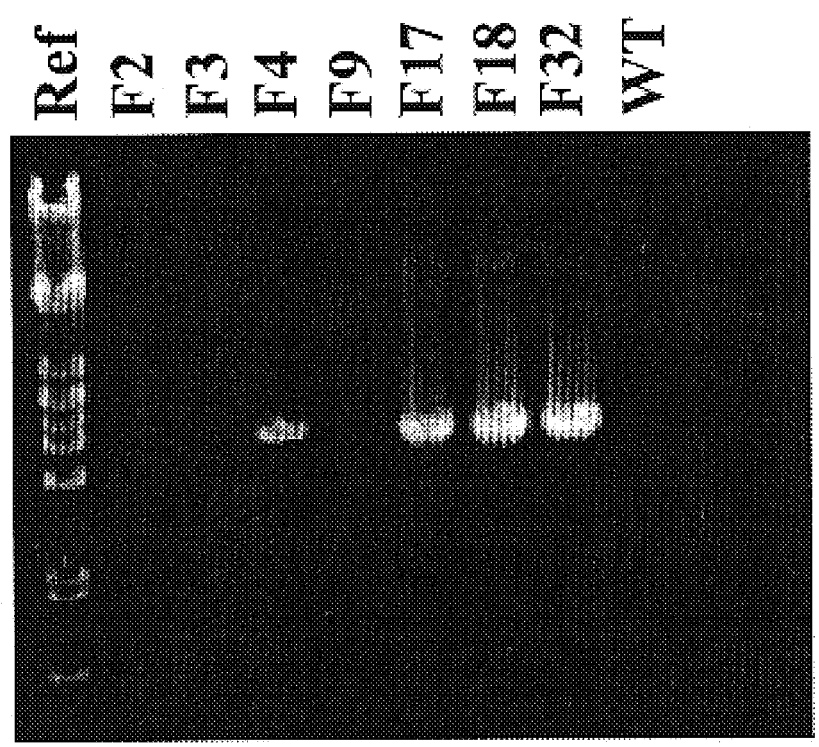
FIG. 13: PCR analysis of the genomic DNA of a few acetamide-resistant *Trichoderma* clones: Transformants F4, F17, F18 and F32 score positive for the PCR analysis.

To assess the functionality of the ER-localized α-1,2-mannosidase, the N-glycan profile of the total pool of secreted protein was analyzed. For this, transformants were grown in glucose-containing minimal medium as described in materials and methods. N-glycans were released from 1 ml of growth medium through the method described by Papac et al., 1998. The results from the DSA-FACE analysis are depicted in FIG. 12. In total, 16 transformants were analyzed by DSA-FACE, of which four had the expected $Man_5GlcNAc_2$ glycan pattern. Evidence for the presence of the mannosidase expression plasmid in the genome of the transformants was obtained by Southern blotting/PCR analysis. Only a very small amount of the total glycan pool consists of $Man_{6-9}GlcNAc_2$, some of them carrying mannosephosphate. An additional in vitro digestion with purified recombinant α-1,2-mannosidase almost completely converts the remnant neutral high-mannose N-glycans to $Man_5GlcNAc_2$.

When grown in glucose minimal medium, the total amount of secreted cellulases is rather low. To evaluate the trimming capacity of the ER-localized α-1,2-mannosidase during cellulase inducing conditions, one of the positive transformants (transformant F4) was grown in minimal medium with 2% lactose, 5% lactose or SolcaFloc cellulose as C-source instead of 2% glucose. N-glycan analysis was as described in materials and methods. When comparing the N-glycan profiles from the different growth conditions, we found almost no difference. This suggests that the recombinant α-1,2-mannosidase is expressed in sufficient amounts to deal with a large flow of protein within the secretory pathway.

The results clearly indicate that the ER localization of a functional α-1,2-mannosidase enables the fungus to convert most of the ER high-mannose structure $Man_{8-9}GlcNAc_2$ to $Man_5GlcNAc_2$. By doing so, phosphomannosylation of the N-glycans is almost completely abolished. It seems that in the untransformed strain, the phosphomannosyltransferase and the α-1,2-mannosidase compete for the same high-mannose oligosaccharides. The obtained $Man_5GlcNAc_2$ structure is no substrate for the phosphomannosyltransferase, which is in accordance with data published for the *S. cerevisiae* Mnn6p transferase protein (Wang et al., 1997). This also suggests that the *Trichoderma* phosphomannosyltransferase activity is located somewhat further in the secretion pathway (medial to trans Golgi).

In conclusion, the obtained results indicate that by using this strategy, we can convert the fungal-type N-glycosylation pattern of *T. Reesei* to almost exclusively $Man_5GlcNAc_2$. Since this is the substrate for the GlcNAc transferase I, the key enzyme in the synthesis of complex N-glycans, new possibilities in creating a *Trichoderma* strain with a more human-like glycan profile can be explored.

Example 4

Expression of GlcNAc-Transferase in *Trichoderma*

For GlcNAc-transferase I to be localized to the Golgi compartment, where it can act on the $Man_5GlcNAc_2$ structure, two chimeras were created in the past between the C-terminal part of GlcNAc-transferase I and the N-terminal part of yeast Kre2, a Golgi localized mannosyltransferase (Lussier et al., 1995). The fusion positions were based on the fact that both proteins contain a putative coiled coil that might be important for localization and oligomerization of the protein. Indeed, when the respective amino acid sequences were analyzed by the paircoil program (Berger et al., 1995), a coiled coil was predicted from amino acid 49 to 81 in GlcNAc-transferase I with a probability of 0.36 and from amino acid 54 to 99 in Kre2 with a probability of maximum 0.69 (see also FIG. 14). In addition, when analyzing the GlcNAc transferase I of other organisms, the probability of the presence of a coiled coil structure was even higher. Based on results obtained in

*Aspergillus niger*, plasmid pFGPDKrecoGnTI encoding a chimer of the first 100 amino acids of Kre2 and the C-terminal part of GlcNAc-transferase I starting from amino acid 103 (as such having the coiled coil of Kre2), was preferred for the expression of recombinant human GlcNAc transferase I in *T. Reesei*.

The construct was cotransformed to the α-1,2-mannosidase expressing transformant F4 of strain QM9414. The *Streptoalloteichus hindustanus* phleomycin-binding protein expression cassette was used as selection marker. Transformants were selected based on their capacity to grow on minimal medium containing zeocin. The transformants were submitted to several selection rounds in order to get single or "pure" clones.

To identify functional GlcNAc-transferase II transformants a first screening round was performed using the *Griffonia simplicifolia* II lectin, which is specific for terminal GlcNAc residues. Several transformants were grown for six days on glucose minimal medium.

Transformants that score positive during the lectin screening were further analyzed by DSA-FACE. N-glycans were released from 1 ml of growth medium through the method described by Papac et al., 1998. Changes in the glycosylation profile that could indicate the functional expression of GlcNAc transferase I were investigated by in vitro digestion of with Jack Bean hexosaminidase (Glyko): strains of which the pattern returned to the $Man_5GlcNAc_2$ profile after the in vitro digestion, proof to be the desired glycosylation transformants.

Example 5

Effect of the Overexpression of the Glucosidase II Alpha Subunit on the Secretion Capacity of the Transformants The *T. Reesei* RutC30 strain contains a frame-shift mutation in the glucosidase II alpha subunit gene, resulting in the production of a partially defective gene product. To restore the normal ER-processing of protein-linked N-glycans, this strain was transformed with the expression plasmid pFGP-DglsIITreesei (FIG. 2), containing the full-size *Trichoderma* glucosidase II alpha subunit (GIIα) gene under the transcriptional control of the constitutive gpdA promoter. Transformation was done according to Penttila and coworkers (1987). Vector pAN7.1 (Punt et al., 1987) was co-transformed to enable selection of the transformants on hygromycin-containing medium.

Figure 9:
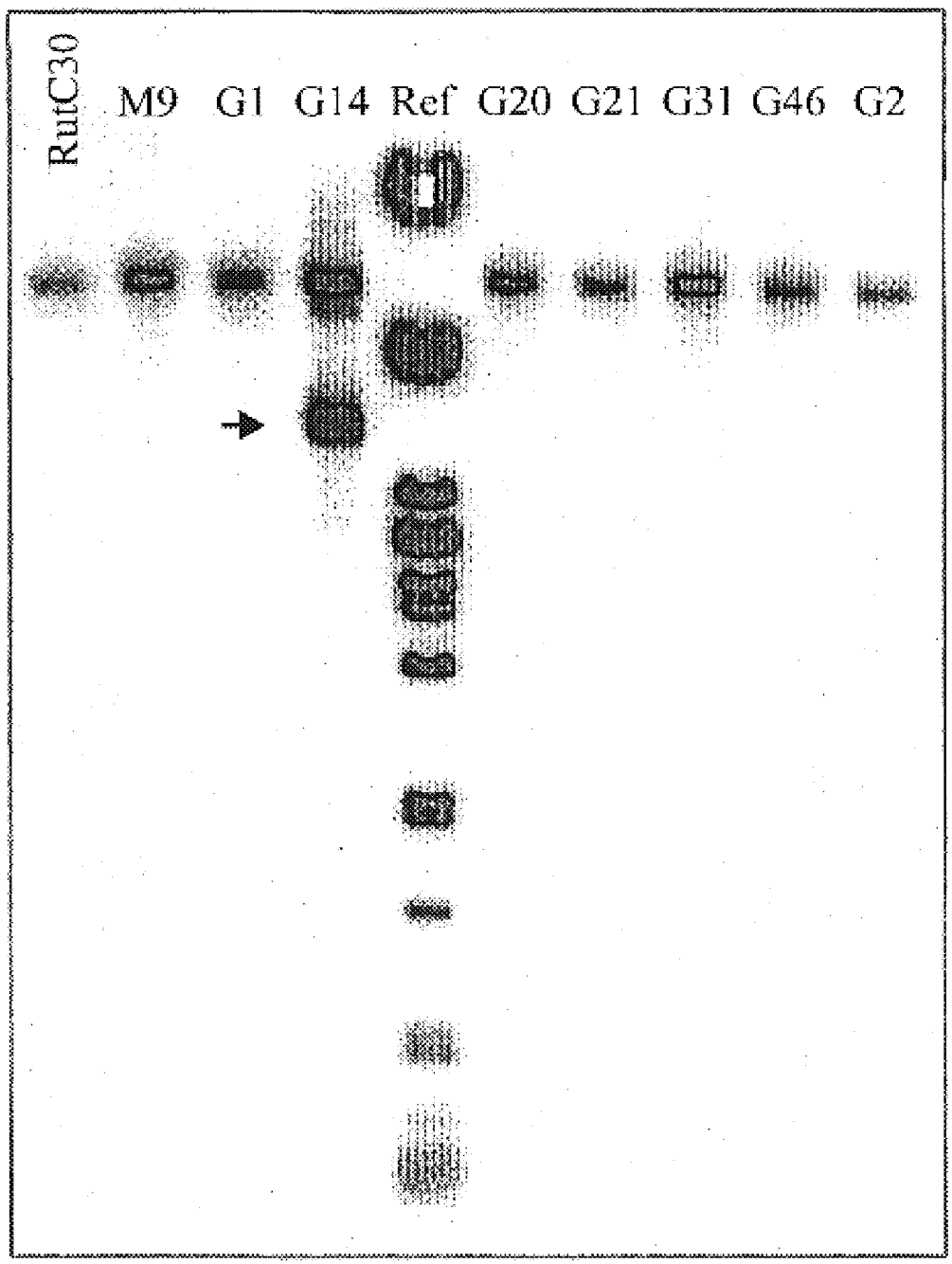
FIG. 9: Southern blot analysis of the genomic DNA of several hygromycin-resistant transformants and of the WT RutC30 strain: transformant g14 expresses both the mutant and the repaired glucosidase II alpha-subunit gene; all other transformants grow on hygromycin but have not integrated the repaired glucosidase II alpha-subunit gene into the genome. The fragment of 3400 bp (arrow) indicates the random integration of the glucosidase II expression cassette. The fragment of 5000 bp represents the hybridization signal against the endogenous mutant glucosidase II alpha subunit gene. Ref: PstI-digested lambda DNA as reference.
Figure 10:
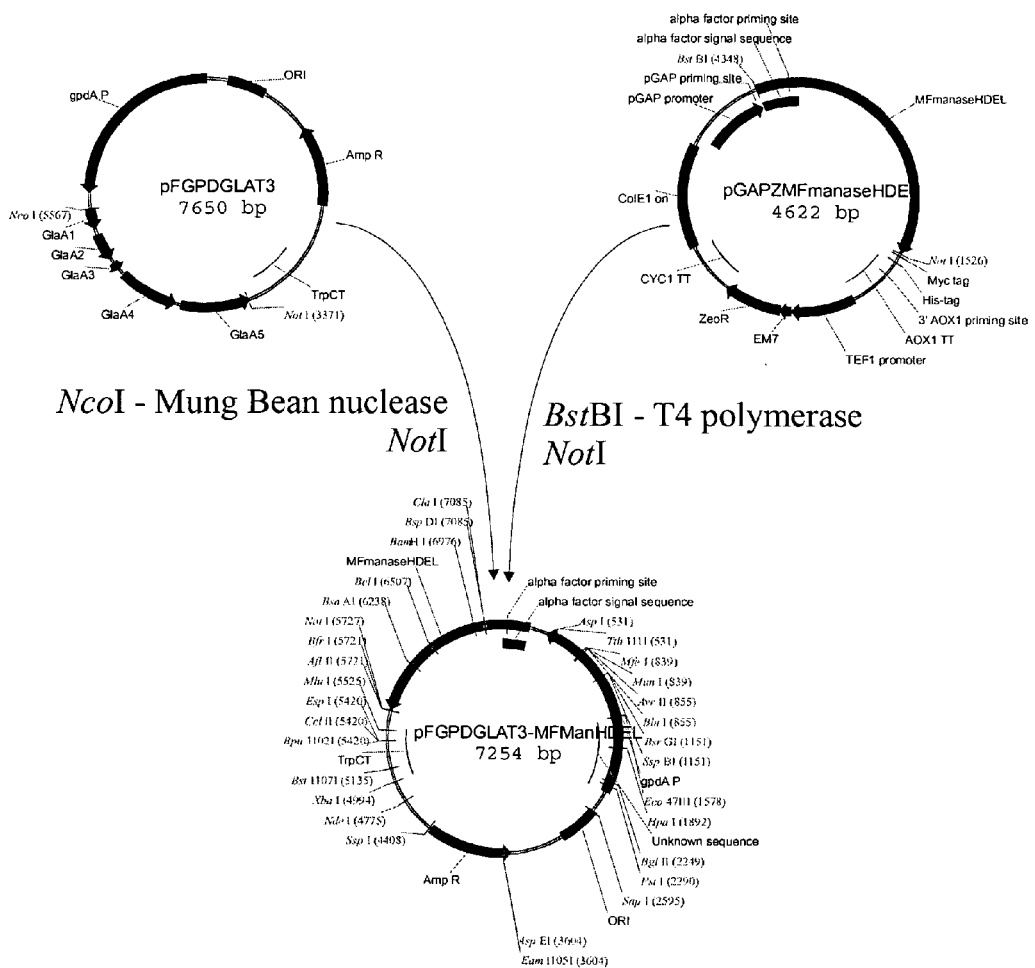
FIG. 10: Construction strategy for the α-1,2-mannosidase expression plasmid pFGPDLAT3-MFManHDEL.

Several hygromycin-resistant clones were analyzed by DSA-FACE. As described in Example 2, only one transformant (designated as g14) showed a severe difference in its N-glycan profile compared to the RutC30 untransformed strain. Southern analysis indicated that only g14 had randomly integrated the GIIα expression plasmid into its genome (FIG. 9).

Figure 15:
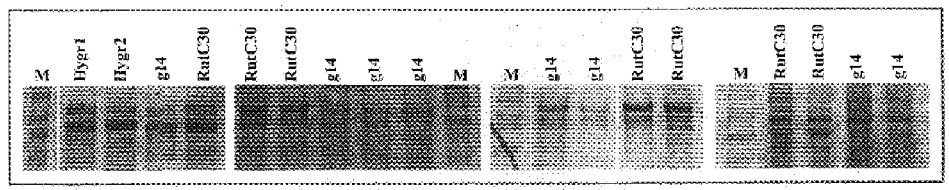
FIG. 15: Each gel represents separate experiments in which the secretion level of the g14 transformant and the RutC30 wild-type strain were compared with one another. For each analysis, the different protein samples were prepared from different but simultaneously grown cultures of both strains. In the first gel, Hygr1 and Hygr2 represent hygromycin-resistant RutC30 transformants that have no genomic integration of the full-size glucosidase II (checked on gDNA and via N-glycan analysis). As a result, they have a similar secretion behavior as the untransformed RutC30 strain.

Apart from the phenotype on the N-glycan level, also the secretion capacity of the g14 transformant seems to be affected. To analyze the effect on the production of extracellular proteins, several strains were grown on 50 ml minimal medium in 100 ml shaker flasks. Incubations were performed for six to seven days, at 30° C. and 150 rpm (rotations per minute). The minimal medium consists per liter of 20 g glucose, 5 g $(NH_4)_2SO_4$, 15 g $KH_2PO_4$, 0.3 g $CaCl_2$, 0.3 g $MgSO_4$ and mineral components. Since all analyzed clones are derived from the RutC30 strain, their cellulose expression is not subject to carbon catabolyte repression due to the absence of a functional CRE1 (Ilmen et al., 1996). Hence, a sufficient amount of extracellular hydrolase is synthesized to perform an SDS-PAGE analysis. The proteins are precipitated from the growth medium using TCA (trichloro-acetic acid), resuspended in 2× Laemmli loading buffer and analyzed via Gel electrophoresis (FIG. 15).

Interpretation of the observed SDS-PAGE profile indicates that the secretion capacity of the g14 transformant is reduced compared to the RutC30 WT and untransformed strains. The exercise was repeated several times to check the reproducibility of the obtained data. After growth on glucose minimal medium for six to seven days, the level of the g14 secretion seems to be lower than that of the RutC30 strain.

Example 6

Construction of a Glucosidase II Knock Out in *Saccharomyces cerevisiae*

Figure 16:
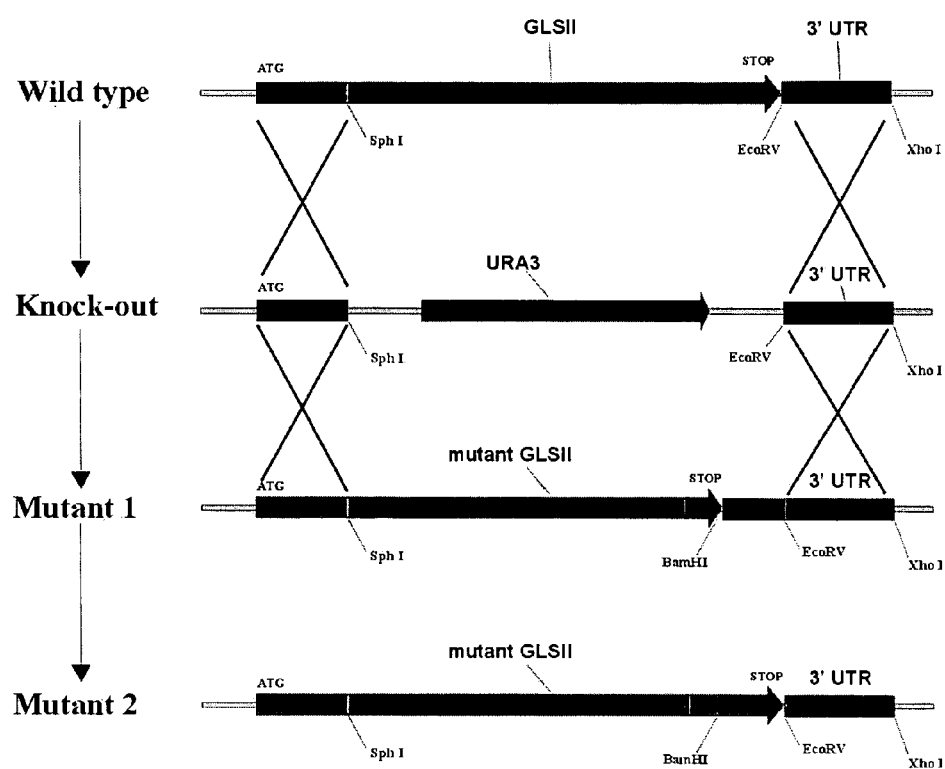
FIG. 16: Strategy for the construction of a *S. cerevisiae* rot2 knock out, and for the consequent replacement of the URA3 cassette by a mutant glucosidase II gene, carrying the RutC30 *T. reesei* glucosidase II mutation
Figure 17:
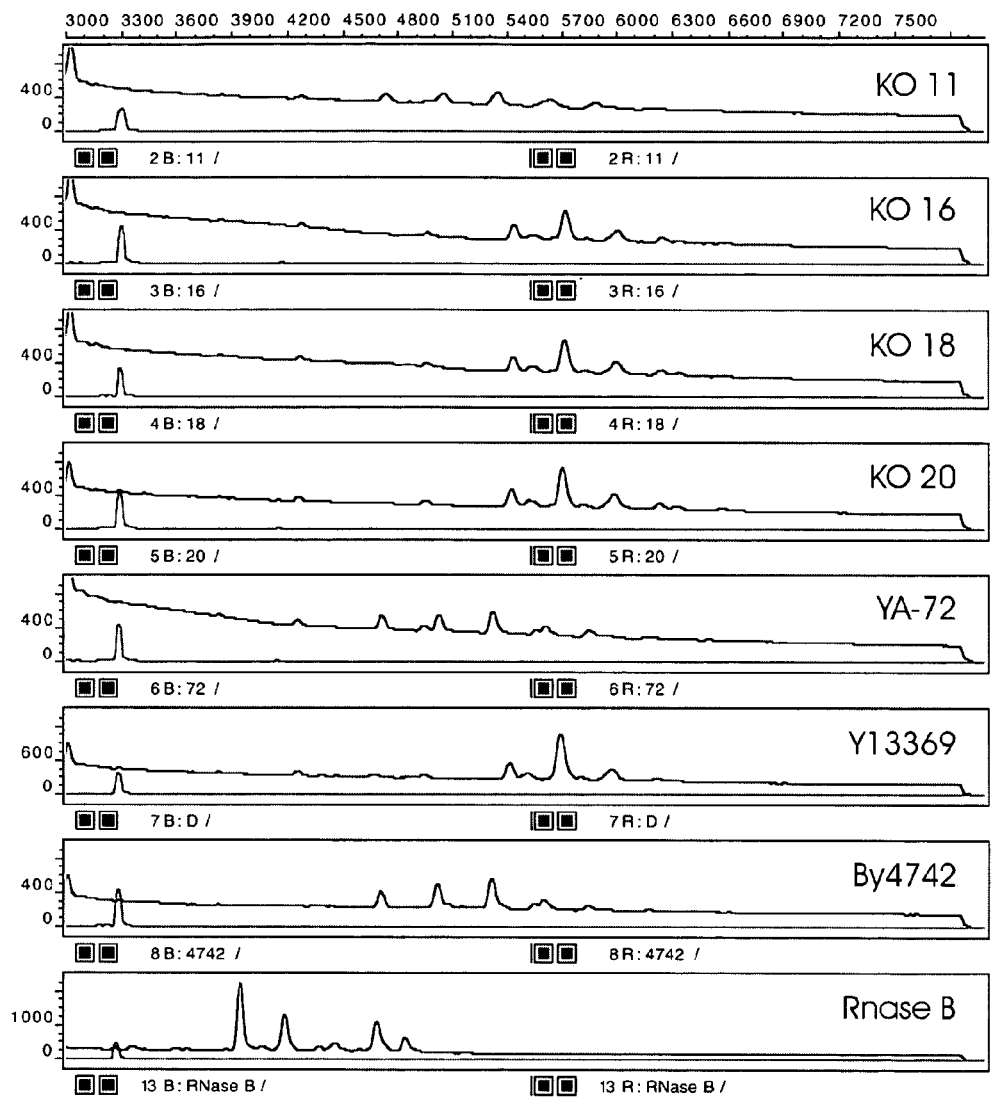
FIG. 17: DSA-FACE analysis of the rot2 knock out transformants (KO16, KO18, KO20) as confirmed by PCR, in comparison with a transformant with an aberrant PCR pattern (KO11) and the parental strain YA-72, and with the rot2 knock out mutant Y13369 and its parental strain BY4742. All rot2 knock outs show a similar sugar pattern that is clearly different from that of the wild-type strains.

The strategy to construct the ROT2 knock out is summarized in FIG. 16. pKOROT2 is a vector comprising an integration cassette consisting of a *S. cerevisiae* URA3 expression cassette inserted between about 60 bp of the 5' end of the ROT2 ORF at one side and the 3' end untranslated region of this ORF at the other side. The plasmid pKOROT2 was digested with XhoI to release the integration cassette. Transformation of *S. cerevisiae* YA-72 with this cassette and selection on a URA⁻ medium results in the selection of mutants in which the yeast glucosidase II gene has been replaced by the URA3 expression cassette. Transformants were tested using an upward primer in the URA3 gene and a downward primer in the 3' untranslated region. Three out of 19 analyzed clones were showing the right insert. The positive clones were tested on their sugar profile using DSA-FACE analysis, and compared with a negative clone, with the parental strain and with the rot2 knock out mutant Y13369 and its parental strain BY4742 (FIG. 17). From the sugar profiles, it can indeed be concluded that the glucosidase II gene was inactivated in the transformants.

FIG. 16 indicates how the URA3 gene in the knock out further can be exchanged against a mutant glucosidase II gene, carrying the mutation that is found in the *T. reesei* RutC30 glucosidase II.

Example 7

*S. cerevisiae* Strains with a Mutant Glucosidase II Show Increased Secretion

*S. cerevisiae* Y13369, as well as the parental strain BY4742 were transformed with the episomal plasmid pSC-GALMFHIFNB2, carrying the human IFNβ gene preceded by the *S. cerevisiae* mating factor and under control of the GAL1 promoter. Transformants were selected on URA⁻ medium. From both strains, eight transformants were analyzed by Western Blotting. The yeast strains were precultivated for 48 hours in YPD, and the expression was induced for 48 hours in YPGal. The proteins secreted in the medium were precipitated with TCA and separated using a 15% SDS-PAGE gel. Blotting was carried out by the semi-dry method, and the results are summarized in FIG. 18.

Although the results are not quantified, it is clear that in general the knockout mutants do secrete more IFNβ in the medium than the wild-type strain.

To obtain more quantitative data, the experiment was repeated and the secretion was compared with the secretion of an IFNβ-producing knock out complemented with a mutant glucosidase. This strain was obtained by transforming the IFNβ knock out strain with pYX132LEUGLSIImut3' and selection of SDC URA⁻ LEU⁻ medium.

Eight individual transformants of each strain (Y133369 transformed with pSCGALMFHIFNB2, BY4742 transformed with pSCGALMFHIFNB2 and Y13369 transformed with both pSCGALMFHIFNB2 and pYX132LEUGLSIImut3') were grown in selective medium (SDC URA⁻ or SDC URA⁻ LEU⁻) for 18 hours. Then the cells were harvested and washed three times with water. The expression was induced by resuspending the cells in SDGal URA⁻, resp. SDGal URA⁻ LEU⁻ and cultivating them for another 24 hours. The cells were pelleted and the medium was collected. The supernatant of each of the eight transformants was pooled. Two samples of the pooled supernatant, one of 0.5 ml and one of 1 ml was TCA precipitated. The proteins were separated using an SDS-PAGE gel, and blotted as described above. The results are summarized in FIG. 19 and Table 1. It is clear from these results that both the mutant glucosidase II and the knock out mutant show an increased secretion compared with the wild-type.

TABLE 1

Quantification of the protein bands of FIG. 19, as determined by Lumi Imager. A: analysis of the 0.5 ml sample B: analysis of the 1 ml sample. The values are expressed as relative intensity ratios

| A | | | |
|---|---|---|---|
|  | mut | KO | WT |
| Mut | 1 | 2.96 | 0.308 |
| KO | 0.338 | 1 | 0.104 |
| WT | 3.25 | 9.6 | 1 |

| B | | | |
|---|---|---|---|
|  | Mut | KO | WT |
| Mut | 1 | 2.66 | 0.93 |
| KO | 0.376 | 1 | 0.35 |
| WT | 1.073 | 2.85 | 1 |

REFERENCES

D'Alessio C., Fernandez F., Trombetta E. S., Parodi A. J. 1999. Genetic evidence for the heterodimeric structure of glucosidase II. The effect of disrupting the subunit-encoding genes on glycoprotein folding. J. Biol. Chem. 274:25899-905.

Alonso J. M., Santa-Cecilia A., Calvo P. 1993. Effect of bromoconduritol on glucosidase II from rat liver. A new kinetic model for the binding and hydrolysis of the substrate. Eur. J. Biochem. 215:37-42.

Altschul S. F., Gish W., Miller W., Myers E. W., Lipman D. J. 1990. Basic local alignment search tool. J. Mol. Biol. 215:403-10.

Appel R. D., Bairoch A., Hochstrasser D. F. A new generation of information retrieval tools for biologists: the example of the ExPASy WWW server. Trends Biochem. Sci. 19:258-60.

Arendt C. W., Ostergaard H. L. 1997. Identification of the CD45-associated 116-kDa and 80-kDa proteins as the alpha- and beta-subunits of alpha-glucosidase II. J. Biol. Chem. 272:13117-25.

Berger B., Wilson D. B., Wolf E., Tonchev T., Milla M., Kim P. S. 1995. Predicting coiled coils by use of pairwise residue correlations. Proc. Natl. Acad. Sci. U.S.A. 92:8259-63.

Callewaert N., Geysens S., Molemans F., Contreras R. 2001. Ultrasensitive profiling and sequencing of N-linked oligosaccharides using standard DNA-sequencing equipment. Glycobiology, 11:275-81.

Callewaert N., Laroy W., Cadirgi H., Geysens S., Saelens X., Min Jou W., Contreras R. 2001b. Use of HDEL-tagged T. Reesei mannosyl oligosaccharide 1,2-alpha-D-mannosidase for N-glycan engineering in Pichia pastoris. FEBS Lett. 503:173-8.

Camirand A., Heysen A., Grondin B., Herscovics A. 1991. Glycoprotein biosynthesis in Saccharomyces cerevisiae. Isolation and characterization of the gene encoding a specific processing alpha-mannosidase. J. Biol. Chem. 266:15120-7.

Casadaban M. J., Cohen S. N. 1980. Analysis of gene control signals by DNA fusion and cloning in Escherichia coli. J. Mol. Biol. 138:179-207.

Chiba Y., Suzuki M., Yoshida S., Yoshida A., Ikenaga H., Takeuchi M., Jigami Y., Ichishima E. 1998. Production of human compatible high mannose-type ($Man_5GlcNAc_2$) sugar chains in Saccharomyces cerevisiae. J. Biol. Chem. 273:26298-304.

Contreras R., Carrez D., Kinghorn J. R., van den Hondel C. A., Fiers W. 1991. Efficient KEX2-like processing of a glucoamylase-interleukin-6 fusion protein by Aspergillus nidulans and secretion of mature interleukin-6. Biotechnology (N.Y.) 9:378-81.

De Bruyn A., Maras M., Schraml J., Herdewijn P., Contreras R. 1997. NMR evidence for a novel asparagine-linked oligosaccharide on cellobiohydrolase I from T. Reesei RUTC 30. FEBS Lett. 405:111-3.

de Groot M. J., Bundock P., Hooykaas P. J., Beijersbergen A. G. 1998. Agrobacterium tumefaciens-mediated transformation of filamentous fungi. Nat. Biotechnol. 16:839-42.

Demolder J., Fiers W., Contreras R. 1994. Human interferon-beta, expressed in Saccharomyces cerevisiae, is predominantly directed to the vacuoles. Influence of modified co-expression of secretion factors and chaperones. J. Biotechnol. 32:179-89.

Eades C. J., Gilbert A. M., Goodman C. D., Hintz W. E. 1998. Identification and analysis of a class 2 alpha-mannosidase from Aspergillus nidulans. Glycobiology, 8:17-33.

Flura T., Brada D., Ziak M., Roth J. 1997. Expression of a cDNA encoding the glucose trimming enzyme glucosidase II in CHO cells and molecular characterization of the enzyme deficiency in a mutant mouse lymphoma cell line. Glycobiology, 7:617-24.

Freeze H. H. 1985. Interaction of Dictyostelium discoideum lysosomal enzymes with the mammalian phosphomannosyl receptor. The importance of oligosaccharides which contain phosphodiesters. J. Biol. Chem. 260:8857-64.

Fukada T., Iida K., Kioka N., Sakai H., Komano T. 1994. Cloning of a cDNA encoding N-acetylglucosaminyltransferase I from rat liver and analysis of its expression in rat tissues. Biosci. Biotechnol. Biochem. 58:200-201.

Garcia R., Cremata J. A., Quintero O., Montesino R., Benkestock K., Stahlberg J. 2001. Characterization of protein glycoforms with N-linked neutral and phosphorylated oligosaccharides: studies on the glycosylation of endoglucanase 1 (Cel7B) from T. Reesei. Biotechnol. Appl. Biochem. 33 (Pt2):141-152.

Goldman G., Van Montagu M., Herrera-Estrella A. 1990. Transformation of Trichoderma harzianum by high-voltage electric pulse. Curr. Genet. 17:1169-1174.

Grossberg, S. E. et al. 1986. In Manual of clinical immunology. N. R. Rose, H. R. Friedman, and J. L. Fahey (eds.). ASM Press, Washington, D.C. 1986, pp 259-299.

Herscovics A., Schneikert J., Athanassiadis A., Moremen K. W. 1994. Isolation of a mouse Golgi mannosidase cDNA, a member of a gene family conserved from yeast to mammals. J. Biol. Chem. 269:9864-9871.

Hiraoka Y., Toda T., Yanagida M. 1984. The NDA3 gene of fission yeast encodes beta-tubulin: a cold-sensitive nda3 mutation reversibly blocks spindle formation and chromosome movement in mitosis. Cell, 39(2 Pt1):349-58.

Hynes M. J., Corrick C. M., King J. A. 1983. Isolation of genomic clones containing the amdS gene of *Aspergillus nidulans* and their use in the analysis of structural and regulatory mutations. Mol. Cell. Biol. 3:1430-1439.

Ilmen M., Thrane C., Penttila M. 1996. The glucose repressor gene cre1 of *Trichoderma*: isolation and expression of a full-length and a truncated mutant form. Mol. Gen. Genet. 251:451-560.

Kornfeld R., Kornfeld S. 1985. Assembly of asparagine-linked oligosaccharides. Annu. Rev. Biochem. 54:631-64.

Lal A., Schutzbach J. S., Forsee W. T., Neame P. J., Moremen K. W. 1994. Isolation and expression of murine and rabbit cDNAs encoding an alpha 1,2-mannosidase involved in the processing of asparagine-linked oligosaccharides. J. Biol. Chem. 269:9872-9881.

Lorito M., Hayes C. K., Di Pietro A., Harman G. E. 1993. Biolistic transformation of *Trichoderma harzianum* and *Gliocladium virens* using plasmid and genomic DNA. Curr. Genet., 24:349-56.

Lussier M., Sdicu A. M., Ketela T., Bussey H. 1995. Localization and targeting of the *Saccharomyces cerevisiae* Kre2p/Mnt1p alpha 1,2-mannosyltransferase to a medial-Golgi compartment. J. Cell. Biol. 131:913-27.

Maras M., De Bruyn A., Schraml J., Herdewijn P., Claeyssens M., Fiers W., Contreras R. 1997. Structural characterization of N-linked oligosaccharides from cellobiohydrolase I secreted by the filamentous fungus *T. Reesei* RUTC 30. Eur. J. Biochem. 245:617-25.

Maras M., van Die I., Contreras R., van den Hondel C. A. 1999. Filamentous fungi as production organisms for glycoproteins of bio-medical interest. Glycoconj. J. 16:99-107.

Maras M., Callewaert N., Piens K., Claeyssens M., Martinet W., Dewaele S., Contreras H., Dewerte I., Penttila M., Contreras R. 2000. Molecular cloning and enzymatic characterization of a *Trichoderma reesei* 1,2-alpha-D-mannosidase. J. Biotechnol. 77(2-3):255-63.

Martinet W., Maras M., Saelens X., Min Jou W., Contreras R. 1998. Modification of the protein glycosylation pathway in the methylotrophic yeast *Pichia pastoris*. Biotechnology Letters 20:1171-1177.

Martinez-Blanco H., Orejas M., Reglero A., Luengo J. M., Penalva M. A. 1993. Characterization of the gene encoding acetyl-CoA synthetase in *Penicillium chrysogenum*: conservation of intron position in plectomycetes. Gene, 130:265-70.

Mattern I. E., Punt P. J., van den Hondel C. A. 1988. Fungal Gen. Newslett. 35, 25.

May G. S., Morris N. R. 1987. The unique histone H2A gene of *Aspergillus nidulans* contains three introns. Gene, 58:59-66.

Mount S. M. 1982. A catalogue of splice junction sequences. Nucleic Acids Res. 10:459-72.

Odani T., Shimma Y., Tanaka A., Jigami Y. 1996. Cloning and analysis of the MNN4 gene required for phosphorylation of N-linked oligosaccharides in *Saccharomyces cerevisiae*. Glycobiology, 6:805-10.

Orbach M. J., Porro E. B., Yanofsky C. 1986. Cloning and characterization of the gene for beta-tubulin from a benomyl-resistant mutant of *Neurospora crassa* and its use as a dominant selectable marker. Mol. Cell Biol. 6:2452-61.

Papac D. I., Briggs J. B., Chin E. T., Jones A. J. 1998. A high-throughput microscale method to release N-linked oligosaccharides from glycoproteins for matrix-assisted laser desorption/ionization time-of-flight mass spectrometric analysis. Glycobiology, 8:445-54.

Pearson W. R., Wood T., Zhang Z., and Miller W. 1997. Comparison of DNA sequences with protein sequences. Genomics 46:24-36.

Pelham H. R. 1988. Evidence that luminal ER proteins are sorted from secreted proteins in a post-ER compartment. EMBO J. 7:913-918.

Penttila M., Nevalainen H., Ratto M., Salminen E., Knowles J. 1987. A versatile transformation system for the cellulolytic filamentous fungus *Trichoderma reesei*. Gene, 61:155-64.

Punt P. J., Oliver R. P., Dingemanse M. A., Pouwels P. H., van den Hondel C. A. 1987. Transformation of *Aspergillus* based on the hygromycin B resistance marker from *Escherichia coli*. Gene, 56:117-24.

Punt P. J., van Biezen N., Conesa A., Albers A., Mangnus J., van den Hondel C. 2002. Filamentous fungi as cell factories for heterologous protein production. Trends Biotechnol. 20:200-6.

Redlich P. N. and Grossberg S. E. 1989. Analysis of antigenic domains on natural and recombinant human IFNβ by the inhibition of biologic activities with monoclonal antibodies. J. Immunol. 143:1887-93.

Saloheimo A., Henrissat B., Hoffren A. M., Teleman O., Penttila M. 1994. A novel, small endoglucanase gene, egl5, from *Trichoderma reesei* isolated by expression in yeast. Mol. Microbiol., 13:219-28.

Sambrook J., Fritsch E. F., Maniatis T. (1989) Molecular cloning: a laboratory manual, $2^{nd}$ ed. Cold Spring Harbor Laboratory, Cold Spring Harbor, N.Y.

Sarkar M., Hull E., Nishikawa Y., Simpson R. J., Moritz R. L., Dunn R., Schachter H. 1991. Molecular cloning and expression of cDNA encoding the enzyme that controls conversion of high-mannose to hybrid and complex N-glycans: UDP-N-acetylglucosamine: alpha-3-D-mannoside beta-1,2-N-acetylglucosaminyl-transferase I. Proc. Natl. Acad. Sci. U.S.A. 88:234-238.

Schachter H. 1991. Organization and localization to chromosome 5 of the human UDP-N-acetylglucosamine:alpha-3-D-mannoside beta-1,2-N-acetylglucosaminyltransferase I gene. Biochem. Biophys. Res. Commun. 176:608-615.

Sears I. B., O'Connor J., Rossanese O. W. and Glick B. S. 1998. A versatile set of vectors for constitutive and regulated gene expression in *Pichia pastoris*. Yeast vol. 14:783-790.

Takaya N., Yanai K., Horiuchi H., Ohta A., Takagi M. 1994. Cloning and characterization of two 3-phosphoglycerate kinase genes of *Rhizopus niveus* and heterologous gene expression using their promoters. Curr. Genet. 25:524-30.

Takumi T., Lodish H. F. 1994. Rapid cDNA cloning by PCR screening. Biotechniques, 17:443-444.

Thompson J. D., Higgins D. G., Gibson T. J. 1994. CLUSTAL W: improving the sensitivity of progressive multiple sequence alignment through sequence weighting, position-specific gap penalties and weight matrix choice. Nucleic Acids Res. 22:4673-80.

Tremblay L. O., Campbell Dyke N., Herscovics A. 1998. Molecular cloning, chromosomal mapping and tissue-specific expression of a novel human alpha-1,2-mannosidase gene involved in N-glycan maturation. Glycobiology 8:585-595.

Trombetta E. S., Simons J. F., Helenius A. 1996. Endoplasmic reticulum glucosidase II is composed of a catalytic subunit, conserved from yeast to mammals, and a tightly bound noncatalytic HDEL-containing subunit. J. Biol. Chem. 271 (44):27509-16.

Van Petegem F., Contreras H., Contreras R., Van Beeumen J. 2001. *Trichoderma reesei* alpha-1,2-mannosidase: structural basis for the cleavage of four consecutive mannose residues. J. Mol. Biol. 312:157-65.

Wang X. H., Nakayama K., Shimma Y., Tanaka A., Jigami Y. 1997. MNN6, a member of the family, is the gene for mannosylphosphate transfer in *Saccharomyces cerevisiae*. J. Biol. Chem. 272:18117-24.

What is claimed is:

1. An improvement in a method for secreting protein from a filamentous fungus cell, the improvement comprising:
   utilizing a glucosidase II mutation to increase protein secretion from the filamentous fungus cell.

2. The method according to claim 1, wherein said filamentous fungus cell is selected from the group genera consisting of the genera *Aspergillus, Fusarium, Geotrichum, Monascus, Monilia, Mucor, Penecillium, Rhizopus, Trichoderma* and *Ustilago*.

3. The method according to claim 1, wherein said filamentous fungus cell is a *Trichoderma* sp.

4. An improvement in a method of the type involving using yeast to secrete protein, the improvement comprising:
   using in the method a yeast selected from the group consisting of *Kluyveromyces* sp., *Pichia* sp., *Hansenula* sp. or *Schizosaccharomyces pombe*, the yeast having a defective glucosidase II as host for protein secretion.

* * * * *